(12) United States Patent
Longo et al.

(10) Patent No.: US 9,237,761 B2
(45) Date of Patent: Jan. 19, 2016

(54) METHODS AND DIETS FOR LOWERING GLUCOSE AND/OR IGF-1 LEVELS

(71) Applicant: University of Southern California, Los Angeles, CA (US)

(72) Inventors: Valter D. Longo, Playa del Rey, CA (US); Sebastian Brandhorst, Los Angeles, CA (US); Morgan Elyse Levine, Santa Barbara, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 14/178,953

(22) Filed: Feb. 12, 2014

(65) Prior Publication Data

US 2014/0227373 A1 Aug. 14, 2014

Related U.S. Application Data

(63) Continuation of application No. 61/763,797, filed on Feb. 12, 2013.

(51) Int. Cl.
| | | |
|---|---|---|
| A61K 31/20 | (2006.01) | |
| A61K 38/00 | (2006.01) | |
| A23L 1/29 | (2006.01) | |
| A23L 1/305 | (2006.01) | |
| A61K 31/405 | (2006.01) | |
| A61K 31/23 | (2006.01) | |
| A61K 31/4172 | (2006.01) | |
| A61K 31/401 | (2006.01) | |
| A61K 31/205 | (2006.01) | |

(52) U.S. Cl.
CPC ................ *A23L 1/293* (2013.01); *A23L 1/305* (2013.01); *A61K 31/205* (2013.01); *A61K 31/23* (2013.01); *A61K 31/401* (2013.01); *A61K 31/405* (2013.01); *A61K 31/4172* (2013.01)

(58) Field of Classification Search
CPC . A61K 31/205; A61K 31/401; A61K 31/405; A61K 31/4172; A61K 31/23
USPC ........................................... 514/560, 6.8, 7.2
See application file for complete search history.

(56) References Cited

FOREIGN PATENT DOCUMENTS

WO  WO 2006069918 A1 *  7/2006
WO     2011/050302 A2     4/2011

OTHER PUBLICATIONS

Doyle, C. et al., "Nutrition and Physical Activity During and After Cancer Treatment: An American Cancer Society Guide for Informed Choices," CA Cancer J. Clin 2006: v. 56, n. 6, Nov./Dec. 2006, pp. 323-353.
Lee, C. et al., "Fasting Cycles Retard Growth of Tumors and Sensitize a Range of Cancer Cell Types to Chemotherapy," Sci Transl Med., 2012, pp. 1-17.
Lee, C. et al., "Reduced Levels of IGF-I Mediate Differential Protection of Normal Cancer Cells in Response to Fasting and Improve Chemotherapeutic Index," Cancer Res; 70(4), Feb. 15, 2010, pp. 1564-1592.
Raffaghello, L. et al., "Starvation-dependent differential stress resistance protects normal but not cancer cells against high-dose chemotherapy," PNAS, Jun. 17, 2008, v. 105, n. 24, pp. 8215-8220.
Safdie, F.M. et al., "Fasting and cancer treatment in humans: A case series report," AGING, Dec. 2009, v. 1, n. 12, pp. 1-20.
Safdie, F.M. et al., "Fasting Enhances the Response of Glioma to Chemo- and Radiotherapy," PLOS ONE, Sep. 2012, v. 7, issue 9, pp. 1-9.
Lee, C. et al., "Fasting vs dietary restriction in cellular protection and cancer treatment: from model organisms to patients," Oncogene (2011) 30, pp. 3305-3316.

* cited by examiner

*Primary Examiner* — Kevin E Weddington
(74) *Attorney, Agent, or Firm* — Brooks Kushman P.C.

(57) ABSTRACT

A method of improving longevity and/or alleviating a symptom of aging or preventing age related diseases is provided. The method includes a step in which the subject's average and type of daily protein intake, IGF-I, and IGFBP1 levels, and risk factors for overall mortality, cancer and diabetes are determined. With respect to protein consumption, the relative amounts of protein calories from animal and plant sources are determined. A periodic normal calorie or low calorie but low protein fasting mimicking diet with frequencies of every 2 weeks to 2 months is provided to the subject if the subject's average daily protein intake level and type and/or IGF-I levels, and/or IGFBP1 levels is identified as being greater or lower than a predetermined cutoff intake/level and if the subject is younger than a predetermined age. The method is also shown to alleviate symptoms of chemotoxicity.

22 Claims, 45 Drawing Sheets

| Body Weight | Day1 | Day2 | Day3 | Day4 | Day5 | Δ5-day¹ | Δ5-day² |
|---|---|---|---|---|---|---|---|
| | *kcal/day* | | | | | | |
| ≥200 lbs | 1170 | 828 | 768 | 810 | 833 | -5591 | -9591 |
| 151-200 lbs | 1134 | 790 | 737 | 774 | 795 | -5772 | -7772 |
| ≤150 lbs | 1098 | 751 | 706 | 738 | 756 | -5952 | -5952 |
| | *kcal/lb* | | | | | | |
| 250 lbs | 4.7 | 3.3 | 3.1 | 3.2 | 3.3 | | |
| 200 lbs | 5.7 | 3.9 | 3.7 | 3.9 | 4.0 | | |
| 150 lbs | 7.3 | 5.0 | 4.7 | 4.9 | 5.0 | | |
| | *kcal/kg* | | | | | | |
| 113 kg | 10.3 | 7.3 | 6.8 | 7.1 | 7.3 | | |
| 91 kg | 12.5 | 8.7 | 8.1 | 8.5 | 8.8 | | |
| 68 kg | 16.1 | 11.0 | 10.4 | 10.8 | 11.1 | | |

*Fig. 1*

|  | Day 1 | Day 2,3,4,5 |
|---|---|---|
| Total Calorie | 1152 | 809 |
| Fat | 56% | 46% |
| Carbohydrate | 34% | 46% |
| Sugar | 10% | 9% |
| Protein | 10% | 9% |

Table 10.

Fig. 2

|  | Unit | Day1 | % DV* | Day 2,3,4,5 | % DV* | Ave % DV* |
|---|---|---|---|---|---|---|
| Protein | g | 29 |  | 18 |  |  |
| Fat | g | 72 |  | 41 |  |  |
| Carb (by diff) | g | 98 |  | 91 |  |  |
| From Sugars | g | 29 |  | 17.6 |  |  |
| Dietary Fiber | g | 22 | 86% | 14 | 56% | 62% |
| Calcium | mg | 604 | 60% | 426 | 43% | 46% |
| Iron | mg | 13 | 77% | 10 | 55% | 60% |
| Magnesium | mg | 387 | 97% | 230 | 58% | 65% |
| Phosphorus | mg | 390 | 39% | 276 | 28% | 30% |
| Potassium (K) | mg | 2519 | 72% | 1795 | 51% | 55% |
| Sodium (Na) | mg | 2427 | 101% | 1750 | 73% | 79% |
| Zinc | mg | 7 | 46% | 4.2 | 28% | 32% |
| Copper | mg | 1.5 | 76% | 1.2 | 59% | 63% |
| Manganese | mg | 3 | 148% | 1.9 | 95% | 105% |
| Selenium | mcg | 7 | 10% | 5.3 | 8% | 8% |
| Vit A | IU | 39254 | 785% | 27549 | 551% | 598% |
| Vit C | mcg | 236 | 393% | 137 | 229% | 261% |
| Vit B1 Thiamin | mg | 4 | 209% | 2.2 | 113% | 132% |
| Vit B2 Riboflavin B2 | mg | 3.8 | 191% | 2 | 109% | 126% |
| Vit B3 Niacin | mg | 28.5 | 143% | 18 | 92% | 102% |
| Vit B5 Pantothenic Acid | mg | 1.2 | 12% | 1.0 | 10% | 10% |
| Vit B6 Pyridoxal Phosphate | mg | 4.0 | 200% | 2.2 | 111% | 129% |
| Vit B9 Folate | mg | 479 | 120% | 317 | 79% | 87% |
| B12 Cobalamin | mcg | 16 | 227% | 16 | 227% | 227% |
| Vit D | IU | 952 | 238% | 952 | 238% | 238% |
| Vit E | mcg | 25 | 127% | 16 | 80% | 89% |
| Vit K | mg | 1795 | 2243% | 1110 | 1387% | 1559% |

*Fig. 3*

Table 12. Associations between Mortality and Protein intake

| | Hazard Ratio (95% CI) | | | | | | | |
|---|---|---|---|---|---|---|---|---|
| | Ages 50-65 (N=3,039) | | | | Ages 66+ (N=3,342) | | | |
| | Model 1 | Model 2 | Model 3 | Model 4 | Model 1 | Model 2 | Model 3 | Model 4 |
| All-Cause Mortality | | | | | | | | |
| Moderate Protein (n=4,798) | 1.34 (0.81-2.22) | 1.37 (0.82-2.27) | 1.35 (0.80-2.29) | 1.15 (0.67-1.96) | 0.79 (0.62-0.99) | 0.79 (0.62-0.99) | 0.79 (0.62-0.99) | 0.79 (0.61-1.01) |
| High Protein (n=1,146) | 1.74 (1.02-2.97) | 1.77 (1.03-3.03) | 1.74 (0.99-3.05) | 1.18 (0.60-2.31) | 0.72 (0.55-0.94) | 0.73 (0.56-0.95) | 0.72 (0.55-0.94) | 0.72 (0.50-1.02) |
| % kcal Fat | | 0.99 (0.98-1.01) | | | | 1.00 (0.99-1.01) | | |
| %kcal Carbs | | | 1.00 (0.99-1.01) | | | | 1.00 (0.99-1.00) | |
| % kcal Animal Protein | | | | 1.03 (1.00-1.06) | | | | 1.00 (0.98-1.02) |
| CVD Mortality | | | | | | | | |
| Moderate Protein (n=4,798) | 0.79 (0.40-1.54) | 0.83 (0.43-1.60) | 0.81 (0.41-1.62) | 0.61 (0.29-1.29) | 0.80 (0.57-1.12) | 0.80 (0.57-1.12) | 0.80 (0.57-1.12) | 0.80 (0.56-1.14) |
| High Protein (n=1,146) | 1.03 (0.51-2.09) | 1.08 (0.54-2.15) | 1.10 (0.52-2.31) | 0.55 (0.19-1.62) | 0.78 (0.54-1.14) | 0.79 (0.54-1.15) | 0.78 (0.53-1.15) | 0.77 (0.48-1.25) |
| % kcal Fat | | 0.99 (0.97-1.01) | | | | 1.00 (0.99-1.01) | | |
| % kcal Carbs | | | 1.00 (0.99-1.02) | | | | 1.00 (0.99-1.01) | |
| % kcal Animal Protein | | | | 1.04 (0.99-1.11) | | | | 1.00 (0.98-1.02) |
| Cancer Mortality | | | | | | | | |
| Moderate Protein (n=4,798) | 3.06 (1.49-6.25) | 3.13 (1.52-6.44) | 3.56 (1.65-7.65) | 2.71 (1.24-5.91) | 0.67 (0.43-1.06) | 0.67 (0.43-1.06) | 0.67 (0.42-1.05) | 0.66 (0.40-1.07) |
| High Protein (n=1,146) | 4.33 (1.96-9.56) | 4.42 (2.01-9.74) | 4.98 (2.13-11.66) | 3.19 (1.21-8.35) | 0.40 (0.23-0.71) | 0.41 (0.23-0.73) | 0.39 (0.22-0.69) | 0.36 (0.17-0.82) |
| % kcal Fat | | 0.99 (0.98-1.01) | | | | 1.02 (1.01-1.03) | | |
| % kcal Carbs | | | 1.00 (0.98-1.01) | | | | 1.00 (0.99-1.01) | |
| % kcal Animal Protein | | | | 1.02 (0.97-1.07) | | | | 1.00 (0.97-1.04) |
| Diabetes Mortality | | | | | | | | |
| Moderate Protein (n=4,798) | 3.43 (0.69-17.02) | 3.36 (0.67-16.96) | 3.41 (0.67-17.36) | 2.99 (0.58-15.31) | 5.38 (0.95-30.49) | 5.05 (0.93-27.34) | 4.93 (0.89-27.35) | 8.20 (0.35-37.01) |
| High Protein (n=1,146) | 3.93 (0.73-21.07) | 3.88 (0.71-21.17) | 3.90 (0.67-22.84) | 2.77 (0.24-31.73) | 10.64 (1.85-61.31) | 10.42 (1.88-57.87) | 9.07 (1.49-55.30) | 15.16 (1.93-118.9) |
| % kcal Fat | | 1.01 (0.97-1.05) | | | | | | |
| % kcal Carbs | | | 1.00 (0.96-1.04) | | | | | |
| % kcal Animal Protein | | | | 1.02 (0.92-1.14) | | | | |

*Fig. 8*

| Table 13: Sample Characteristics | | | | |
|---|---|---|---|---|
| | Full-Samples N=(6,381) | Low Protein (N=437) | Moderate Protein (N=4,798) | High Protein (N=1,146) |
| Age | 64.8 (10.0) | 65.3 (10.1) | 64.8 (10.0) | 64.5 (9.8) |
| Female | 55.4 | 56.3 | 55.0 | 57.0 |
| White | 85.1 | 81.6 | 86.5 | 80.3 |
| Black | 8.7 | 12.3 | 7.9 | 10.9 |
| Hispanic | 6.2 | 6.1 | 5.6 | 8.8 |
| Education | 11.5 (3.6) | 11.1 (3.3) | 11.6 (3.5) | 11.0 (3.8) |
| Waist Circumference (cm) | 96.9 (13.2) | 96.5 (13.5) | 96.8 (13.2) | 97.5 (13.0) |
| Current Smoker | 19.1 | 21.8 | 19.1 | 18.2 |
| Former Smoker | 38.0 | 39.8 | 37.9 | 37.8 |
| History of MI | 9.1 | 7.8 | 8.9 | 10.2 |
| History of Cancer | 7.3 | 11.7 | 7.5 | 5.0 |
| History of Diabetes | 10.9 | 2.6 | 10.3 | 17.0 |
| Tried to lose weight | 38.2 | 37.5 | 37.0 | 43.9 |
| Changed diet (health reason) | 23.1 | 15.0 | 22.4 | 29.3 |
| % Calories from Animal Protein | 10.6 (5.1) | 4.1 (1.8) | 9.5 (3.1) | 18.3 (4.9) |
| % Calories from Protein | 16.0 (4.8) | 8.5 (1.4) | 14.9 (2.6) | 23.7 (4.1) |
| % Calories from Fat | 33.0 (9.6) | 31.9 (11.2) | 33.6 (9.3) | 31.0 (10.2) |
| % Calories from Carbs | 50.7 (11.6) | 56.6 (13.5) | 51.3 (11.0) | 45.4 (11.4) |
| Total Calories | 1,822.9 (832.2) | 1065.6 (1072.8) | 1862.5 (807.4) | 1593.6 (706.2) |
| 24-hr Recall More | 1.6 | 1.8 | 1.4 | 2.1 |
| 24-hr Recall Usual | 93.3 | 83.0 | 93.9 | 94.6 |
| 24-hr Recall Less | 5.1 | 15.2 | 4.7 | 3.3 |
| Died (All-Cause) | 40.4 | 42.9 | 39.6 | 42.9 |
| Died (CVD) | 18.7 | 21.3 | 18.0 | 20.7 |
| Died (Cancer) | 9.9 | 9.8 | 10.1 | 9.0 |
| Died (Diabetes) | 1.0 | 0.2 | 0.9 | 2.0 |
| Person Years | 83,308 | 5,183 | 63,661 | 14,464 |
| BMI: Body Mass Index; MI: Myocardial Infarction; 24-hr Recall (More/Usual/Less): Food reported during 24-hour recall is (more than/same as/less than) subject's normal diet; CVD: Cardiovascular disease | | | | |

*Fig. 13*

Table 14: Association between Protein Intake and Mortality (N=6,381)

| Proten (% kcal) | Hazard Ratio (95% CI) | | | |
| --- | --- | --- | --- | --- |
| | All-Cause Mortality | CVD Mortality | Cancer Mortality | Diabetes Mortality |
| <10 (n=436) | reference | reference | reference | reference |
| 10-19.9 (n=4,800) | 0.90 (0.74-1.11) | 0.82 (0.61-1.11) | 0.98 (0.66-1.45) | 3.23 (1.02-10.20) |
| 20+ (n=1,145) | 0.93 (0.74-1.19) | 0.88 (0.63-1.22) | 0.89 (0.56-1.44) | 5.51 (1.69-17.99) |

*Fig. 14*

Table 15: The Influence of IGF-I on the Association between Mortality and Protein Intake (N=2,253)

| | Hazard Ratio (95% CI) | | | |
|---|---|---|---|---|
| | Ages 50-65 (N=1,125) | | Ages 66+ (N=1,128) | |
| | Model 1 | Model 2 | Model 1 | Model 2 |
| All-Cause Mortality | | | | |
| Low Protein | Reference | Reference | Reference | Reference |
| Moderate Protein | 1.73 (0.91-3.30) | 1.69 (0.90-3.20) | 0.62 (0.41-0.94) | 0.62 (0.40-0.94) |
| High Protein | 2.83 (1.39-5.76) | 2.71 (1.34-5.47) | 0.59 (0.36-0.95) | 0.59 (0.37-0.95) |
| IGF-I (10 ng/ml) | | 1.01 (0.99-1.04) | | 1.00 (0.98-1.01) |
| CVD Mortality | | | | |
| Low Protein | Reference | Reference | Reference | Reference |
| Moderate Protein | 0.76 (0.33-1.74) | 0.71 (0.33-1.54) | 0.77 (0.43-1.38) | 0.77 (0.43-1.37) |
| High Protein | 1.29 (0.49-3.40) | 1.03 (0.39-2.75) | 0.69 (0.36-1.34) | 0.70 (0.36-1.35) |
| IGF-I (10 ng/ml) | | 1.04 (1.01-1.07) | | 0.99 (0.97-1.00) |
| Cancer Mortality | | | | |
| Low Protein | Reference | Reference | Reference | Reference |
| Moderate Protein | 6.91 (1.56-30.68) | 6.91 (1.56-30.72) | 0.41 (0.18-0.92) | 0.39 (0.18-0.86) |
| High Protein | 13.05 (2.77-61.40) | 13.09 (2.80-61.13) | 0.24 (0.08-0.68) | 0.23 (0.08-0.67) |
| IGF-I (10 ng/ml) | | 1.00 (0.96-1.03) | | 0.97 (0.94-0.99) |

Fig. 15

Table 16: Hazard Ratios for the Interaction between Protein and IGF-I on Mortality

|  | Ages 50-65 | | Ages 66+ | |
|---|---|---|---|---|
|  | Hazard Ratio | P-Value | Hazard Ratio | P-Value |
| All-Cause |  |  |  |  |
| Moderate | 2.03 | 0.349 | 0.27 | 0.008 |
| High | 1.30 | 0.722 | 0.30 | 0.040 |
| IGF-I | 1.01 | 0.738 | 0.97 | 0.077 |
| Moderate Protein X IGF-I | 0.99 | 0.809 | 1.03 | 0.088 |
| High Protein x IGF-I | 1.02 | 0.322 | 1.03 | 0.215 |
| CVD |  |  |  |  |
| Moderate | 0.39 | 0.379 | 0.16 | 0.008 |
| High | 0.77 | 0.802 | 0.13 | 0.020 |
| IGF-I | 1.02 | 0.530 | 0.93 | 0.087 |
| Moderate Protein x IGF-I | 1.02 | 0.562 | 1.07 | 0.020 |
| High Protein x IGF-I | 1.01 | 0.708 | 1.07 | 0.031 |
| Cancer |  |  |  |  |
| Moderate | 4.08 | 0.264 | 0.25 | 0.201 |
| High | 1.27 | 0.858 | 0.04 | 0.018 |
| IGF-I | 0.96 | 0.194 | 0.96 | 0.243 |
| Moderate Protein X IGF-I | 1.02 | 0.504 | 1.02 | 0.674 |
| High Protein x IGF-I | 1.09 | 0.026 | 1.06 | 0.153 |

All models included age, sex, race/ethnicity, education, waist circumference, smoking, chronic conditions (diabetes, cancer, MI), trying to lose in last year weight, diet changed in last year, reported intake representative of typical diet, total calories.

Fig. 16

Table 17: Influence of Animal and Vegetable Protein on the Associations between Mortality and Protein intake

| | Hazard Ratio (95% CI) | | | | | |
|---|---|---|---|---|---|---|
| | Ages 50-65 (N=3,039) | | | Ages 66+ (N=3,342) | | |
| | Model 1 | Model 4 | Model 5 | Model 1 | Model 4 | Model 5 |
| All-Cause Mortality | | | | | | |
| Moderate Protein | 1.34 (0.81-2.22) | 1.15 (0.67-1.96) | 1.33 (0.80-2.21) | 0.79 (0.62-0.99) | 0.79 (0.61-1.01) | 0.80 (0.63-1.01) |
| High Protein | 1.74 (1.02-2.97) | 1.18 (0.60-2.31) | 1.73 (0.96-2.96) | 0.72 (0.55-0.94) | 0.72 (0.50-1.02) | 0.73 (0.56-0.96) |
| % kcal Animal Protein | | 1.03 (1.00-1.06) | | | 1.00 (0.98-1.02) | |
| % kcal Vegetable Protein | | | 1.01 (0.96-1.06) | | | 0.98 (0.95-1.01) |
| CVD Mortality | | | | | | |
| Moderate Protein | 0.79 (0.40-1.54) | 0.61 (0.29-1.29) | 0.77 (0.40-1.51) | 0.80 (0.57-1.12) | 0.80 (0.56-1.14) | 0.82 (0.58-1.14) |
| High Protein | 1.03 (0.51-2.09) | 0.55 (0.19-1.62) | 1.02 (0.50-2.06) | 0.78 (0.54-1.14) | 0.77 (0.48-1.25) | 0.79 (0.54-1.16) |
| % kcal Animal Protein | | 1.04 (0.99-1.11) | | | 1.00 (0.98-1.02) | |
| % kcal Vegetable Protein | | | 1.03 (0.96-1.10) | | | 0.98 (0.94-1.02) |
| Cancer Mortality | | | | | | |
| Moderate Protein | 3.06 (1.49-6.25) | 2.71 (1.24-5.91) | 3.03 (1.48-6.19) | 0.67 (0.43-1.06) | 0.66 (0.40-1.07) | 0.68 (0.43-1.09) |
| High Protein | 4.33 (1.96-9.56) | 3.19 (1.21-8.35) | 4.30 (1.93-9.59) | 0.40 (0.23-0.71) | 0.38 (0.17-0.82) | 0.41 (0.23-0.72) |
| % kcal Animal Protein | | 1.02 (0.97-1.07) | | | 1.00 (0.97-1.04) | |
| % kcal Vegetable Protein | | | 1.01 (0.91-1.12) | | | 0.99 (0.92-1.06) |
| Diabetes Mortality | | | | | | |
| Moderate Protein | 3.43 (0.69-17.02) | 2.99 (0.58-15.31) | 3.64 (0.76-17.55) | 5.38 (0.95-30.49) | 6.20 (0.35-37.01) | 5.50 (0.96-31.50) |
| High Protein | 3.93 (0.73-21.07) | 2.77 (0.24-31.73) | 3.97 (0.75-21.11) | 10.64 (1.85-61.31) | 15.16 (1.93-118.9) | 10.71 (1.87-61.28) |
| % kcal Animal Protein | | 1.02 (0.92-1.14) | | | 0.98 (0.90-1.06) | |
| % kcal Vegetable Protein | | | 0.90 (0.75-1.07) | | | 0.98 (0.84-1.14) |

Fig. 17

Table 18: Adjusted mean HbA1c, Diabetes Prevalence, and mean BMI by Age and Protein Intake

| | HbA1c | Diabetes (%) | BMI |
|---|---|---|---|
| Ages 50-65 | | | |
| Low Protein Intake | 5.52 | 2.8 | 27.65 |
| Moderate Protein Intake | 5.65 | 9.8 | 27.93 |
| High Protein Intake | 5.90 | 10.7 | 27.98 |
| P-Value | <.001 | <.001 | .834 |
| Ages 66+ | | | |
| Low Protein Intake | 5.52 | 5.0 | 26.19 |
| Moderate Protein Intake | 5.81 | 13.6 | 26.70 |
| High Protein Intake | 6.03 | 20.4 | 26.50 |
| P-Value | <.001 | <.001 | .401 |

Estimated from models controlling for age, sex, race/ethnicity, education, smoking, diseases, total caloric intake, and dieting

Fig. 18

Table 19: Associations between Diabetes Mortality and Protein Intake, among participants with no diabetes at baseline

|  | Hazard Ratio (95% Confidence Intervals) |
|---|---|
| High Protein (n=930) | 73.52 (4.47-1209.7) |
| Moderate Protein (n=4,441) | 22.93 (1.31-400.7) |

Fig. 19

| | | % Calories of Diet from: | | |
|---|---|---|---|---|
| Diet | Protein | Carbohydrates | Fat | kcal/g |
| AIN93G | 18.8 | 63.9 | 17.2 | 3.8 |
| [a] 20% P-1 | 3.9 | 75.7 | 20.4 | 3.9 |
| [b] 20% P-2 | 3.9 | 75.7 | 20.4 | 3.9 |
| 0% P | 0 | 78.8 | 21.2 | 3.9 |
| LCHP | 45.2 | 13 | 41.8 | 4.4 |
| 60% HF | 9 | 30.9 | 60 | 5.3 |
| 90% HF | 9 | 0.99 | 90.1 | 7.1 |

[a] Soybean oil as fat source
[b] Coconut oil as fat source

Fig. 30

| g/kg diet | AIN93G | 20% P-1 | 20% P-2 | 0% P | LCHP | 60% HF | 90% HF |
|---|---|---|---|---|---|---|---|
| Corn Starch | 397.486 | 487.222 | 487.222 | 511.636 | 85.408 | 179.998 | |
| Dextrinized cornstarch | 132.000 | 161.964 | 161.964 | 170.000 | 28.380 | 170.000 | |
| Sucrose | 100.000 | 122.786 | 122.786 | 128.700 | 21.500 | 56.200 | |
| Casein | 200.000 | 40.000 | 40.000 | | 586.000 | 133.280 | 130 |
| Fat | 70.000 | 87.500 | 87.500 | 92.050 | 198.180 | 350.000 | 759.37 |
| Cellulose | 50.000 | 50.000 | 50.000 | 50.000 | 50.000 | 50.000 | 45 |
| Mineral (AIN-93G-MX) | 35.000 | 35.000 | 35.000 | 35.000 | 35.000 | 35.000 | 35.000 |
| Vitamin (AIN-93-VX) | 10.000 | 10.000 | 10.000 | 10.000 | 10.000 | 10.000 | 10.000 |
| L-Cystine | 3.000 | 3.000 | 3.000 | | 3.000 | 3.000 | 3 |
| Choline bitartrate | 2.500 | 2.500 | 2.500 | 2.500 | 2.500 | 2.500 | 2.500 |
| tert-Butylhydroquinone | 0.014 | 0.014 | 0.014 | 0.014 | 0.014 | 0.014 | 0.130 |
| Calcium-Phosphate | 0.000 | 0.000 | 0.000 | | 0.000 | 0.008 | 0.000 |
| Food Color | | 0.1 | 0.1 | 0.1 | 0.1 | 0.1 | |
| Total (g) | 1000.00 | 1000.00 | 1000.00 | 1000.000 | 1000.00 | 1000.00 | 1000.000 |

Fig. 31

| Diet | NEW | AIN93G | NEW | NEW | AIN93G | AIN93G | AIN93G |
|---|---|---|---|---|---|---|---|
| Day | -7 | -6 | -5 | -4 | -3 | -2 | -1 |
| Mice/cage | 5 | 5 | 5 | 5 | 1 | 1 | 1 |

Fig. 32

| for total diet (kg) | 0.2 | | | | | |
|---|---|---|---|---|---|---|
| | 40% CR | 50% CR | 60% CR | 80% CR | 90%CR | STS |
| AIN-93G (g) | 116.20 | 95.60 | 74.80 | 33.40 | 12.80 | 0.00 |
| Essential FA (ml) | 0.43 | 0.43 | 0.43 | 0.43 | 0.43 | 0.43 |
| Fiber (g) | 4.19 | 5.22 | 6.26 | 8.33 | 9.37 | 10.00 |
| AIN-93G-MX (g) | 2.93 | 3.65 | 4.38 | 5.83 | 6.56 | 7.00 |
| AIN-93-VX (g) | 0.84 | 1.04 | 1.25 | 1.67 | 1.87 | 2.00 |
| Hydrogel (g) | 75.44 | 94.08 | 112.91 | 150.37 | 169.20 | 180.60 |

Fig. 33

| 50% CR diets based on: | | | | | |
|---|---|---|---|---|---|
| | AIN93G | 0% P | LPHC | 60% HF | 90% HF |
| kcal/g | 3.76 | 3.90 | 4.39 | 5.25 | 7.11 |
| Diet (g) | 95.6 | 92.1 | 81.9 | 68.5 | 50.5 |
| Essential FA (ml) | 0.43 | 0.43 | 0.43 | 0.43 | 0.43 |
| Fiber (g) | 5.22 | 5.22 | 5.22 | 5.22 | 5.22 |
| AIN-93G-MX (g) | 3.65 | 3.65 | 3.65 | 3.65 | 3.65 |
| AIN-93-VX (g) | 1.04 | 1.04 | 1.04 | 1.04 | 1.04 |
| Hydrogel (g) | 94.1 | 97.6 | 107.8 | 121.2 | 139.1 |
| Sum (g) | 200 | 200 | 200 | 200 | 200 |

Fig. 34

METHODS AND DIETS FOR LOWERING GLUCOSE AND/OR IGF-1 LEVELS

CROSS REFERENCE TO RELATED APPLICATION

This application claims the benefit of U.S. provisional application Ser. No. 61/763,797 filed Feb. 12, 2013, the disclosure of which is incorporated in its entirety by reference herein.

STATEMENT REGARDING FEDERALLY SPONSORED RESEARCH OR DEVELOPMENT

The invention was made with Government support under Contract No. P01 AG034906-01 awarded by the National Institutes of Health. The Government has certain rights to the invention.

TECHNICAL FIELD

In at least one aspect, the present invention is related to method for alleviating symptoms of age-related illness and chemotoxicity.

BACKGROUND

Caloric restriction (CR) without malnutrition has been consistently shown to increase longevity in a number of animal models, including yeast, C. elegans, and mice. However, the effect of CR on the lifespan of non-human primates remains controversial, and may be heavily influenced by dietary composition. The lifespan extension associated with CR in model organisms is believed to operate through its effects on GH, GHR, leading to subsequent deficiencies in IGF-1 and insulin levels and signaling. The effect of the insulin/IGF-1 pathway on longevity was discovered in C. elegans, by showing that mutations in this pathway, regulated by nutrient availability, caused a two-fold increase in lifespan. Other studies revealed that mutations in orthologs of genes functioning in growth signaling pathways, including Tor-S6K and Ras-cAMP-PKA, promoted aging in multiple model organisms, thus providing evidence for the conserved regulation of aging by pro-growth nutrient signaling genes.

Recently, it has been shown that humans with growth hormone receptor deficiency (GHRD), exhibiting major deficiencies in serum IGF-1 and insulin levels, displayed no cancer mortality, nor diabetes, and despite having a higher prevalence of obesity, combined deaths from cardiac disease and stroke in this group were similar to those in their relatives. Similar protection from cancer was also reported in a study that surveyed 230 GHRDs.

Protein restriction or restriction of particular amino acids, such as methionine and tryptophan, may explain part of the effects of calorie restriction on longevity and disease risk, since protein restriction reduces IGF-1 levels, can increase longevity in mammals independently of calorie intake, and has also been shown to reduce cancer incidence in rodent models.

Accordingly, there is a need for dietary interventions that can alleviate symptoms of age-related illness in both subjects willing to chronically modify their diet and those that would only consider periodic interventions but otherwise continue their normal diet.

SUMMARY OF THE INVENTION

The present invention solves one or more problems of the prior art by providing in at least one embodiment, a method of alleviating a symptom of aging or age related symptoms is provided. The method includes a step in which the subject's average daily protein intake level is determined. In one refinement, the average daily protein intake level is expressed as the percent calories from protein that the subject consumes on average per day. With respect to protein consumption, the relative amounts of protein calories from animal and plant sources are determined. A periodic low protein high nourishment diet in substitution of their normal diet is provided to the subject if the subject's average daily protein intake level is identified as being greater than a predetermined cutoff protein intake level and if the subject is younger than a predetermined age.

In another aspect, a method for lowering glucose and/or IGF-1 levels in a subject is provided. The method includes a step of providing the subject with a periodic low calorie and/or low protein diet having less than about 10 percent calories from plant based protein sources. The subject's glucose and/or IGF-1 levels are monitored to determine whether protein intake should be increased or decreased.

In another aspect, the low protein diet includes a supplement that provides excess levels of non-essential amino acids to be consumed for a period of 5 to 7 days together with very low protein amounts or no protein diet. In a refinement, the low protein diet is alternated with a normal protein diet. In such variations, the low protein plant based diet is provided for 7 days every 2 weeks to 2 months with a normal diet of 1 to 7 weeks in between. Typically, the supplement provides one or more of the following amino acids as a source of nitrogen: alanine, aspartic acid, cysteine, glutamic acid, glycine, histidine, proline, serine, and tyrosine while substantially excluding isoleucine, leucine, lysine, methionine, phenylalanine, threonine, tryptophan, valine, and arginine such that isoleucine, leucine, lysine, methionine, phenylalanine, threonine, tryptophan, valine, and arginine in combination are present in an amount that is less than 5% of a total weight of the subject's diet. In a further refinement, isoleucine, leucine, lysine, methionine, phenylalanine, threonine, tryptophan, valine, and arginine in combination are present in an amount that is less than 3% of a total weight of the subject's diet.

BRIEF DESCRIPTION OF THE DRAWINGS

FIG. 1. Table 9 showing the Calorie overview of the fasting mimicking diet adjusted to human subjects. The fasting mimicking diet (FMD), Prolon, induces a fasting-like response while maximizing nourishment. The consumed calories for each one of the 5 days of the diet are shown, as well as the adjusted kcal per pound and kilogram of body weight. The reduction in calories consumed during the 5 day dietary regimen (Δ5-day) is shown as either 1) based on a 2,000 calorie per day diet, or 2) based on 2,800, 2,400, and 2,000 calorie diets for person's weight≥200, 150-200, and ≤150 lbs, respectively;

FIG. 2. Table 10 showing the defined macronutrient content for each diet day adjusted to a 180-200 lbs human subject. The macronutrient content for each day of the 5 day FMD regimen based on an average 180-200 lbs person. Caloric intake on day 1 of the diet is less reduced compared to the following days (2-5) to allow the body to adjust to the low calorie consumption. % of calories contributed by fat, carbohydrate (by sugar in detail) and protein for each day of the Prolon regimen is presented;

FIG. 3. Table 11 showing the defined micronutrient content for each diet day adjusted to a 180-200 lbs human subject in a variation of the invention. The micronutrient content for each day of the 5 day FMD regimen based on an average 180-200 lbs person. Percent of the daily value (% DV) is calculated based on a 2,000 calorie diet. * for some of the micronutrients, DV is not defined; values shown are based on the reference daily intake (RDI);

FIG. 8. Table 12: Associations between Mortality and Protein intake; Reference=Low Protein (n=437 in both age groups); Model 1: (Baseline Model) Adjusted for age, sex, race/ethnicity, education, waist circumference, smoking, chronic conditions (diabetes, cancer, MI), trying to lose in last year weight, diet changed in last year, reported intake representative of typical diet, total calories; Model 2: Adjusted for Covariates and % kcals from Total Fat Model 3: Adjusted for Covariates and % kcals from Total Carbohydrates; Model 4: Adjusted for Covariates and % kcals from Animal Protein;

FIG. 13. Table 13: Sample Characteristics;

FIG. 14. Table 14: Association between Protein Intake and Mortality (N=6,381); covariates include age, sex, race/ethnicity, education, waist circumference, smoking, chronic conditions (diabetes, cancer, MI), trying to lose in last year weight, diet changed in last year, reported intake representative of typical diet, total calories;

FIG. 15. Table 15: The Influence of IGF-I on the Association between Mortality and Protein Intake (N=2,253); Model 1: (Baseline Model) Adjusted for age, sex, race/ethnicity, education, waist circumference, smoking, chronic conditions (diabetes, cancer, MI), trying to lose in last year weight, diet changed in last year, reported intake representative of typical diet, total calories.
Model 2: Adjusted for Covariates and IGF-I;

FIG. 16. Table 16: Hazard Ratios for the Interaction between Protein and IGF-I on Mortality;

FIG. 17. Table 17: Influence of Animal and Vegetable Protein on the Associations between Mortality and Protein intake; Model 1: (Baseline Model) Adjusted for age, sex, race/ethnicity, education, waist circumference, smoking, chronic conditions (diabetes, cancer, MI), trying to lose in last year weight, diet changed in last year, reported intake representative of typical diet, total calories; Model 4: Adjusted for Covariates and % kcal from Animal Protein; Model 5: Adjusted for Covariates and % kcals from Vegetable Protein; Reference=Low Protein, Ages 50-65: Low Protein (N=219), Moderate Protein (N=2,277), High Protein (N=543), Ages 66+: Low Protein (N=218, Moderate Protein (N=2,521), HIgh Protein (N=603);

FIG. 18. Table 18: Adjusted mean HbAlc, Diabetes Prevalence, and mean BMI by Age and Protein Intake;

FIG. 19. Table 19: Associations between Diabetes Mortality and Protein intake, among participants with no diabetes at baseline; Reference=Low Protein (n=449 in both age groups); Cox Proportional Hazard Model: Adjusted for age, sex, race/ethnicity, education, waist circumference, smoking, other chronic conditions (cancer, MI), trying to lose in last year weight, diet changed in last year, reported intake representative of typical diet, total calories;

FIG. 30. Table 20. Overview about the Macronutrients and calories contained in the Experimental Diets;

FIG. 31. Table 21. Detailed Composition of Macronutrient Defined Diets;

FIG. 32. Table 22. Adjustment Schedule for Macronutrient Defined Diets;

FIG. 33. Table 23. Composition of Calorie Restricted Diets;

FIG. 34. Table 24. Composition of Calorie Restricted Macronutrient Defined Diets.

DETAILED DESCRIPTION

Figure 4:
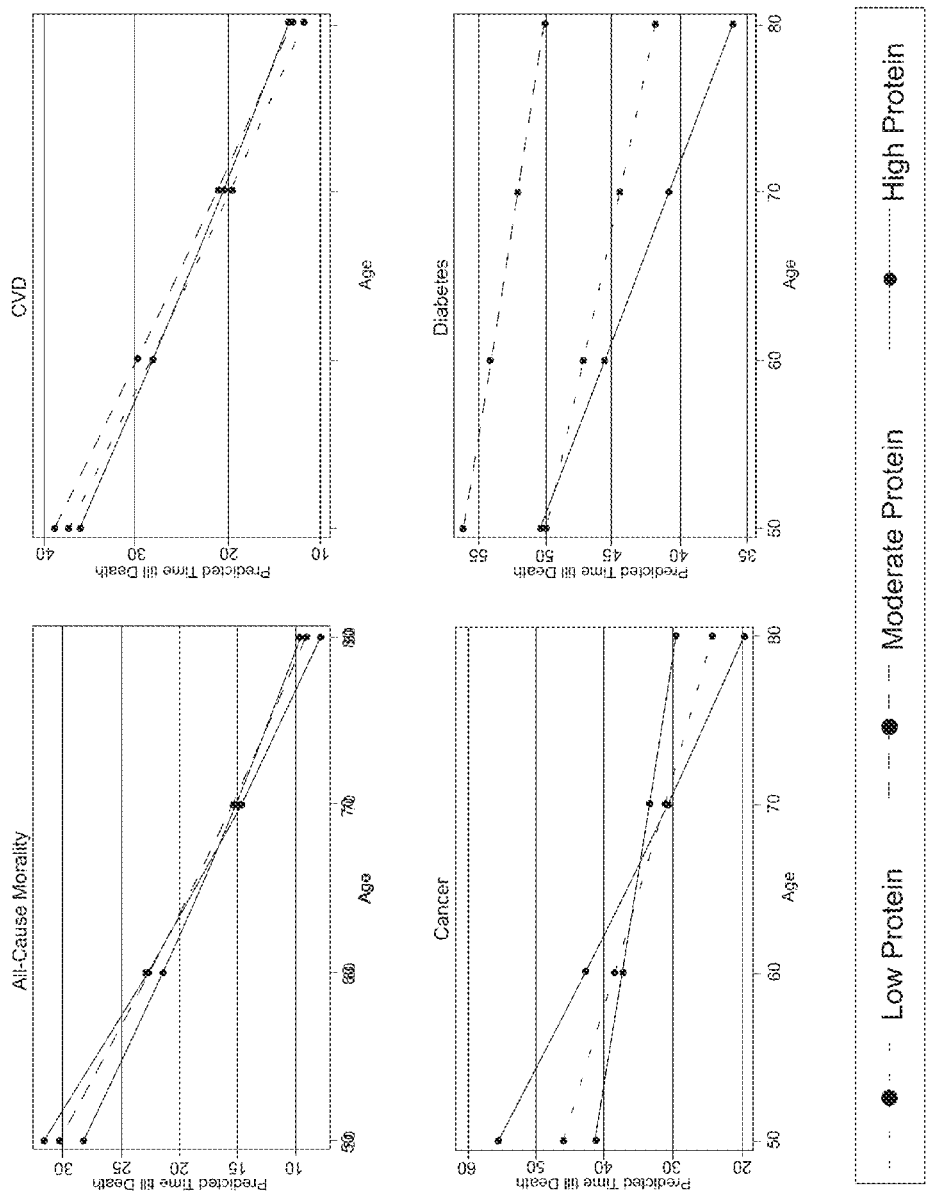
FIG. 4. Using Cox Proportional Hazard Models, statistically significant (p<0.05) interactions between age and protein group were found for all-cause and cancer mortality. Based on these models, predicted remaining life expectancy was calculated for each protein group by age at baseline. Based on results, low protein appears to have a protective effect against all-cause and cancer mortality prior to age 66, at which point it becomes detrimental. No significant interactions were found for cardiovascular disease (CVD) and diabetes mortality.

Reference will now be made in detail to presently preferred compositions, embodiments and methods of the present invention. The Figures are not necessarily to scale. The disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

This invention is not limited to the specific embodiments and methods described below, as specific components and/or conditions may, of course, vary. Furthermore, the terminology used herein is used only for the purpose of describing particular embodiments of the present invention and is not intended to be limiting in any way.

As used in the specification and the appended claims, the singular form "a," "an," and "the" comprise plural referents unless the context clearly indicates otherwise. For example, reference to a component in the singular is intended to comprise a plurality of components.

The term "essential amino acid" refers to amino acids that cannot be synthesized by an organism. In humans, essential amino acids include isoleucine, leucine, lysine, methionine, phenylalanine, threonine, tryptophan, valine. In addition, the following amino acids are also essential in humans under certain conditions—histidine, tyrosine, and selenocysteine.

The terms "kilocalorie" (kcal) and "Calorie" refer to the food calorie. The term "calorie" refers to the so-called small calorie.

The term "subject" refers to a human or animal, including all mammals such as primates (particularly higher primates), sheep, dog, rodents (e.g., mouse or rat), guinea pig, goat, pig, cat, rabbit, and cow.

In an embodiment of the present invention, a method of alleviating a symptom of aging or age related symptoms is provided. For example, the method of the present embodiment may prevent or treat diabetes or cancer, and delays age-related mortality and other age-related diseases. In other variations, the methods are useful for lowering glucose and/or IGF-1 levels in a subject. In still other variations, the methods are useful for treating (e.g., alleviate a symptom of) chemotoxicity in a subject. Typically, the method alleviates one or more symptoms of these conditions. In particular, a method of increasing longevity in a subject is provided. In the present context, increasing longevity means improving a subjects chances of living longer. For example, when many subjects having the same profile (weight, age, glucose levels, insulin level, etc. see below) as the subject are subjected to the methods of the invention, the average survival increases. The method includes a step in which the subject's average daily protein intake level is determined. In one refinement, the average daily protein intake level is expressed as the percent calories from protein that the subject consumes on average per day. The subject's protein intake may be assessed by the subject answer questions or filling out a written survey regarding the subject's daily and weekly protein, fat, and carbohydrate consumption. With respect to protein consumption, the relative amounts of protein calories from animal and plant sources are determined.

A low protein diet is provided to the subject if the subject's average daily protein intake level is identified as being greater than a predetermined cutoff protein intake level and if the subject is younger than a predetermined age. Typically, the predetermined age is from 60 to 70 years. The predetermined age is, in order of increasing preference 60 years, 61 years, 62 years, 63 years, 64 years, 66 years, 67 years, 68 years, 69 years, 70 years, and 65 years, and younger. Characteristically, the low protein diet provides percent calories from protein that is less than the predetermined cutoff protein intake level. Typically, the predetermined cutoff protein intake level is 20% calories from proteins of the total calories consumed on average per day by the subject. In a refinement, the predetermined cutoff protein intake level is 15% calories from proteins of the total calories consumed on average per day by the subject. In a refinement, the predetermined cutoff protein intake level is 10% calories from proteins of the total calories consumed on average per day by the subject. In another refinement, the predetermined cutoff protein intake level is 5% calories from proteins of the total calories consumed on average per day by the subject. In some refinements, the low protein diet provides greater than, in increasing order of preference, 40%, 50%, 60%, 70%, 80%, and 90% calories form protein that are plant sources such as soybeans. Advantageously, the low protein diet provides about 100% calories of protein from plant sources.

The subject's IGF-1 and/or IGFBP1 levels are monitored to determine the frequency and type of diet the subject (e.g., see protein amounts below) should be on and specifically, whether the protein intake should be increased or decreased (i.e., Typically, levels of IGF-I decrease and levels of IGFBP1 increase after the subject is provided with one or more cycles of the low protein diet. In particular, the low protein diet lowers IGF-I by at least 10 percent and/or raises IGFBP1 levels by at least 50% percent. In another refinement, the low protein diet lowers IGF-I by at least 20 percent and/or raises IGFBP1 levels by at least 75%. In another refinement, the low protein diet lowers IGF-I by at least 50 percent and/or raises IGFBP1 levels by at least 2 fold. If the IGF-I decreases and/or IGFBP1 increase is determined to be insufficient, the low protein diet can be adjusted to provide even low amounts of calories from protein sources.

In a variation of the present embodiment, a high protein diet is provided to the subject if the subject's age is older than the predetermined age providing a high protein diet to the subject, the high protein diet having a protein calorie percentage that is greater than the predetermined cutoff protein intake level.

In another variation, the low protein diet is provided to the subject for a predetermined number of days. For example, the low protein diet is provided to the subject for 2 to 10 days. In another refinement, the low protein diet is provided to the subject for 3 to 7 days. In many circumstances, the low protein is periodically provided to the subject. The frequency with which the low protein diet is provided to the subject is determined by the subject's levels of insulin resistance, fasting glucose levels, IGF-I, IGFBP1, obesity, Body Mass Index, weight loss in previous 10 years, family history of cancer, family history of diabetes, family history of early mortality. The frequency can be as high as every month for subjects with high IGF-I levels (example above 200 ng/ml), low levels of IGFBP1 and/or insulin resistance to once every 3 months for subjects with IGF-I between 120 and 200 ng/ml and no insulin resistance.

In a refinement, the low protein diet is a fasting mimicking diet that provides less than 10% of calories from proteins and/or with all proteins being plant-based as set forth in International Pat. Appl. PCT/US13/66236; the entire disclosure of this patent application is hereby incorporated by reference. In particular, the low protein diet is administered for a first time period to the subject. As used herein, sometimes the low protein diet of this embodiment). In a refinement, the low protein diet provides from 4.5 to 7 kilocalories per pound of subject for a first day (day 1) and then 3 to 5 kilocalories per pound of subject per day for a second to fifth day (days 2-5) of the low protein diet. A second diet is administered to the subject for a second time period. In a refinement, the second diet provides an overall calorie consumption that is within 20 percent of a subject's normal calorie consumption for 25 to 26 days (e.g., immediately) following the low protein diet. Characteristically, it is observed that the level of IGF-I decreases and the level of IGFBP1 increases. In a refinement, the method of this embodiment is repeated from 1 to 5 times. In another refinement, the method of this embodiment is repeated from 2 to 3 times. In still another refinement, the method of this embodiment is repeated for a period of years or throughout the subject's entire life with a frequency of every 1 to 3 months depending on the subjects IGF-I and IGFBP1 levels as well as protein intake The frequency can be as high as every month for subjects with high protein intake (above 15% of calories from proteins) and/or high IGF-I levels (example above 200 ng/ml), and low levels of IGFBP1 and/or insulin resistance to once every 3 months for subjects with protein intake representing between 10-15% of calories, IGF-I levels between 120 and 200 ng/ml, and no insulin resistance.

In another refinement, the combination of the low protein diet and the second diet (e.g., the subject's normal diet and caloric intake) provide the subject with a total number of calories within 10 percent of the subject's normal caloric intake. In another refinement, the combination of the low protein diet and the second diet provides the subject with a total number of calories within 5 percent of the subject's normal caloric intake. In still another refinement, the combination of the low protein diet and the second diet provides the subject with a total number of calories within 1 percent of the subject's normal caloric intake.

In a refinement, the fasting mimicking diet (FMD) involves completely substituting a subject's diet for 5 days. During this 5 day period, subjects consume plenty of water. For healthy subjects of normal weight (Body Mass Index or BMI between 18.5-25), the diet is consumed once a month (5 days on the diet and 25-26 days on their normal diet) for the first 3 months and every 3 months thereafter (5 days every 3 months). The weight of the subject is measured and the subject must regain at least 95% of the weight lost during the diet before the next cycle is begun. Subjects with BMI of less than 18.5 should not undertake the FMD unless recommended and supervised by a physician. The same regimen (once every month for 3 months followed by once every 3 months thereafter) can be adopted for the treatment, or in support of the treatment, of all of the conditions presented in the patent applications.

The consumption guidelines for the FMD include Nutrition Facts relative to calories, macronutrients and micronutrients. Calories are consumed according to the user's body weight. Total calorie consumption is 4.5-7 calorie per pound (or 10-16 calorie per kilogram) for day 1 and 3-5 calorie per pound (or 7-11 calorie per kilogram) for day 2 to 5. FIGS. 1-3 provides listings of the nutrients for day one through day five. In addition to the macronutrients, the diet should contain less than 30 g of sugar on day 1 and less than 20 g of sugar on days 2-5. The diet should contain less than 28 g of proteins on day 1 and less than 18 g of proteins on days 2-5, mostly or completely from plant based sources. The diet should contain between 20 and 30 grams of monounsaturated fats on day 1 and 10-15 grams of monounsaturated fats on days 2-5. The diet should contain between 6 and 10 grams of polyunsaturated fats on day 1 and 3-5 grams of polyunsaturated fats on days 2-5. The diet should contain less than 12 g of saturated fats on day 1 and less than 6 grams of saturated fats on days 2-5. Typically, the fats on all days are derived from a combination of the following: Almonds, Macadamia Nuts, Pecans, Coconut, Coconut oil, Olive Oil and Flaxseed. In a refinement, the FMD diet includes over 50% of the recommended daily value of dietary fiber on all days. In the further refinement, the amount of dietary fiber is greater than 15 grams per day on all five days. The diet should contain 12-25 grams of glycerol per day on days 2-5. In a refinement, glycerol is provided at 0.1 grams per pound body weight/day.

In a variation, the FMD includes the following micronutrients (at least 95% non-animal based): over 5,000 IU of vitamin A per day (days 1-5); 60-240 mg of vitamin C per day (days 1-5); 400-800 mg of Calcium per day (days 1-5); 7.2-

14.4 mg of Iron per day (days 1-5); 200-400 mg of Magnesium per day (days 1-5); 1-2 mg of copper per day (days 1-5); 1-2 mg of Manganese per day (days 1-5); 3.5-7 mcg of Selenium per day (days 1-5); 2-4 mg of Vitamin B1 per day (days 1-5); 2-4 mg of Vitamin B2 per day (days 1-5); 20-30 mg of Vitamin B3 per day (days 1-5); 1-1.5 mg of Vitamin B5 per day (days 1-5); 2-4 mg of Vitamin B6 per day (days 1-5); 240-480 mcg of Vitamin B9 per day (days 1-5); 600-1000 IU of Vitamin D per day (days 1-5); 14-30 mg of Vitamin E per day (days 1-5); over 80 mcg of Vitamin K per day (days 1-5); 16-25 mcg Vitamin B12 are provided during the entire 5-day period; 600 mg of Docosahexaenoic acid (DHA, algae-derived) are provided during the entire 5-day period. The FMD diet provides high micronutrient content mostly (i.e., greater than 50 percent by weight) from natural sources including: Kale, Cashews, Yellow Bell Pepper, Onion, Lemon Juice, Yeast, Turmeric. Mushroom, Carrot, Olive Oil, Beet Juice, Spinach, Tomato, Collard, Nettle, Thyme, Salt, Pepper, Vitamin B12 (Cyanocobalamin), Beets, Butternut Squash, Collard, Tomato, Oregano, Tomato Juice, Orange Juice, Celery, Romaine Lettuce, Spinach, Cumin, Orange Rind, Citric Acid, Nutmeg, Cloves, and combinations thereof. Table 1 provides an example of additional micronutrient supplementation that can be provided in the FMD diet:

TABLE 1

Micronutrient Supplementation

|  | Supplement | Formula | Amount | Amount Range | Unit |
|---|---|---|---|---|---|
| Vit A |  |  | 1250 IU | 900-1600 | IU |
| Vit C | Ascorbic Acid | $C_6H_8O_6$ | 15.0000 | 10-20 | mg |
| Ca | Calcium Carbonate | $CaCO_3$ | 80.0000 | 60-100 | mg |
| Fe | Ferrous Fumarate | $C_4H_2FeO_4$ | 4.5000 | 3-6 | mg |
| Vit D3 | Cholecalciferol | $C_{27}H_{44}O$ | 0.0025 | 0.001-0.005 | mg |
| Vit E | dl-Alpha Tocopheryl Acetate | $C_{29}H_{50}O_2$ | 5.0000 | 3-7 | mg |
| Vit K | Phytonadione |  | 0.0200 | 0.1-0.04 | mg |
| Vit B1 | Thiamine Mononitrate | $C_{12}H_{17}N_5O_4S$ | 0.3750 | 0.15-0.5 | mg |
| Vit B2 | Riboflavin E101 | $C_{17}H_{20}N_4O_6$ | 0.4250 | 0.2-0.6 | mg |
| Vit B3 | Niacinamide | $C_6H_6N_2O$ | 5.0000 | 3-7 | mg |
| Vit B5 | Calcium Pantothenate | $C_{18}H_{32}CaN_2O_{10}$ | 2.5000 | 1.5-4.0 | mg |
| Vit B6 | Pyridoxine Hydrochloride | $C_8H_{11}NO_3 \cdot HCl$ | 0.5000 | 0.3-0.7 | mg |
| Vit B7 | Biotin | $C_{10}H_{16}N_2O_3S$ | 0.0150 | 0.01-0.02 | mg |
| Vit B9 | Folic Acid | $C_{19}H_{19}N_7O_6$ | 0.1000 | 0.07-0.14 | mg |
| Vit B12 | Cyanocobalamin | $C_{63}H_{88}CoN_{14}O_{14}P$ | 0.0015 | 0.001-0.002 | mg |
| Cr | Chromium Picolinate | $Cr(C6H4NO2)3$ | 0.0174 | 0.014-0.022 | mg |
| Cu | Cupric Sulfate | $CuSO4$ | 0.2500 | 0.18-0.32 | mg |
| I | Potassium Iodide | KI | 0.0375 | 0.03-0.045 | mg |
| Mg | Magnesium Oxide | MgO | 26.0000 | 20-32 | mg |
| Mn | Manganese Sulfate | $MnSO_4$ | 0.5000 | 0.3-0.7 | mg |
| Mo | Sodium Molybdate | $Na_2MoO_4$ | 0.0188 | 0.014-0.023 | mg |
| Se | Sodium Selenate | $Na_2O_4Se$ | 0.0175 | 0.014-0.023 | mg |
| Zn | Zinc Oxide | ZnO | 3.7500 | 3-5 | mg |

In another embodiment, a diet package for implemented the diet protocol set forth above is provided. The diet package includes a first set of rations for a low protein diet to be administered for a first time period to a subject, the low protein diet providing from 4.5 to 7 kilocalories per pound of subject for a first day and 3 to 5 kilocalories per pound of subject per day for a second to fifth day of the low protein diet. The diet package includes rations that provide less than 30 g of sugar on the first day; less than 20 g of sugar on the second to fifth days; less than 28 g of proteins on the first day; less than 18 g of proteins on days the second to fifth days; 20 to 30 grams of monounsaturated fats on the first day; 10 to 15 grams of monounsaturated fats on the second to fifth days; between 6 and 10 grams of polyunsaturated fats on the first day; 3 to 5 grams of polyunsaturated fats on the second to fifth days; less than 12 g of saturated fats on the first day; less than 6 grams of saturated fats on the second to fifth days; and 12 to 25 grams of glycerol per day on the second to fifth days. In a refinement, the diet package further includes sufficient rations to provide the micronutrients set forth above. In a further refinement, the diet package provides instructions providing details of the methods set forth above.

In refinement of the embodiments set forth above, a 5-day supply of diet includes: soups/broths, soft drinks, nut bars and supplements. The diet is administered as follows: 1) on the first day a 1000-1200 kcal diet with high micronutrient nourishment is provided; 2) for the next 4 days a daily diet of 650-800 kcal plus a drink containing a glucose substitution carbon source (glycerol or equivalent) providing between 60-120 kcal are provided. The substitution carbon source does not interfere with the effect of fasting on stem cell activation.

In another refinement of the embodiments set forth above, a 6-day low-protein diet protocol includes: soups/broths, soft drinks, nut bars, and supplements. The diet is administered as follows: 1) on the first day a 1000-1200 kcal diet plus with high micronutrient nourishment is provided; 2) for the next 3 days a daily diet of less than 200 kcal plus a drink containing a glucose substitution carbon source providing between 60 and 120 kcal. This substitution carbon source, including glycerol, does not interfere with the effect of fasting on stem cell activation; 3) on the 5th day the subject consumes a normal diet; and 4) on day 6 an additional replenishment foods consisting of a high fat source of 300 kcal and a micronutrient nourishment mix on day 6 replenishment foods consisting of a high fat source of 300 kcal and a micronutrient nourishment mix are provided in addition to normal diet.

In still another refinement, a diet protocol includes: 6-day supply of low-protein diet includes: soups/broths, soft drinks, nut bars, and supplements. 1) on the first day a 1000-1200 kcal diet with high micronutrient nourishment is provided; 2) for the next 3 days a daily diet of 600 to 800 kcal which contains less than 10 grams of protein and less than 200 kcal from sugars; 3) on the 5th day the subject receives a normal diet; and 4) on day 6 an additional replenishment foods consisting of a high fat source of 300 kcal and a micronutrient nourishment mix on day 6 replenishment foods consisting of a high fat source of 300 kcal and a micronutrient nourishment mix are provided in addition to normal diet.

A particularly useful diet protocol and dietary packages are provided by WIPO Pub. No. WO2011/050302 and the dietary protocols herein. WIPO Pub. No. WO2011/050302 is hereby incorporated in its entirety by reference. In particular, subjects are provided with a low protein diet for a first time period, a second diet for a second time period, and an optional third diet for a third time period. The low protein diet provides the subject with at most 50% of the subject's normal caloric intake with at least 50% of the kilocalories being derived from fat, preferably monounsaturated fats. The subject's normal caloric intake is the number of kcal that the subject consumes to maintain his/her weight. The subject's normal caloric intake may be estimated by interviewing the subject or by consideration of a subject's weight. As a rough guide, subject's normal caloric intake is on average 2600 kcal/day for men and 1850 kcal/day for women. In certain instances, the low protein diet provides the subject with from 700 to 1200 kcal/day. In a particularly useful refinement, the low protein diet provides the male subject of average weight with about 1100 kcal/day and the female subject of average weight with 900 kcal/day. Typically, the first predetermined period of time is from about 1 to 5 days. In certain instances, the first predetermined period of time is 1 day. In order to put the level of fat in the low protein diet in perspective, the U.S. Food and Drug Administration recommends the following nutritional breakdown for a typical 2000 kilocalorie a day diet: 65 gram fat (about 585 kilocalories), 50 grams protein (about 200 kilocalories), 300 grams total carbohydrates (about 1200 kilocalories). Therefore, in one version of the low protein diet, a majority of the calories from carbohydrates and proteins are eliminated.

Although the low protein diet encompasses virtually any source of fat, sources high in unsaturated fat, including monounsaturated and polyunsaturated fat sources, are particularly useful (e.g., omega-3/6 essential fatty acids). Suitable examples of monounsaturated food sources include, but are not limited to, peanut butter, olives, nuts (e.g., almonds, pecans, pistachios, cashews), avocado, seeds (e.g., sesame), oils (e.g., olive, sesame, peanut, canola), etc. Suitable examples of polyunsaturated food sources include, but are not limited to, walnuts, seeds (e.g., pumpkin, sunflower), flaxseed, fish (e.g., salmon, tuna, mackerel), oils (e.g., safflower, soybean, corn). The low protein diet also includes a component selected from the group consisting of vegetable extracts, minerals, omega-3/6 essential fatty acids, and combinations thereof. In one refinement, such a vegetable extract provides the equivalent of 5 recommended daily servings of vegetables. Suitable sources for the vegetable extract include, but are not limited to, bokchoy, kale, lettuce, asparagus, carrot, butternut squash, alfalfa, green peas, tomato, cabbage, cauliflower, beets. Suitable sources for the omega-3/6 essential fatty acids include fish such as salmon, tuna, mackerel, bluefish, swordfish, and the like. In a further refinement, the low protein diet includes fat sources such that at least 25 percent of calories from fat are short-chain fatty acids having from 2 to 7 carbon atoms and/or from medium-chain saturated fatty acids having from 8 to 12 carbon atoms. Specific examples of fatty acids include lauric and/or myristic acid and fat sources include olive oil, kernel oil and/or coconut oil. In other refinement, wherein the low protein diet includes calories from fat in an amount from about 0 to 22 percent of total calories contained in the diet.

In a refinement, the subject is then provided the second diet for a second time period. The second diet provides the subject with at most 900 kcal/day. In certain instances, the second diet provides the subject with at most 200 kcal/day. Typically, the second predetermined period of time is from about 2 to 7 days. In certain particular instances, the second predetermined period of time is 3 days. In still another refinement, the second diet includes a component selected from the group consisting of vegetable extracts, minerals, omega-3/6 essential fatty acids, and combinations thereof. In one refinement, such a vegetable extract provides the equivalent of 5 recommended daily servings of vegetable. Suitable sources for the vegetable extract include, but are not limited to, bokchoy, kale, lettuce, asparagus, carrot, butternut squash, alfalfa, green peas, tomato, cabbage, cauliflower, beets. Suitable sources for the omega-3/6 essential fatty acids include fish oils from salmon, tuna, mackerel, bluefish, swordfish, and the like.

The effectiveness of the dietary protocols herein is monitored by measurement of a number of subject parameters. For example, it is desirable that the subject's serum concentration of IGF-I be reduced by 25-90% by the end of the second diet period, depending on the initial IGF-I and protein intake level and on the levels optimal for protection against mortality described in the attached publications. It is also desirable that the blood glucose concentration in the subject be reduced by 25-75% by the end of the second diet period.

In another variation of the present embodiment, the low protein diet includes amino acid specific supplement having certain amino acids. Typically, the supplement provides excess levels of non-essential amino acids to be consumed for a period of 5 to 7 days together with very low protein amounts or no protein diet. In a refinement, the low protein diet is alternated with a normal protein diet. In such variations, the low protein diet is provided for 7 days every 2 weeks to 2 months with a normal diet of 1 to 7 weeks in between. In a refinement, the amino acid specific supplement substantially excludes the following amino acids isoleucine, leucine, lysine, methionine, phenylalanine, threonine, tryptophan, valine, and arginine. In this context, "substantially excludes" means that the total of the excluded amino acids is less than, increasing order of preference, 5 weight percent, 3 weight percent, 1 weight percent, and 0.5 weight percent of the total weight of the subject's diet. Instead, the amino acid specific diet provides one or more of the following amino acids as a source of nitrogen: alanine, aspartic acid, cysteine, glutamic acid, glycine, histidine, proline, serine, and tyrosine. Tables 2 to 4 provide characteristics of an amino acid specific diet for a mouse which is also a protein restricted as set forth below. A typical mouse diet provides about 19 kcal per day. For other mammals such as humans, the protein restricted (PR) diet is scaled to provide the requisite calories. For example, a typical caloric intake for adults in the United States is about 2200 calories per day. Table 5 provides the kilocalories per day from each source for human subjects while Table 6 provides the grams per day from each source for humans.

TABLE 2

| | Normal Diet | PR diet |
|---|---|---|
| Ingredients (g/kg) | | |
| Corn Starch | 397.49 | 397.49 |
| Maltodextrin | 132 | 149.88 |
| Sucrose | 100 | 100 |
| Soybean Oil | 70 | 72 |
| Cellulose | 50 | 50 |
| Mineral | 35 | 35 |
| Vitamin | 10 | 10 |
| Choline Bitartarate | 2.5 | 2.5 |
| Tert-butylhydroquinone | 0.01 | .01 |
| Macronutrients (g/kg) | | |
| Carbohydrate | 601 | 617 |
| Nitrogen Source | 177 | 183 |
| Fat | 72 | 72 |
| Caloric density (kcal/g) | | |
| | 3.7600 | 3.7673 |

TABLE 3

Kilocalories in 1 kg of mouse from each food source.

| | NORMAL DIET | PR |
|---|---|---|
| Carbohydrate | 2404 | 2468 |
| Nitrogen Source | 708 | 732 |
| Fat | 648 | 648 |
| calculated | 3760 | 3848 |

TABLE 4

Percent calories from each source (mouse).

| | NORMAL DIET | PR |
|---|---|---|
| Carbohydrate | 63.94 | 64.14 |
| Nitrogen Source | 18.83 | 19.02 |
| Fat | 17.23 | 16.84 |

TABLE 5

Calories per day from each source (Humans).

| | NORMAL DIET | PR |
|---|---|---|
| Carbohydrate | 1406.60 | 1411.02 |
| Nitrogen Source | 414.26 | 418.50 |
| Fat | 379.15 | 370.48 |
| Total (kcal) | 2200.00 | 2200.00 |

TABLE 6

Grams per day from each source (Humans).

| | NORMAL DIET | PR |
|---|---|---|
| Carbohydrate | 351.65 | 352.75 |
| Nitrogen Source | 103.56 | 104.63 |
| Fat | 42.13 | 41.16 |
| Total (g) | 497.34 | 498.54 |

In a refinement, a kilogram of the amino acid specific diet for a mouse includes from about 2 g to 20 g alanine, 10 g to 30 g aspartic acid, 2 g to 20 g cysteine, 40 g to 80 g glutamic acid, 2 g to 20 g glycine, 2 g to 20 g histidine, 15 g to 50 g proline, 5 g to 30 g serine, and 5 to 30 g tyrosine. For human subjects, these ranges are multiplied by a factor (i.e., about 0.572) to provide the composition of the dietary formulation per day for human subjects. For example, the daily amounts of the specified amino acids for humans (2200 Calorie/day diet) in the amino acid specific diet are about 2 to 12 g alanine, 5 g to 30 g aspartic acid, 1 g to 7 g cysteine, 18 g to 73 g glutamic acid, 2 g to 9 g glycine, 2 g to 10 g histidine, 9 g to 37 g proline, 5 g to 21 g serine, and 5 to 21 g tyrosine. In another refinement, the amino acid specific diet includes from about 160 to about 240 g of the specified amino acids per kilogram of the diet. Therefore, for humans the amino acid specific diet provides from about 80 to 160 g of the specified amino acids per day using a factor (0.572) to convert the per kilogram of diet value to a value representative of a human diet of about 2200 Calories/day. In another variation, the amino acid specific diet includes at least 6 amino acids selected from the group consisting of alanine, aspartic acid, cysteine, glutamic acid, glycine, histidine, proline, serine, and tyrosine in the amounts set forth above. In still another variation, the amino acid specific diet provides the amounts of amino acids in grams per Kg of human body weight per day set forth in Table 7. In particular, the amino acid specific diet provided the following grams per Kg of human body weight per day 0.06 g alanine, 0.14 g aspartic acid, 0.04 g cysteine, 0.45 g glutamic acid, 0.05 g glycine, 0.06 g histidine, 0.23 g proline, 0.13 serine, and 0.13 g tyrosine. In another refinement, each of these amino acids is within a range of plus or minus 30 percent of the specified value.

TABLE 7

Human levels. Grams of each amino acid selected for the dementia protecting diet per Kg of human body weight per day.
Formulation grams/kg Body Weight

| AA | NORMAL DIET | PR | Factor |
|---|---|---|---|
| Ala | 0.07 | 0.06 | 0.81 |
| Asp | 0.13 | 0.14 | 1.09 |
| Cys | 0.02 | 0.04 | 2.05 |
| Glu | 0.20 | 0.45 | 2.23 |
| Gly | 0.06 | 0.05 | 0.94 |
| His | 0.04 | 0.06 | 1.68 |
| Pro | 0.10 | 0.23 | 2.25 |
| Ser | 0.09 | 0.13 | 1.35 |
| Tyr | 0.06 | 0.13 | 2.19 |
| Total | 0.78 | 1.30 | |

In another variation, the method includes a step of administering a protein restricted (PR) diet to a subject for a first time period. In a variation, the low protein diet includes a dietary supplement of specific amino acids. In a refinement, the first time period is from about 5 days to 14 day with 7 days being typical. Moreover, the low protein diet provides the subject with from 70 to 100 percent of the subject's normal caloric intake. The low protein diet includes substantially only amino acids as a source of nitrogen. For example, the protein restricted diet derives less than 10 percent of its calories from proteins. In another refinement, the protein restricted diet derives less than 5 percent of its calories from proteins. In another refinement, the protein restricted diet derives zero percent of its calories from proteins. In particular, the protein restricted diet substantially excludes the following amino acids isoleucine, leucine, lysine, methionine, phenylalanine, threonine, tryptophan, valine, and arginine. In this context, "substantially excludes" means that the total of the excluded amino acids is less than, increasing order of preference, 5 weight percent, 3 weight percent, 1 weight percent, and 0.5 weight percent. Instead, the protein restricted diet provides one or more of the following amino acids as a source of nitrogen: alanine, aspartic acid, cysteine, glutamic acid, glycine, histidine, proline, serine, and tyrosine. Tables 2 to 4 provide characteristics a protein restricted diet including the dietary supplement for the mouse studies that are set forth below. A typical mouse diet provides about 19 kcal per day. For other mammals such as humans, the low protein diet is scaled to provide the requisite calories. For example, a typical caloric intake for adults in the United States is about 2200 kcalories per day. Table 5 provides the kilocalories per day from each source for human subjects while Table 6 provides the grams per day from each source for humans.

In a refinement, the amino acids in a kilogram of the low protein diet for a mouse are provided in Table 8. In a refinement, a kilogram of the low protein diet for a mouse includes from about 2 g to 20 g alanine, 10 g to 30 g aspartic acid, 2 g to 20 g cysteine, 40 g to 80 g glutamic acid, 2 g to 20 g glycine, 2 g to 20 g histidine, 15 g to 50 g proline, 5 g to 30 g serine, and 5 to 30 g tyrosine. For human subjects, these ranges are multiplied by a factor (i.e., about 0.572) to provide the daily requirements for these amino acids per day for human subjects. For example, the daily amounts of the specified amino acids for humans (2200 Calorie/day diet) in the low protein diet are about 2 to 12 g alanine, 5 g to 30 g aspartic acid, 1 g to 7 g cysteine, 18 g to 73 g glutamic acid, 2 g to 9 g glycine, 2 g to 10 g histidine, 9 g to 37 g proline, 5 g to 21 g serine, and 5 to 21 g tyrosine. In another refinement, the protein restricted diet includes from about 160 to about 240 g of the specified amino acids per kilogram of the diet. Therefore, for humans the low protein diet provides from about 80 to 160 g of the specified amino acids per day using a factor (0.572) to convert the per kilogram of diet value to a value representative of a human diet of about 2200 Calories/day. In another variation, the protein restricted diet includes at least 6 amino acids selected from the group consisting of alanine, aspartic acid, cysteine, glutamic acid, glycine, histidine, proline, serine, and tyrosine in the amounts set forth above. Table 8 provides an example of the amino acid content in the protein restricted diet for a mouse diet. Table 8 also provides a factor which is the ratio of a specified amino acid in the protein restricted diet to that of the control (normal diet). These ratios are equally applicable to other mammals such as human subjects. In still another variation, the low protein diet provides the amounts of amino acids in grams per Kg of human body weight per day set forth in table 8. In particular, the PK diet provided the following grams per Kg of human body weight per day 0.06 g alanine, 0.14 g aspartic acid, 0.04 g cysteine, 0.45 g glutamic acid, 0.05 g glycine, 0.06 g histidine, 0.23 g proline, 0.13 serine, and 0.13 g tyrosine. In another refinement, each of these amino acids is within a range of plus or minus 30 percent of the specified value.

In another variation, a method for lowering glucose and/or IGF-1 levels in a subject is provided. The method includes a step of providing the subject with a low protein diet having less than about 10 percent calories from protein sources. The subject's glucose and/or IGF-1 levels are monitored to determine whether protein intake should be increased or decreased. In a refinement, the low protein diet has from 0 to 10 percent calories from protein sources. In a further refinement, the low protein diet has from 0 to 5 percent calories from protein sources. In another refinement, the low protein diet typically has about 0 percent calories from protein sources. In another refinement, the low protein diet is also a low calorie diet which includes fat sources such that at least 50 percent of calories from fat are from long-chain unsaturated fatty acids as set forth above having from 13 to 28 carbon atoms. Typical fat sources include vegetable oil such as soybean oil. In a further refinement, the low protein diet includes fat sources such that at least 25 percent of calories from fat are short-chain fatty acids having from 2 to 7 carbon atoms and/or from medium-chain saturated fatty acids having from 8 to 12 carbon atoms. Specific examples of fatty acids include lauric and/or myristic acid and fat sources include olive oil, kernel oil and/or coconut oil. In other refinement, wherein the low protein diet includes calories from fat in an amount from about 0 to 22 percent of total calories contained in the diet.

In another embodiment, a method for alleviating a symptom of chemotoxicity in a subject is provided. The method includes a step of providing a low protein diet for a first time period, the low protein diet including less than 10 percent calories from protein. A calorie restricted diet is provided to the subject for a second time period, the calorie restricted diet having 0 to 50% of the calories of the low protein diet. In a refinement, the calorie restricted diet include from 0 to 10% calories from protein sources. In a refinement, a chemotherapeutic treatment is administered to the subject. Examples of chemotherapeutic agents include, but are not limited to, doxorubicin, cyclophosphamide, cisplatin, 5-fluorouracil and combinations thereof.

The following examples illustrate the various embodiments of the present invention. Those skilled in the art will recognize many variations that are within the spirit of the present invention and scope of the claims.

Low Protein Intake Experiments

An epidemiological study of 6,381 US men and women aged 50 and above from NHANES were combined, the only nationally-representative dietary survey in the U.S., with mouse and cellular studies to understand the link between the level and source of proteins and amino acids, aging, diseases, and mortality.

Results

Human Population

The study population included 6,381 adults ages 50 and over from NHANES III, a nationally representative, cross-sectional study. Our analytic sample had a mean age of 65 years and is representative of the U.S. population in ethnicity, education, and health characteristics (Table 13).

On average, subjects consumed 1,823 calories, of which the majority came from carbohydrates (51%), followed by fat (33%), and protein (16%)—with 11% from animal protein. The percent calories from protein was used to categorize subjects into a high protein group (20% or more of calories from proteins), a moderate protein group (10-19% of calories from proteins), and a low protein group (less than 10% of calories from proteins).

Mortality follow-up was available for all NHANES participants through linkage with the National Death Index up until 2006 (22). This provided the timing and cause of death. The follow up period for mortality covered 83,308 total person-years over 18 years, with 40% overall mortality, 19% cardiovascular disease (CVD) mortality, 10% cancer mortality, and about 1% diabetes-caused mortality.

Association Between Protein and Mortality

Using Cox Proportional Hazard models we found that high and moderate protein consumption were positively associated with diabetes-related mortality, but not associated with all-cause, CVD, or cancer mortality when all the subjects above age 50 were considered. Results showed that both the moderate and high protein intake groups had higher risks of diabetes mortality, compared to participants in the low protein group. Although taken together these results indicate that moderate to high protein intake promote diabetes mortality, larger studies are necessary to test this possibility further. An alternative explanation for the elevated diabetes mortality in the higher protein group is the possibility that, following a diabetes diagnosis, individuals may switch to a diet comprised of higher protein, lower fat, and low carbohydrate intake. To test this, we examined the association between protein intake and diabetes mortality in participants who had no prevalence of diabetes at baseline (Table 19).

Among subjects with not diabetes at baseline those in the high protein group had a 73-fold increase in risk (HR: 73.52; 95% CI: 4.47-1209.7), while those in the moderate protein category had an almost 23-fold increase in the risk of diabetes mortality (HR: 22.93; 95% CI: 1.31-400.7). We underline that our hazard ratios and confidence intervals may be inflated due to our sample size and the extremely low incidence of diabetes mortality in the low protein group. Overall, there were only 21 diabetes deaths among persons without diabetes at baseline—only 1 of which were from the low protein group. Nevertheless, despite the small sample size, our results still show strong significant associations between increased protein intake and diabetes-related mortality.

Cox Proportional Hazard models were rerun testing for an interaction between protein consumption and age, to determine whether the association between protein and mortality differed for middle-aged and older adults. Significant interactions were found for both all-cause and cancer mortality, showing that low protein was beneficial in mid-life; however, its benefits declined with age (FIG. 4). Based on these results, we stratified the population into two age groups—those ages 50-65 (n=3,039), and those ages 66+ (n=3,342) and reexamined relationships between protein and cause-specific mortality. Among those aged 50-65, higher protein levels were linked to significantly increased risks of all-cause and cancer mortality (Table 12). In this age range, subjects in the high protein group had a 74% increase in their relative risk of all-cause mortality (HR: 1.74; 95% CI: 1.02-2.97), and were more than 4-times as likely to die of cancer (HR: 4.33; 95% CI: 1.96-9.56) when compared to those in the low protein group. None of these associations were significantly affected by controlling for percent calories from total fat or for percent calories from total carbohydrates. However, when the percent calories from animal protein was controlled for, the association between total protein and all-cause and cancer mortality was eliminated or significantly reduced, respectively, suggesting animal protein mediates a significant portion of these relationships. If we control for the effect of plant-based protein, there is no change in the association between protein intake and mortality, indicating that high levels of animal proteins promote mortality and not that plant-based proteins have a protective effect (Table 17).

Compared to subjects with a low protein diet, subjects who consumed moderate levels of protein also had a 3-fold higher cancer mortality (HR: 3.06; 95% CI: 1.49-6.25), that was not accounted for by either percent calories from fat or percent calories from carbohydrates, but was marginally reduced when controlling for percent calories from animal protein (HR: 2.71; 95% CI: 1.24-5.91). Although the size of the effect was not as large as for those in the high protein group. Taken together, these results indicate that respondents aged 50-65 consuming high levels of animal protein display a major increase in the risks for overall and cancer mortality, however, the risks may be somewhat decreased if protein does not come from an animal source. Similar results were obtained if the population 45-65 was considered (data not shown)

In contrast to the findings above, among respondents who were 66 years of age and over at baseline, higher protein levels were associated with the opposite effect on overall and cancer mortality but a similar effect on diabetes mortality (Table 12). When compared to those with low protein consumption, subjects who consumed high amounts of protein had a 28% reduction in all-cause mortality (HR: 0.72; 95% CI: 0.55-0.94), while subjects who consumed moderate amounts of protein displayed a 21% reduction in all-cause mortality (HR: 0.78; 95% CI: 0.62-0.99). Furthermore, this was not affected by percent calories from fat, from carbohydrates, or from animal protein. Subjects with high protein consumption also had a 60% reduction in cancer mortality (HR: 0.40; 95% CI: 0.23-0.71) compared to those with low protein diets, which was also not affected when controlling for other nutrient intake or protein source.

The Influence of IGF-1 on the Association Between Protein and Mortality

Figure 5:
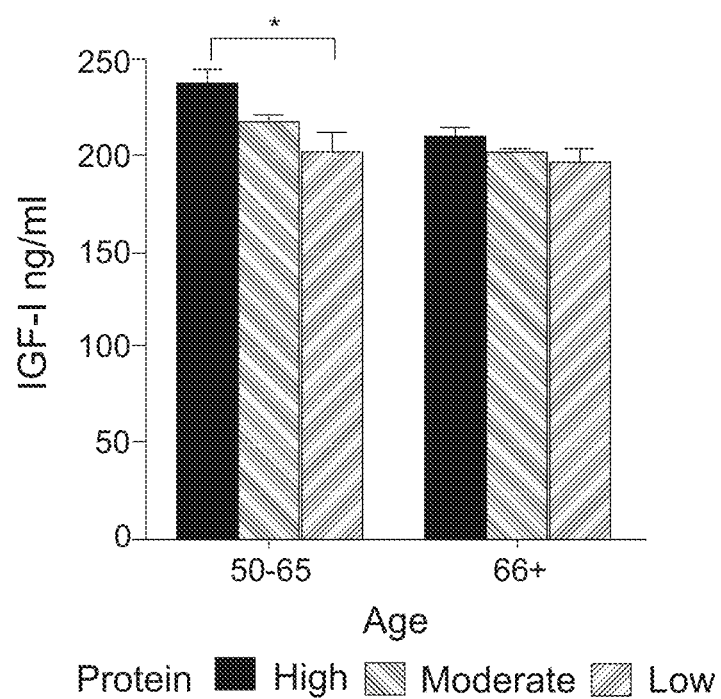
FIG. 5. Serum IGF-1 levels in respondents 50-65 and 66+ reporting low, moderate, or high protein intake. IGF-1 in respondents 50-65 is significantly lower among those with low protein intake when compared to high (P=0.004). At age 66+ the difference between high and low intake becomes marginally significant (P=0.101). The cohort for which IGF-1 levels were calculated includes 2253 subjects. Of those ages 50-65 (n=1,125), 89 were in the low protein category, 854 were in the moderate protein category, and 182 were in the high protein category. Of those ages 66+ (n=1,128), 80 were in the low protein category, 867 were in the moderate protein category, and 181 were in the high protein category. *P<0.01.

Adjusted mean IGF-1 levels were positively associated with protein consumption for both age groups (FIG. 5). Because IGF-1 was only available for a randomly selected subsample (n=2,253) we reexamined the age-specific associations between protein and cause-specific mortality in this sample and found them to be similar to what was seen in the full sample; although, with somewhat larger effect sizes (Table 15). Next we examined whether IGF-1 acted as a moderator or mediator in the association between protein and mortality. We found that while IGF-1 did not account for the association between protein consumption and mortality (Table 15), it was an important moderator of the association—as indicated by the statistically significant interactions between protein and IGF-1 level (Table 16).

Figure 12:
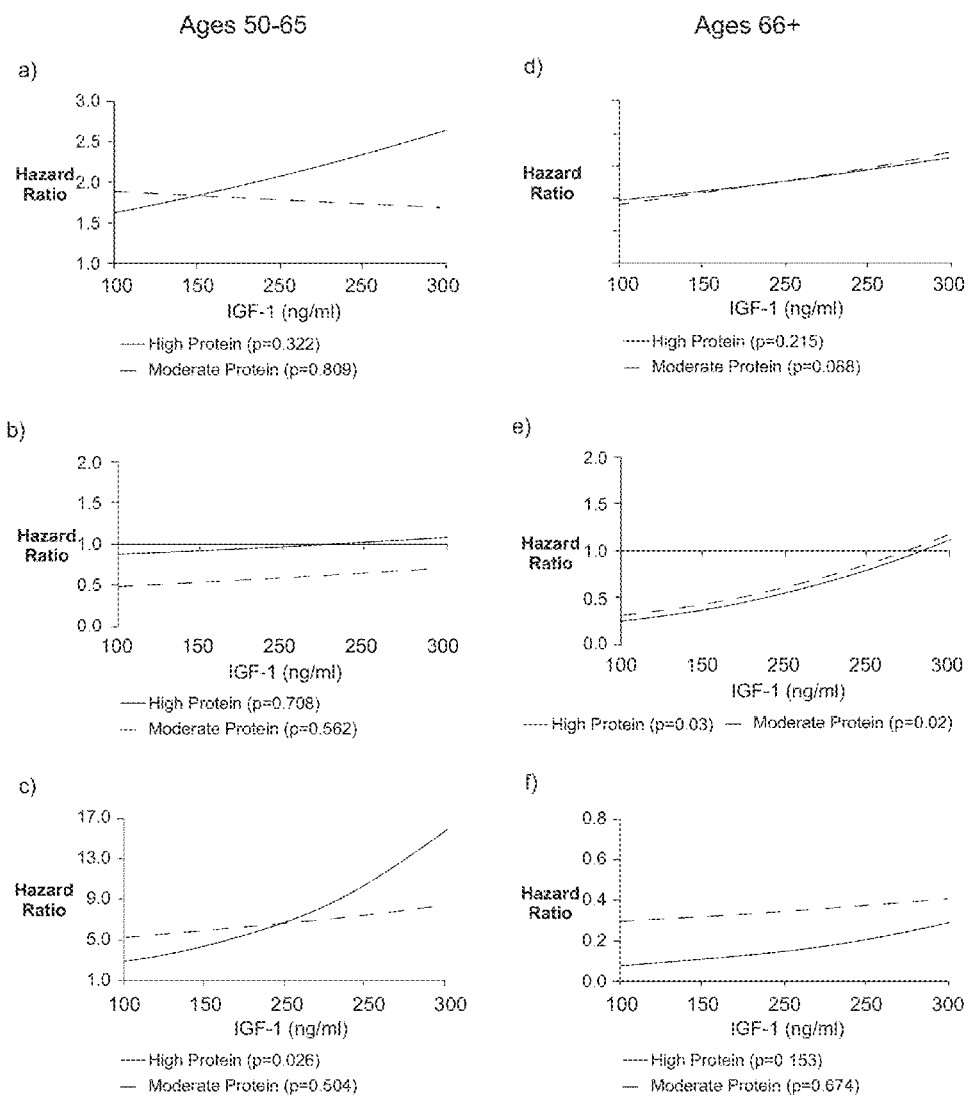
FIGS. 12 a)-f). IGF-1 Moderates the Association between Protein Consumption and Mortality. Based on results from Cox Proportional Hazard Models of the interaction between protein and IGF-1 on mortality, predicted Hazard Ratios were calculated by IGF-1 for both moderate and high protein groups relative to the low protein group. No significant interactions between protein and IGF-1 were found for all-cause (3a) or CVD mortality (3b) in the 50-65 year old age group. However, the interaction for IGF-1 and high vs low protein was significant (p=0.026) for cancer mortality (3c) for subjects ages 50-65. Results show that for every 10 ng/ml increase in IGF-1 the mortality risk of cancer increases for the high protein group relative to the low protein group by 9% ($HR_{high\ protein \times IGF-1}$: 1.09; 95% CI: 1.01-1.17). The interaction between protein and IGF-1 was significant for respondents ages 66+ only for CVD mortality. Those with high or moderate protein diets had a reduced risk of CVD if IGF-1 was also low; however, as IGF-1 increased there was no benefit.
Figure 20A:
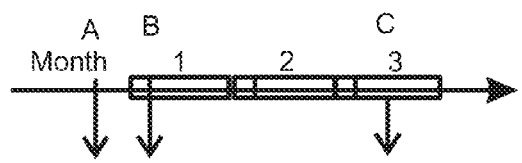
FIGS. 20 A-D. Human subjects participated in 3 cycles of a low protein low calorie and high nourishment 5-day fasting mimicking diet (FMD, indicated in green, see text) followed by approximately 3 weeks of normal diet (indicated in brown) (A). Blood were drawn before and at the end of the 5-day diet (time points A and B), and also 5-8 days after finishing the $3^{rd}$ 5-day FMD (time point C). The 5-day dieting significantly reduced blood glucose (B), IGF-1 (c) and IGFBP-1 (D) levels. Glucose *, $p<0.05$, N=18; IGF-1, **, $p<0.01$, *$p<0.05$, N=16; IGFBP-1, **, $p<0.01$, N=17; all statistical tests were performed as paired t test, two tailed on the original values.
Figure 20B:
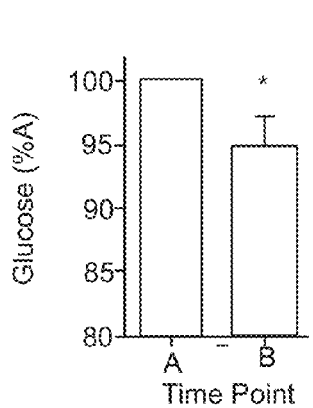
Figure 20C:
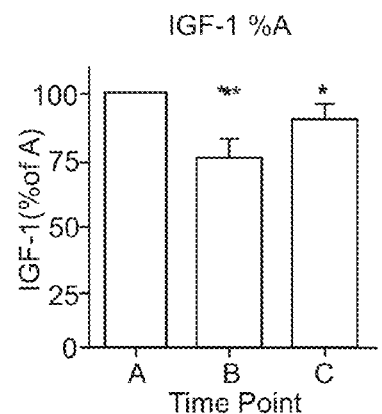
Figure 20D:
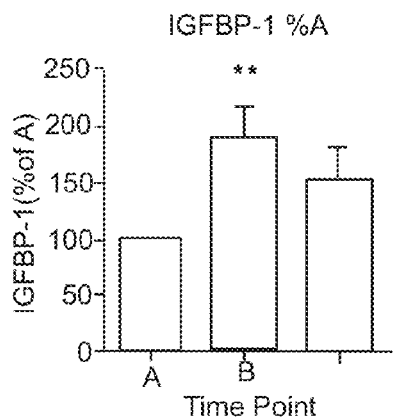

From these models, predicted hazard ratios by IGF-1 and protein group were calculated (FIG. 12). Results showed that for every 10 ng/ml increase in IGF-1 the mortality risk of cancer among subjects ages 50-65 increases for the high protein vs the low protein group by an additional 9% ($HR_{high\ protein \times IGF\text{-}1}$: 1.09; 95% CI: 1.01-1.17). Alternatively, among older subjects (66+ years), when comparing those in the low protein group, subjects with high or moderate protein diets had a reduced risk of CVD mortality if IGF-1 was also low; however, no benefits were found as IGF-1 increases.

Protein Intake, IGF-1, and Cancer in Mice

Figure 9A:
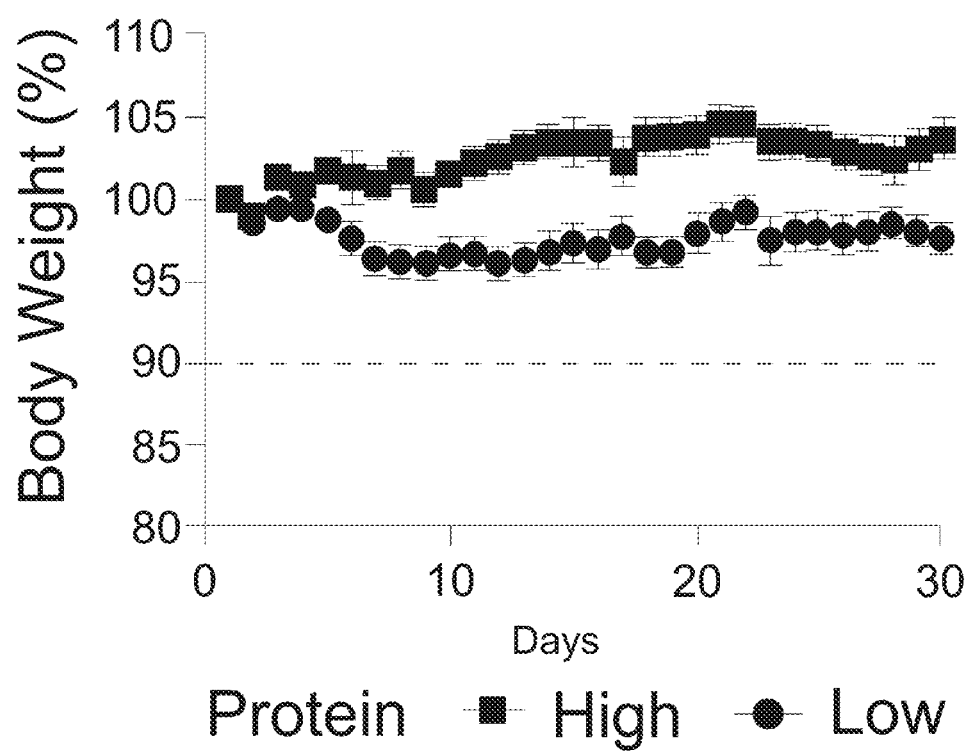
FIG. 9. (A) 30-day body weight of 18-week-old male C57BL/6 mice fed isocaloric diets varying in protein content either high (18%) or low (4%). (B) 30-day food intake in kcal/day of 18-week-old male C57BL/6 mice fed isocaloric diets varying in protein content either high (18%) or low (4%). (C) IGFBP-2 at day 16 in male (18 wk) C57BL/6 mice fed either a high protein (n=10) or low protein (n=10) diet. (D) IGFBP-3 at day 16 in male (18 wk) C57BL/6 mice fed either a high protein (n=10) or low protein (n=10) diet. (E) 30-day body weight of 12-week-old female BALB/c mice fed isocaloric diets varying in protein content either high (18%) or low (7%). (F) 30-day food intake in kcal/day of 12-week-old female BALB/c mice fed isocaloric diets varying in protein content either high (18%) or low (4%). (G) IGFBP-3 at day 16 in 12-week-old female BALB/c mice fed either a high protein (n=10) or low protein (n=10) diet. *P<0.05, P<0.01, *P<0.001, ****P<0.0001; ANOVA.
Figure 9B:
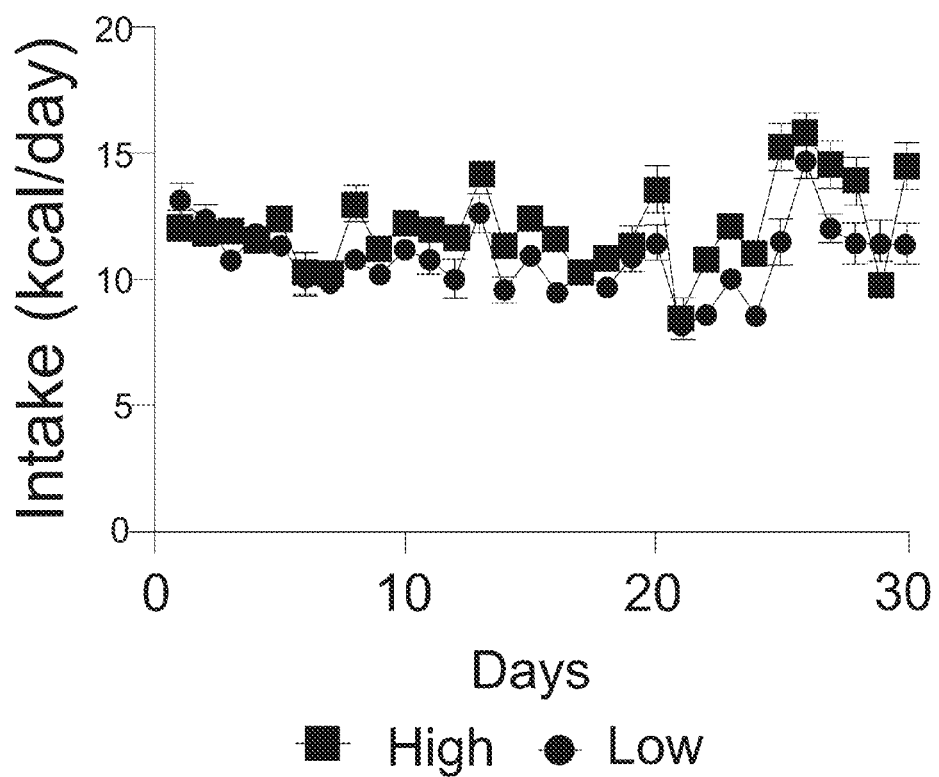
Figure 9C:
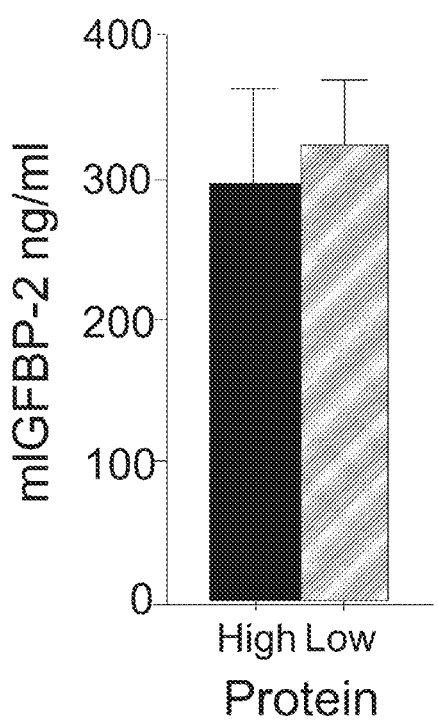
Figure 9D:
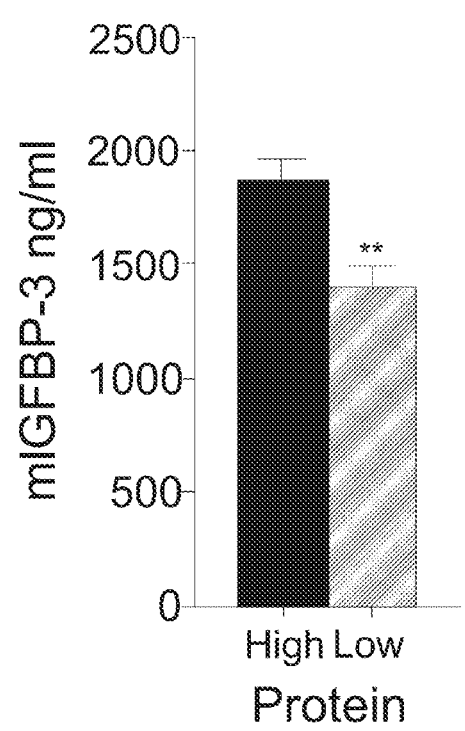

To verify causation and further our study of mechanism, we studied the effect of a range of protein intake (4-18%) similar to that of subjects in the NHANES study, on the levels of circulating IGF-1, cancer incidence, and tumor progression in rodents. 18-week-old male C57BL/6 mice were fed continuously for 39 days with experimental, isocaloric diets designed to provide either a high (18%) or a low (7%) amount of calories derived from protein, without imposing CR or causing malnutrition (FIG. 9A,B).

Figure 6A:
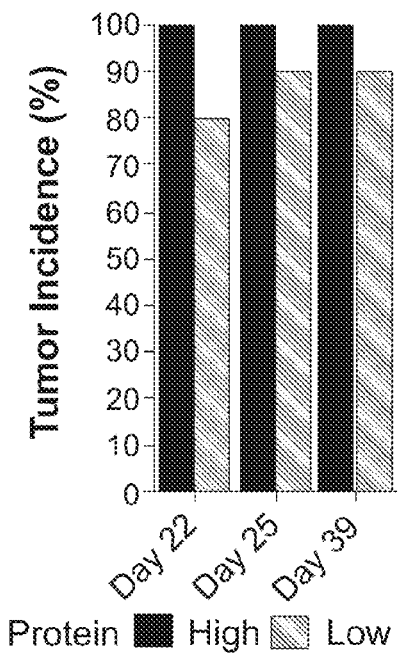
FIG. 6. (A) Tumor incidence in 18-week-old male C57BL/6 mice implanted with 20,000 melanoma (B16) cells, and fed either a high protein (n=10) or low protein (n=10) diet. (B) B16 Tumor volume progression in (18 wk) C57BL/6 male mice fed either a high protein (n=10) or low protein (n=10) diet. (C) IGF-1 at day 16 in (18 wk) male C57BL/6 mice fed either a high protein (n=5) or low protein (n=5) diet. (D) IGFBP-1 at day 16 in male (18 wk) C57BL/6 mice fed either a high protein (n=10) or low protein (n=10) diet. (E) B16 melanoma tumor progression in 10-month old female GHRKO mice (n=5) vs age-matched littermate controls (Ctrl; n=7). (F) Tumor incidence in 12-week-old female BALB/c mice implanted with 20,000 cell breast cancer (4T1) fed either a high protein (n=10) or low protein (7%; n=10) diet. (G) 4T1 breast cancer progression in female (12 wk) BALB/c mice fed either a high protein (n=10) or low protein (n=10) diet. (H) IGF-1 at day 16 in female (12 wk) BALB/c mice fed either a high casein protein (n=5) or low casein protein (n=5) diet. (I) IGFBP-1 at day 16 in female (12 wk) BALB/c mice fed either a high casein protein (n=10) or low casein protein (n=10) diet. (J) IGF-1 at day 16 in female (12 wk) BALB/c mice fed either a high soy protein (n=5) or low soy protein (n=5) diet. (K) IGFBP-1 at day 16 in female (12 wk) BALB/c mice fed either high soy protein (n=10) or low soy protein (n=10) diet. (L) Survival and (M) DNA mutation frequency of yeast exposed to a 0.5×, 1×, or 2× concentration of a standard amino acid mix. (N) PDS and STRE activity in yeast grown in media containing only Trp, Leu. and H is compared to those grown in the presence of all AA. (O) Ras2 deletion protects against oxidative stress-induced genomic instability measured as DNA mutation frequency ($Can^r$) in wild-type (DBY746) and ras2Δ mutants chronically exposed to 1 mM $H_2O_2$. (P) A model for the effect of amino acids on aging and genomic instability in S. cerevisiae. Amino acids activate the Tor-Sch9 and Ras-cAMP-PKA pathway also activated by glucose and promote age- and oxidative stress-dependent genomic instability in part via reduced activity of Gis1 and Msn2/4. *P<0.05, P<0.01, *P<0.001, ****P<0.0001.
Figure 6B:
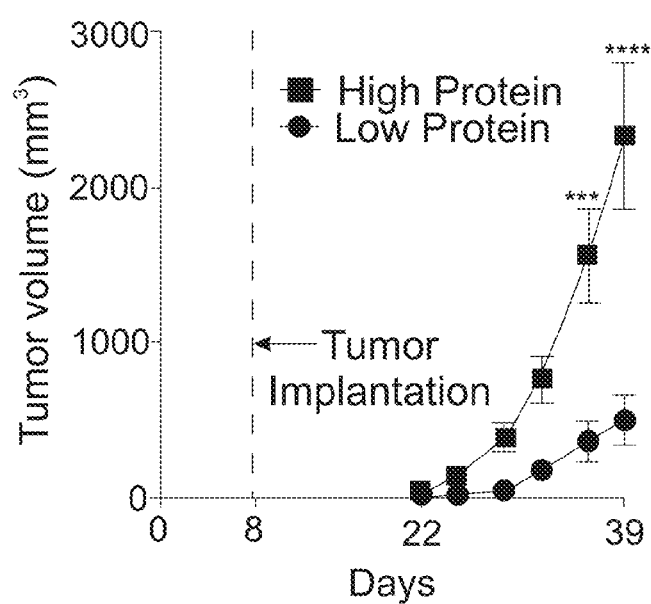
Figure 6C:
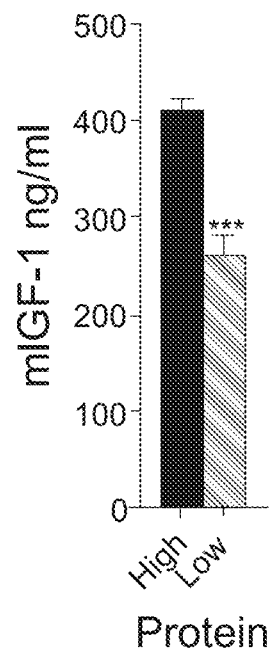
Figure 6D:
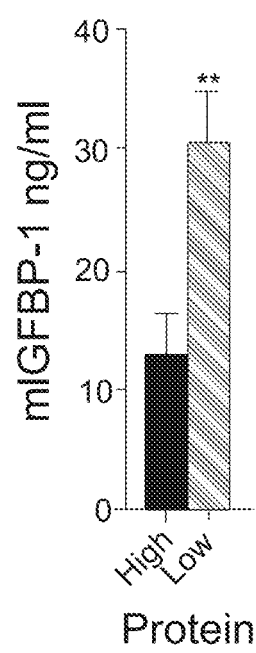

To understand how the different levels of protein and IGF-1 levels may affect the ability of a newly formed tumor to survive and grow after one week on their respective diets, both groups were implanted subcutaneously with 20,000 syngeneic, murine melanoma cells (B16). Tumor measurements began 15 days post implantation at 22 days on their respective diets, at which point incidence was found to be 100% in the high protein level group but only 80% in the low protein level group (FIG. 6A). At day 25, incidence rose to 90% in the low protein group, and remained there until the end of the experiment (FIG. 6A). From day 22 until the end of the experiment tumor size was significantly smaller in the group consuming lower amount of protein indicating a much slower tumor progression. At day 39 the mean tumor size was observed to be 78% larger in the high protein group (day 36 P=0.0001; day 39 P<0.0001)(FIG. 6B). Blood samples were obtained and analyzed at day 16 to determine the effect of protein intake on IGF-1 and the IGF-1 inhibitory protein, IGFBP-1. Serum IGF-1 was 35% lower (P=0.0004) in the low protein (4%) group when compared to animals fed the high protein (18%) diet (FIG. 6C). Conversely, serum IGFBP-1 was 136% higher (P=0.003) in the low protein group compared to the high protein group (FIG. 6D).

Figure 6E:
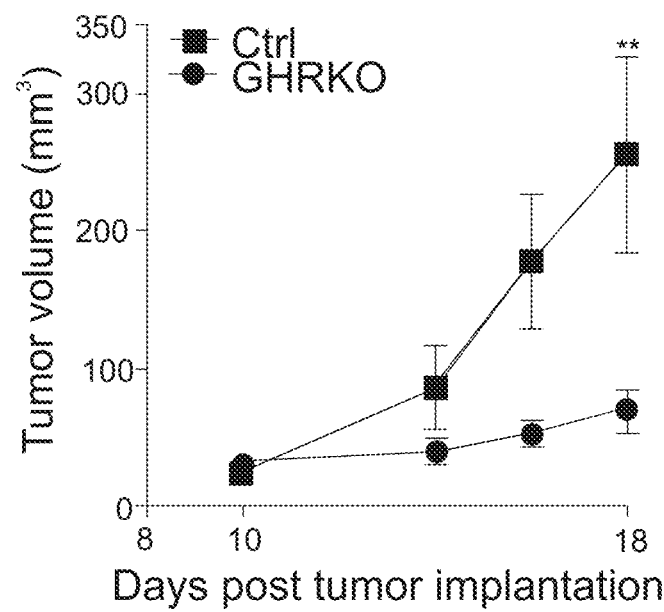

To test further the hypothesis that the GHR-IGF-1 axis promotes cancer progression, we implanted subcutaneous melanoma (B16) into GHR/IGF-1 deficient GHRKO mice and their respective age- and sex-matched littermate controls (18-week-old male C57BL/6 mice). Tumor measurements began 10 days post implantation and continued until day 18. The data shows that tumor progression is strongly inhibited in the GHRKO mice when compared to progression in the control group (FIG. 6E; P<0.01).

Figure 6F:
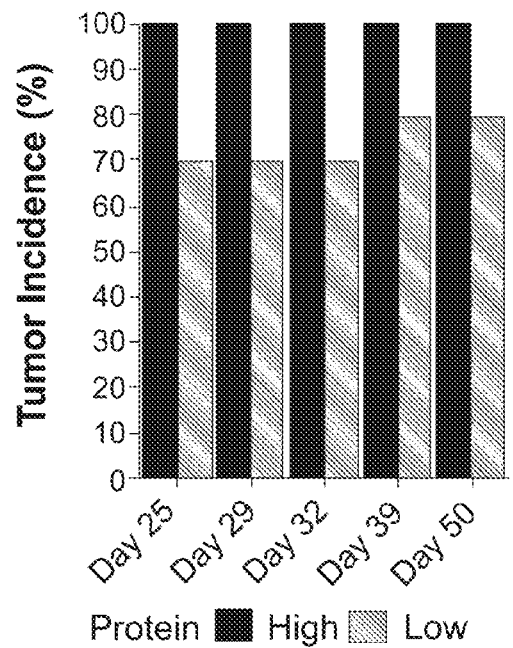
Figure 6G:
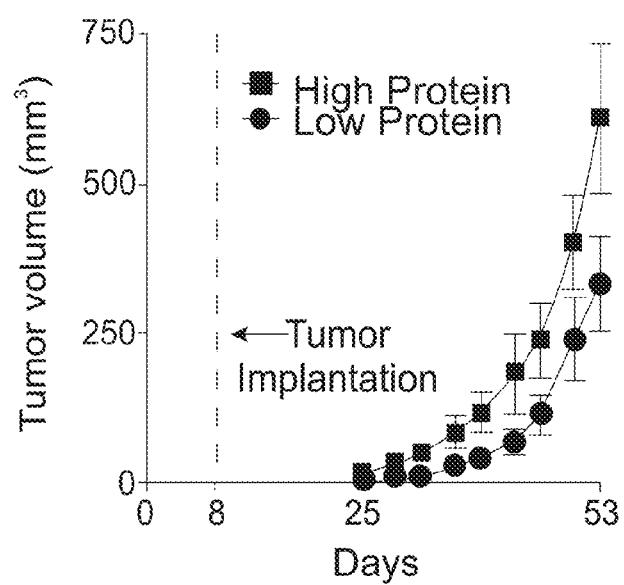
Figure 6H:
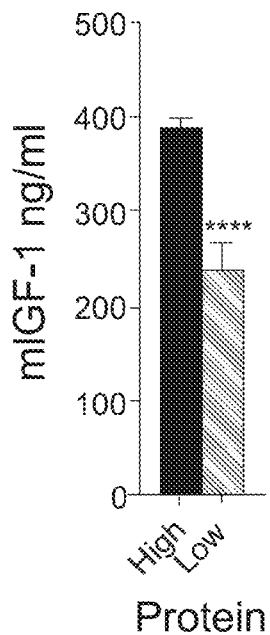
Figure 6I:
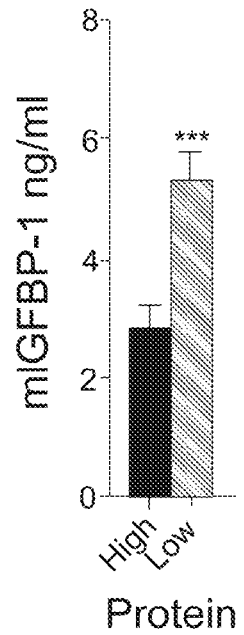
Figure 6J:
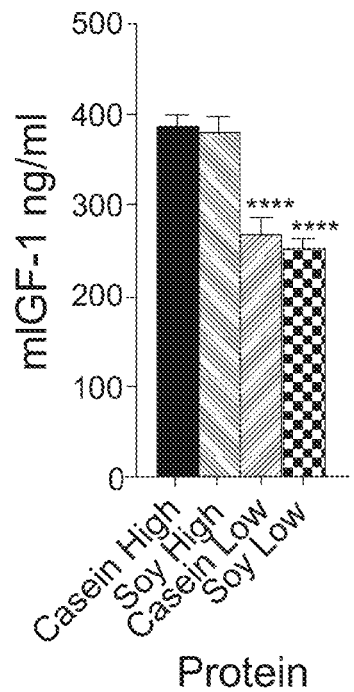
Figure 6K:
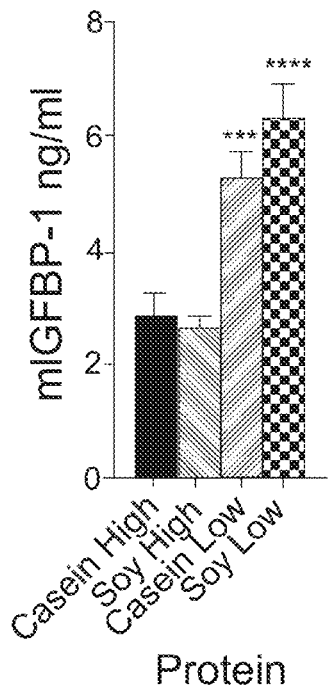
Figure 9E:
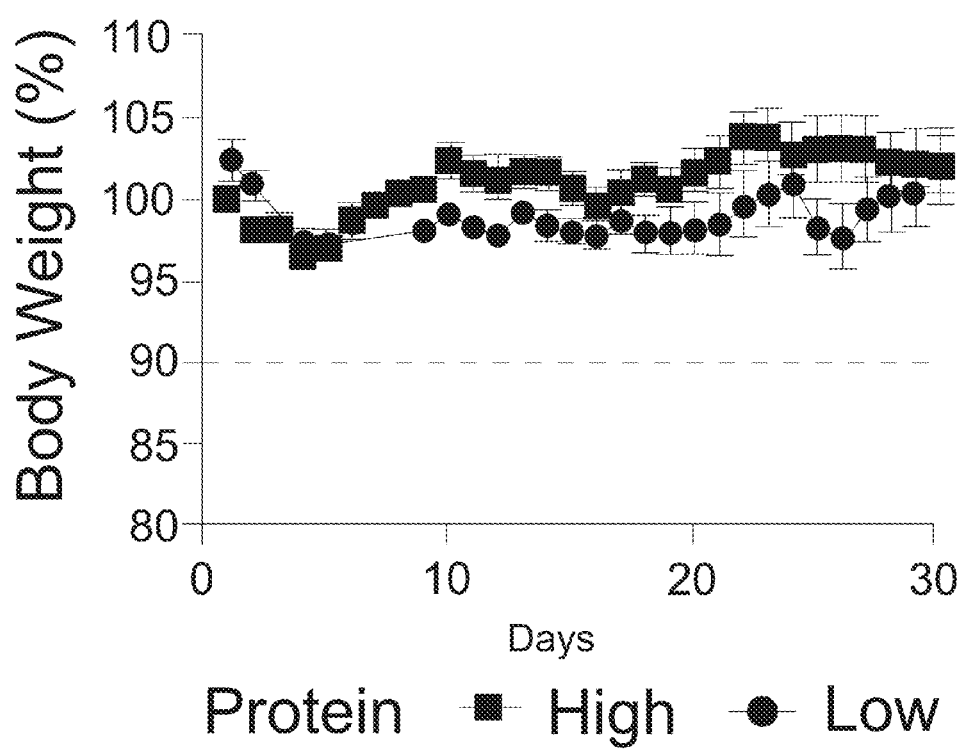
Figure 9F:
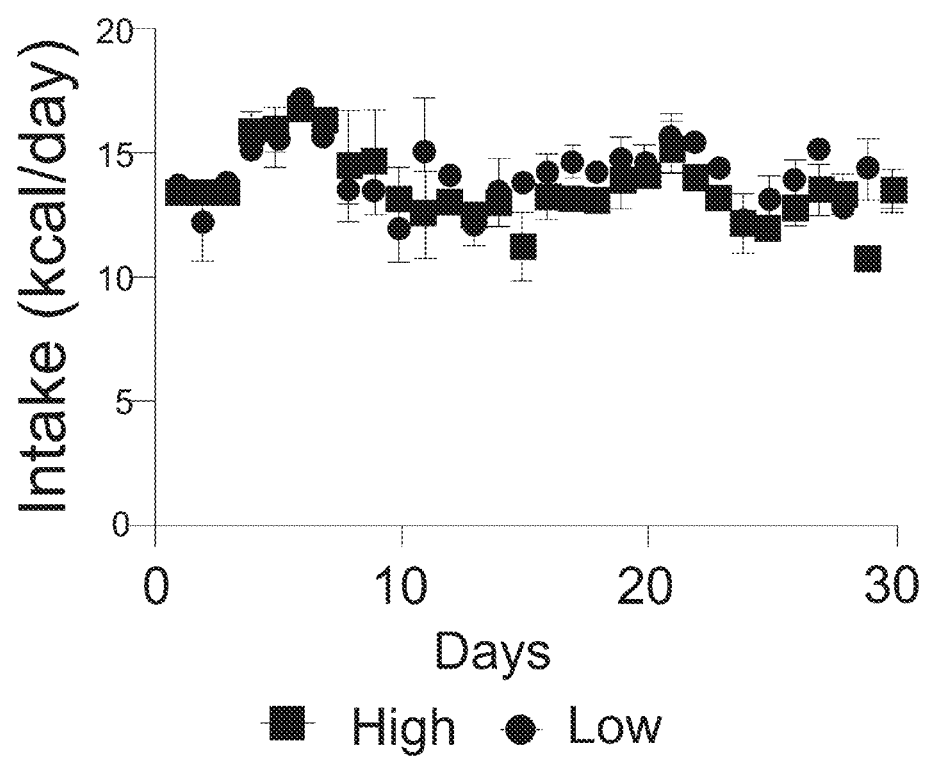
Figure 9G:
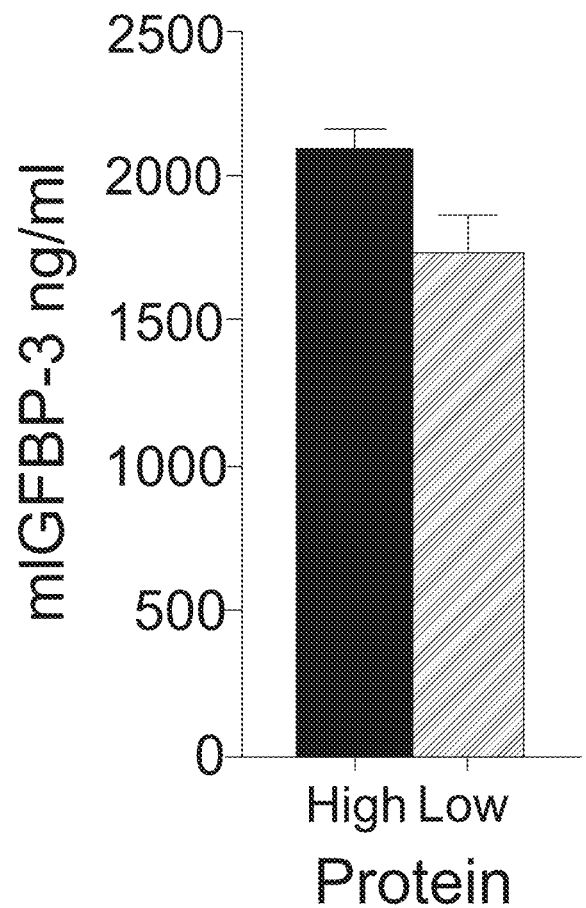
Figure 10:
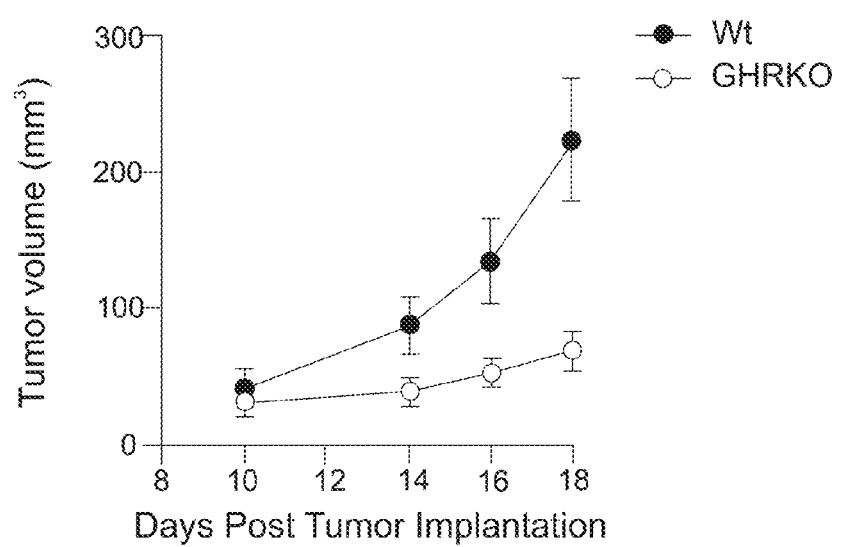
FIG. 10. Tumor volume progression of B16 melanoma in 10-month old female GHRKO mice (n=5) vs age-matched wild-type controls (Wt; n=13). **P<0.01.

We also used a breast cancer mouse model to test the relationship between protein levels, tumor incidence, and progression. 12-week-old female BALB/c mice were placed under the same dietary regimen as described for C57BL/6 mice, except that the mice had to be switched from a 4% to a 7% kcal from protein diet within the first week in order to prevent weight loss (FIG. 9E,F). After a week of feeding on these diets mice were implanted subcutaneously with 20,000 cells of syngeneic, metastatic, murine breast cancer (4T1), and 15 days later were assessed for tumors. On day 18 post-implantation (day 25 on the diet) tumor incidence was 100% in the high protein group but only 70% in the low protein group. The incidence in the low protein group rose to 80% at day 39 where it remained until the end of the experiment (FIG. 6F). Tumor progression data also shows that the groups on lower protein diets had a smaller mean tumor size. A 45% smaller mean tumor size was observed in the low protein group compared to the high protein group by day 53 at the end of the experiment (P=0.0038)(FIG. 6G). As for C57BL/6 mice, IGF-1 was measured at 16 days of dietary protein restriction. In the low protein intake group, IGF-1 levels were reduced by 30% compared to those in the high level group (P<0.0001) (FIG. 6H). Additionally, a low protein intake also caused an IGFBP1 increase of 84% (P=0.001)(FIG. 6I), similar to what was observed in the C57BL/6 genetic background (FIG. 6D). Similarly, when soy protein intake was reduced from high levels to low levels we observed a 30% decrease in IGF-1 (p<0.0001) (FIG. 6J) and a 140% increase in IGFBP-1 (p<0.0001)(FIG. 6K). Although there was a trend for an effect of substituting the same level of animal proteins with plant proteins on IGF-I and IGFBP1, the differences were not significant. These data suggest that lower protein intake may play a role in decreasing cancer incidence and/or progression in part by decreasing IGF-1 and increasing the IGF-1 inhibitor IGFBP1. Additional studies on various types of animal vs plant based proteins are necessary to determine their effect on IGF-I and IGFBP1.

Cellular Studies

Figure 6L:
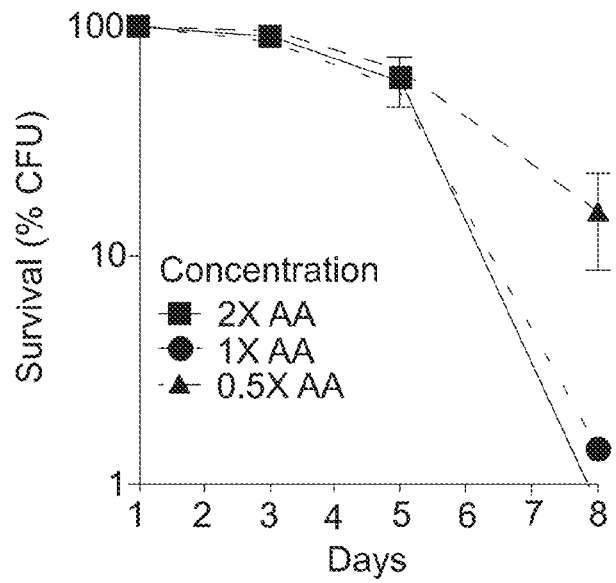

To understand whether there is a fundamental link between the level of amino acids and lifespan, the impact of the presence of specific concentrations of amino acids on yeast growth and development was assessed by survival and mutation rate assays. A wild type DBY746 *S. cerevisiae* strain was grown in the presence of half (0.5×), standard (1×), and double (2×) amino acid concentration with all other nutrients maintained constant. Survival was measured at days 1, 3, 5, and 8. No survival differences were observed during days 1 and 3. At day 5, the 2 highest amino acid concentrations showed a trend for increased mortality, which resulted in a 10-fold decrease in surviving cells by day 8 (FIG. 6L).

Figure 6M:
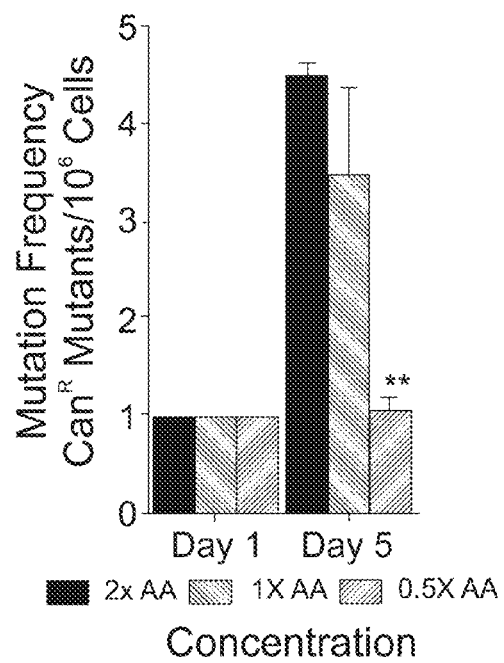

In order to assess the relationship between amino acids, aging, and age-dependent DNA damage we used aging *S. cerevisiae* to measure spontaneous mutation rate. The mutation rate was 3- and 4-fold higher in 5 day old but not young cells exposed to 1× and 2× amino acid levels, respectively, compared to cells exposed to a 0.5× amino acid concentration (FIG. 6M). These results indicate that even in unicellular organisms, amino acids promote cellular aging and age-dependent genomic instability.

Figure 6N:
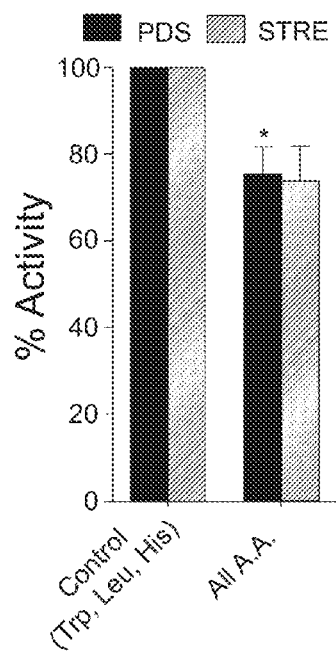
Figure 6O:
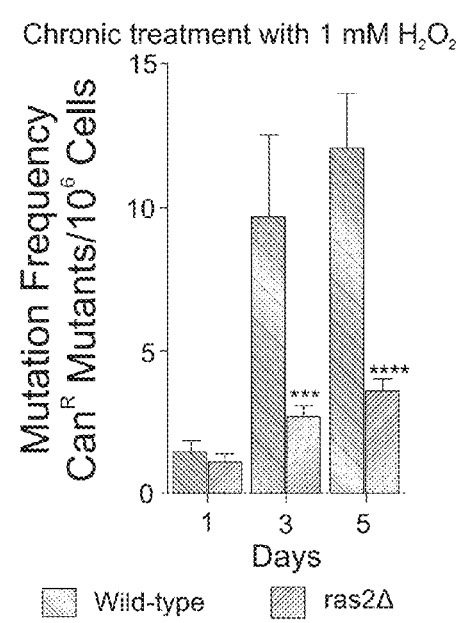

To further discern the pathways involved in promoting age-dependent genomic instability we measured the induction of stress responsive genes regulated by the Ras-PKA-Msn2-4 Tor-Sch9-Gis1 pathways in the presence or absence of amino acids. For cells grown in control media containing only Trp, Leu, and His (essential for growth in this strain) the presence of all amino acids in the media reduced the induction of stress resistance genes, indicating that the addition of amino acids was sufficient to inhibit cellular protection (FIG. 6N).

Figure 11A:
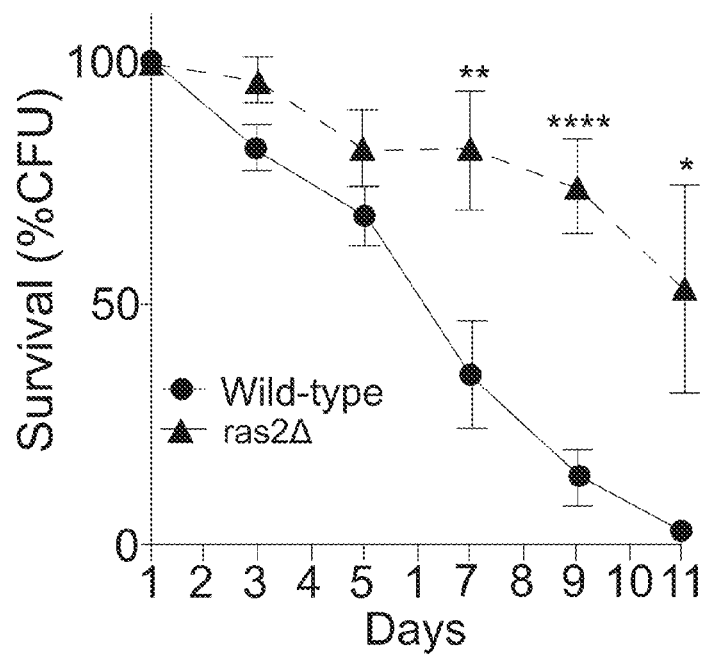
FIG. 11. (A) Yeast chronological survival and (B) attenuated age-dependent genomic instability shown as mutation frequency in the CAN1 gene (measured as $Can^r$ mutants/$10^6$ cells) in wild-type (DBY746) compared to ras2Δ mutants. (C) Chronological survival of wild-type and ras2Δ mutants chronically treated with 1 mM $H_2O_2$. (D) Lack of Ras2 protects against oxidative stress-induced genomic instability (mutation frequency $Can^r$). *P<0.05, P<0.01, **P<0.0001.
Figure 11B:
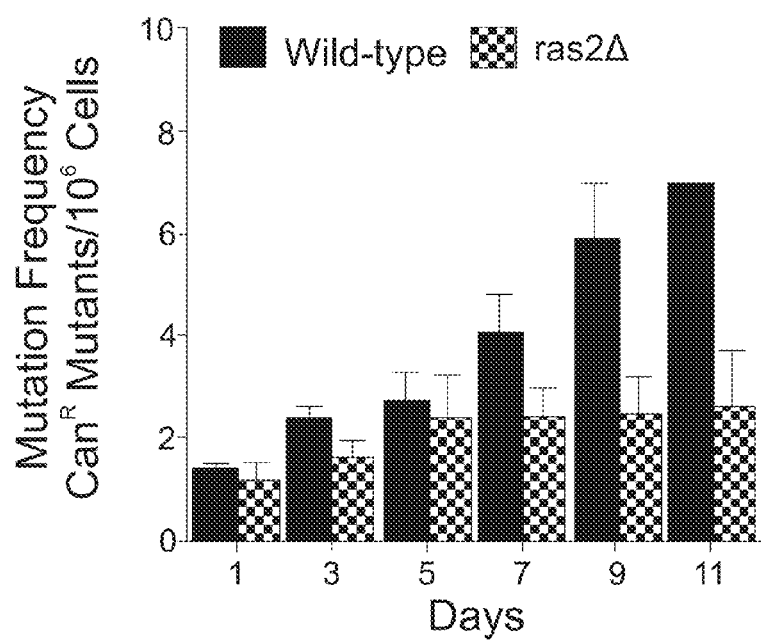
Figure 11C:
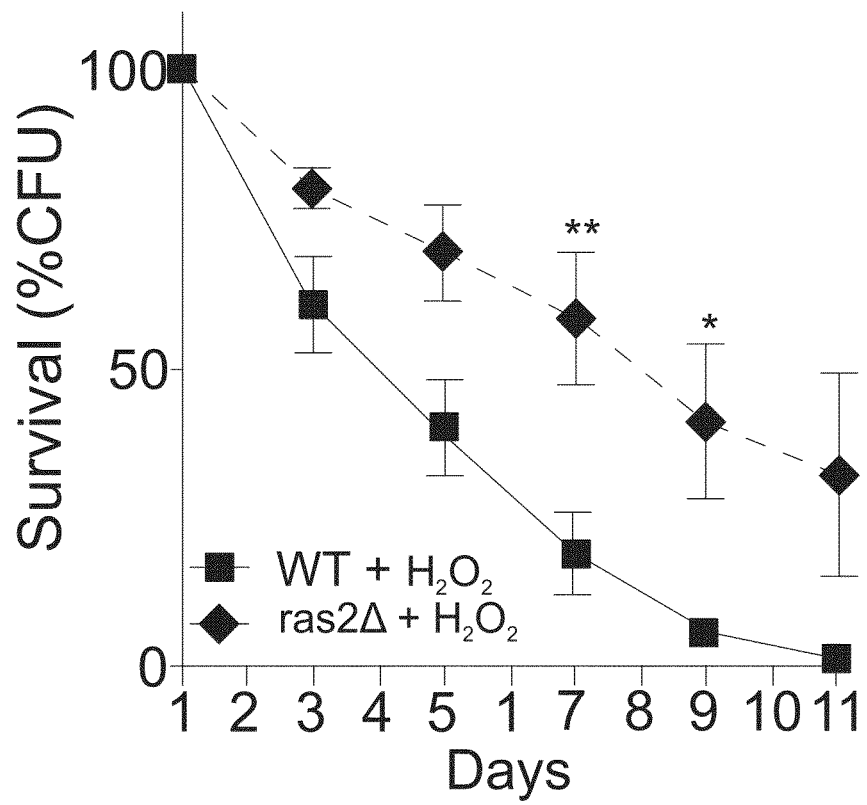
Figure 11D:
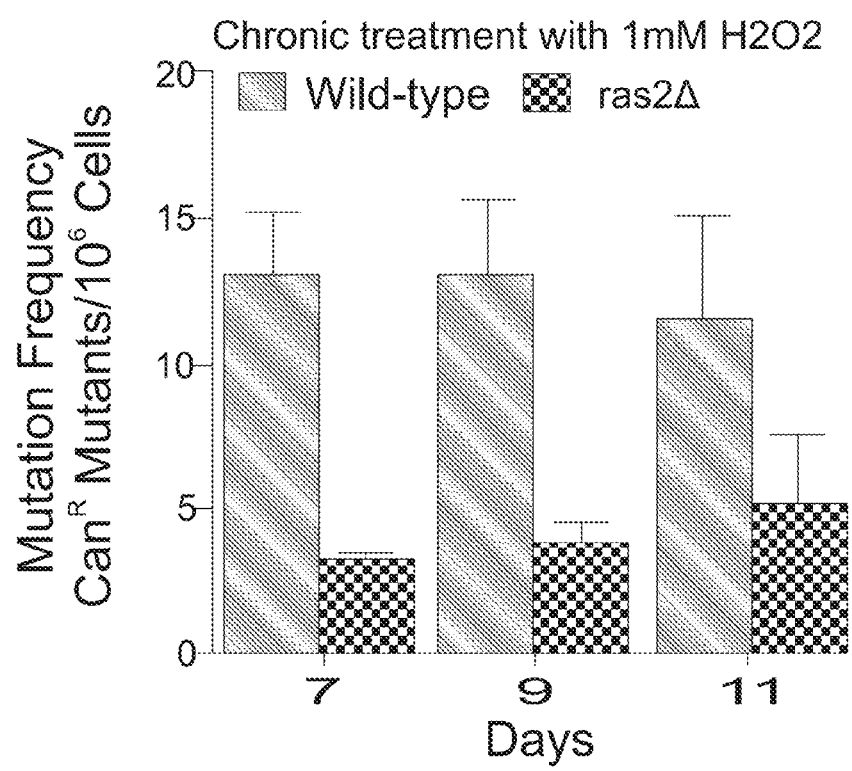

The Tor-Sch9 pathway extends longevity but also promotes DNA mutations. To determine whether Ras-cAMP-PKA signaling also regulates age-dependent genomic instability we studied ras2 deficient mutants. We confirmed that ras2Δ mutants are long-lived (FIG. 11A) but also show that inactivation of Ras signaling attenuated age- and oxidative stress-dependent genomic instability (FIG. 11B, 11C, 6O, 11D).

Figure 6P:
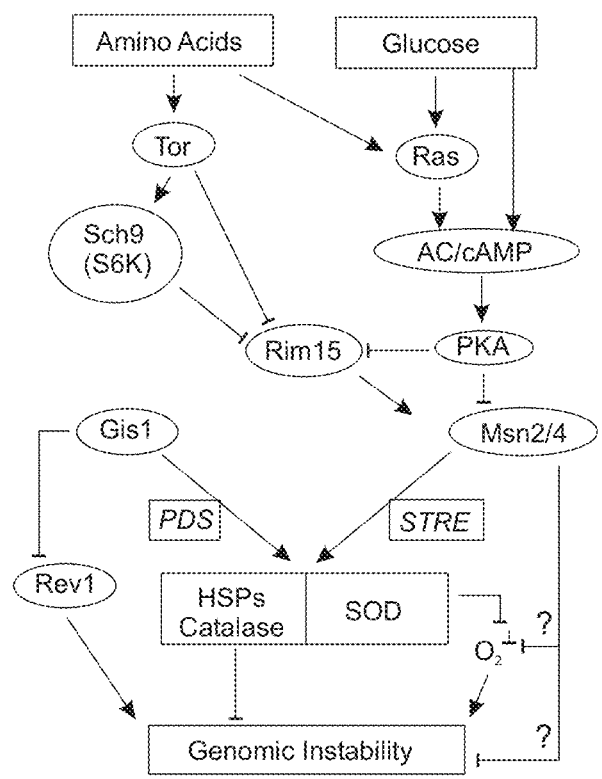
Figure 7A:
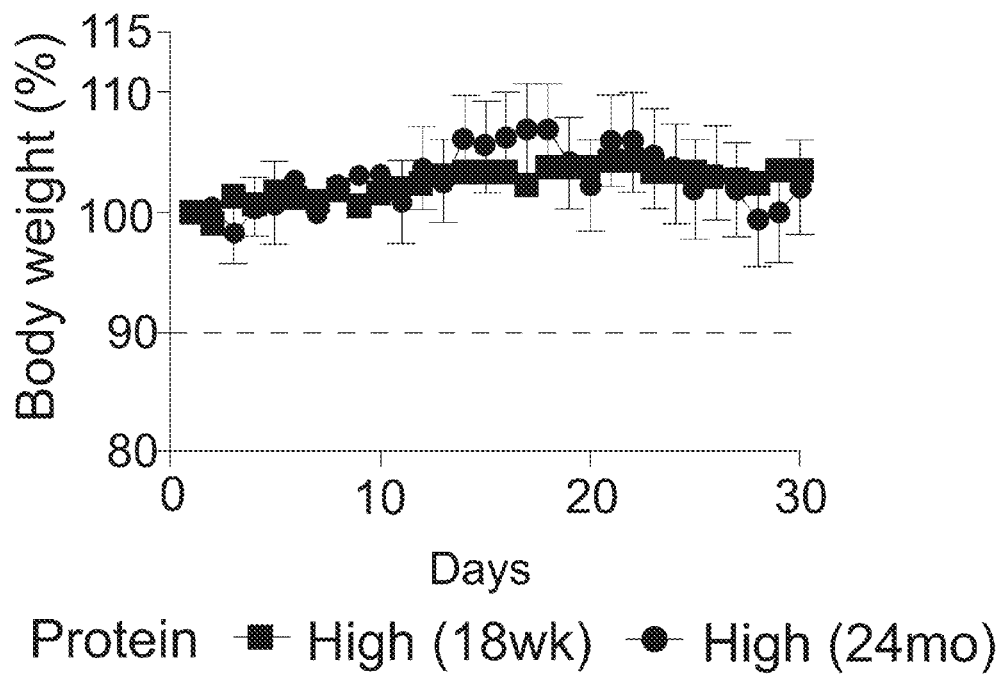
FIG. 7. Effect of protein intake on body weight in young and old mice. (A) Young (18-week-old) (n=10) and old (24-month-old) (n=6) C57BL/6 mice fed a high (18%) protein diet. (B) Young (18-week-old) (n=10) and old (24-month-old) (n=6) C57BL/6 mice fed a low (4%) protein diet.
Figure 7B:
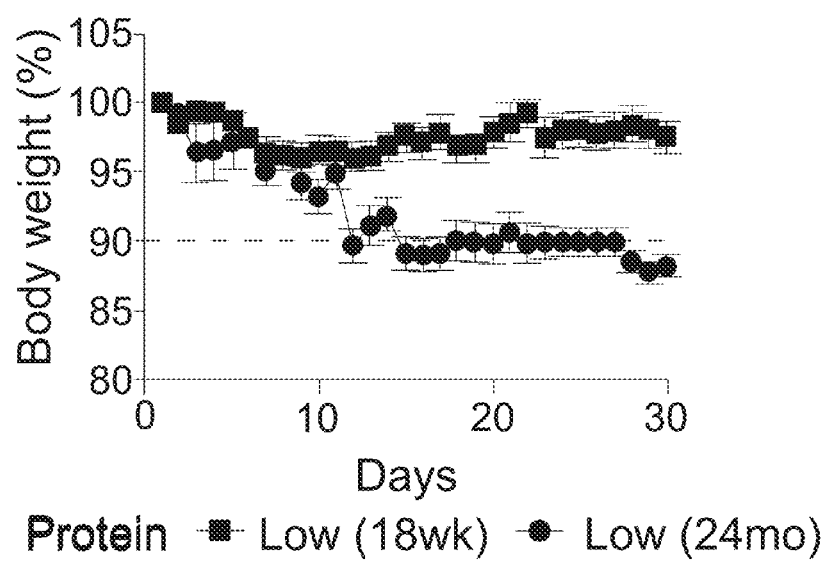

Together, these results suggest a mechanism where amino acids are able to affect mutation frequency and thus genomic instability, at least in part, by activation of the Tor-Sch9 and Ras/PKA pathways and decreased stress resistance (FIG. 6P).

Low Protein Intake and Weight Maintenance in Old Mice

Based on the observed opposite effects of a low protein diet in subjects 50-65 year old versus those 65 and older and on the major drop in BMI and IGF-1 levels after age 65, we hypothesized that older subjects on a low protein diet may become malnourished and unable to absorb or process a sufficient level of amino acids. To test this possibility in mice, we fed young mice (18-week-old) and old mice (24-month-old) with isocaloric diets containing either 18% or 4% animal protein. A very low protein diet was purposely selected to reveal any sensitivity to protein restriction in an old organism. Whereas old mice maintained on a high protein diet for 30 gained weight, old but not young mice on a low protein diet lost 10% of their weight by day 15 (FIG. 4A,B) in agreement with the effect of aging on turning the beneficial effects of protein restriction on mortality into negative effects.

Discussion

Here, using a major nationally-representative study of nutrition in the United States population, our results show that among those ages 45 and above, the level of protein intake is associated with increased risk of diabetes mortality, but not associated with differences in all-cause, cancer, or CVD mortality. Nevertheless, we found an age interaction for the association between protein consumption and mortality, with subjects ages 50-65 years experiencing benefits from low protein intake and subjects ages 66+ experiencing detriments from a low protein diet—at least for overall mortality and cancer. This may explain why the strong association between protein intake, IGF-1, and mortality reported here had not been previously described. Furthermore, among the 2253 subjects for whom IGF-1 levels were measured, the risks of all-cause and cancer mortality for those with high protein intake compared to the low protein intake group were increased even further for those who also had high levels of IGF-1. This is in agreement with previous studies associating IGF-1 levels to various types of cancer.

Notably, there was evidence that the type of protein consumed may be important. Our results showed that the proportion of proteins derived from animal sources accounted for a significant proportion of the association between overall protein intake and all-cause and cancer mortality. These results are in agreement with recent findings on the association between red meat consumption and death from all-cause, CVD, and cancer. Previous studies in the U.S. have found that a low-carbohydrate diet is associated with an increase in overall mortality and when such a diet is accompanied with increased consumption of animal-based products, the risk of overall, as well as CVD and cancer mortality, is increased even further. However, our study indicates that the effect of animal proteins on IGF-I, aging, diabetes and cancer may be the major promoter of mortality for people age 45-65 in the 18 years following the survey establishing protein intake. By then, the cohort that was 65 at the time of the interview would be 83 years old, underlining that the high protein intake may promote mortality in subjects that are older than 65.

Our results from yeast and mice may also explain at least part of the fundamental connection between proteins, cancer and overall mortality by providing a link between amino acids, stress resistance, DNA damage, and cancer incidence/progression. In mice, the changes caused by reduced protein levels had an effect potent enough to prevent the establishment of 10-30% of tumors, even when 20,000 tumor cells were already present at a subcutaneous site. Furthermore, the progression of both melanoma and breast cancer was strongly inhibited by the low protein diet indicating that low protein diets may have applications in both cancer prevention and treatment.

Although protein intake is associated with increased mortality for adults who were middle-aged at baseline, there was also evidence that a low protein diet may be hazardous for older adults. Both high and moderate protein intake in the elderly were associated with major improvements compared to the low group, suggesting that protein intake representing at least 10% of the calories consumed may be necessary after age 65 or possibly 75 to reduce age-dependent weight loss and, possibly prevent an excessive loss of IGF-1 and of other important factors. Previous studies have noted that an increased protein intake and the resulting increase in IGF-1 may prove beneficial in older adults. In fact, the dramatic switch from the protective to the detrimental effect of the low protein diet coincides with a time at which weight is known to stabilize and then decline. Based on previous longitudinal studies, weight tends to increase up until age 50-60, at which point it becomes stable before beginning to decline steadily by an average of 0.5% per year for those over age 65. We speculate that this may depend on the weight loss and frailty of subjects being considered with frail subjects who have lost a significant percentage of their body weight and have a low BMI being more susceptible to protein malnourishment. It is also possible that other factors such as inflammation or genetic factors may contribute to the sensitivity to protein restriction in elderly subjects, in agreement with our mouse studies.

Although other studies have noted age-associated declines of nutrient absorption in rodents related to changes in the pH microclimate, impaired adaptive response in the aged gut, and changes in the morphology of the intestine, there is still no clear association between morphological and absorptive changes in ageing. In humans, some studies have shown that dietary protein digestion and absorption kinetics are not impaired in vivo in healthy, elderly men, however, these studies have also reported increased splanchnic extraction of AAs which might result in decreased availability to peripheral tissues, and speculate that in the case of low protein intake or increased protein requirement the limited systemic availability of dietary AAs may contribute to decreased muscle protein synthesis. Furthermore, in humans other factors like poor dentition, medication, and psychosocial issues also play a significant role on rates of malnourishment.

IGF-1 has also been previously shown to decrease at older ages possibly increasing the risk of frailty, and mortality. Thus our findings may explain the controversy related to IGF-I and mortality indicating that a minimum levels of proteins and possibly IGF-1 is important in the elderly or that low circulating IGF-1 reflects a state of malnourishment frailty and/or morbidity. In fact, inflammation and other disorders are known to decrease IGF-1 levels, raising the possibility that the low protein and low IGF-1 group may contain a significant number of both malnourished and frail individuals having or in the process of developing major diseases.

There are some limitations to our study which should be acknowledged. First, the use of a single 24-hour dietary recall followed by up to 18-years of mortality assessment has the potential of misclassifying dietary practice if the 24 hour period was not a normal day. However, 93% of our sample reported that the 24 hour period represented a normal day. We also include this variable as a control in our analysis. Furthermore, the 24-hour dietary recall has been shown to be a very valid approach to identify the "usual diet" of subjects. While we must admit that the lack of longitudinal data on dietary consumption is a potential limitation of our study, study of dietary consistency over six years among older people revealed little change over time in dietary habits. Another study looking at dietary habits over twenty years showed that while energy intake decreased for protein, fat, and carbohydrates as people aged, the decreases were equal across the three types.

Another limitation of our study is that classification of respondents into protein groups, and then stratifying the sample for analysis, produced relatively small sample sizes, especially for analyses involving diabetes mortality among persons without diabetes at baseline or participants in the IGF-1 subsample. As a result, our Hazard Ratios and 95% confidence intervals may be much larger than what would have been seen with a larger sample size. Nevertheless, one would expect a small sample size to decrease our power and make it harder to detect associations. Therefore, our ability to detect significance indicates that the associations between protein and mortality are robust. Furthermore, the lower limits of the 95% confidence intervals from our mortality analyses were well above 1.0, signifying that the increased risk is probably large. Finally, given these limitations, our study was strengthened by its use of reliable cause-specific mortality data, as well as its inclusion of a large nationally-representative sample—a feature often missing from the previous literature.

Overall, our human and animal studies show that a low protein diet during middle age may be useful for the prevention of cancer and overall mortality, through a process that may involve, at least in part, regulation of circulating IGF-1 and possibly insulin levels. In agreement with other epidemiological and animal studies our findings suggest that a diet, in which plant-based nutrients represent the majority of the food intake, is likely to maximize health benefits. However, we propose that up to age 65 and possibly 75, depending on health status, the 0.7 to 0.8 grams of proteins/kg of body weight/day published by the Food and Nutrition Board of the Institute of Medicine, currently viewed as a minimum requirement, may be protective versus the 1-1.3 g grams of proteins/kg of body weight/day consumed by adults ages 19-70. We also propose that at older ages, it may be important to avoid low protein intake and gradually adopt a moderate to high protein possibly mostly plant based consumption to allow the maintenance of a healthy weight and protection from frailty.

Experimental Procedures

Nutrient Intake for Human Data

Nutrient intake data is based on reports of food and beverage intake during a 24-hour period. Data were collected via an automated, microcomputer-based coding system, with information on over eighty nutrients There are several advantages to using this method for collecting dietary data. Given that the time elapsing between consumption and recall is short, participants are typically able to recall more information. Also, unlike reporting methods, 24-hour dietary recall relies on data collection after consumption, reducing the potential for assessment to alter dietary behaviors. Furthermore, 24-hour recalls have been shown to be stronger estimates of total energy and protein consumption compared to the commonly used food frequency questionnaires and have also been shown to be a more valid measure of total energy and nutrient intake than both the Block food-frequency questionnaire, and the National Cancer Institute's Diet History Questionnaire. Finally, this approach has also been found to accurately assess energy, protein, fat, and carbohydrate intake, regardless of body mass index.

Epidemiological Mortality Follow-Up

Mortality data were available from the National Death Index. Information for 113 potential underlying causes of death (UCOD-113) was used to determine all-cause mortality, cardiovascular (CVD) mortality, cancer mortality and diabetes mortality.

Statistical Analysis for Human Data

Cox Proportional Hazard Models were used to estimate the association between intake of calories from protein on subsequent all-cause, CVD, Cancer, and Diabetes Mortality—with the latter three run using competing risks structures. Next we tested the interaction between age and protein consumption on the association with mortality. Based on these results, we categorized subjects into two age groups (50-65 years and 66+ years), which were used in the remainder of the analyses. Age-Stratified Proportional Hazard Models were used to estimate the association of percent calories from protein with Mortality within the two age groups, and examine whether the relationship was influenced by percent of calories from fat, percent of calories from carbohydrates, or animal protein. Hazard models were re-estimated for the IGF-1 subsample to determine whether including IGF-1 changed the association between protein intake and mortality. Finally, proportional hazard models were used to examine the interaction between protein and IGF-1, and used to calculate predicted hazard ratios for each protein group at various IGF-1 levels, to determine whether protein intake differentially impacts mortality depending on levels of IGF-1. All analyses were run using sample weights, accounting for sampling design, and controlling for age, race/ethnicity, education, sex, disease status, smoking, dietary changes, and total calorie consumption.

Materials and Methods for Yeast and Mouse Experiments

Using Cox Proportional Hazard models we found no association between protein consumption and either all-cause, CVD, or cancer mortality (Table 14). However, high and moderate protein consumption were positively associated with diabetes-related mortality. One explanation is that diabetes may be more prevalent in these groups, possibly because of a switch to a higher protein, lower fat, and lower carbohydrate intake following a diabetes diagnosis.

Finally, high versus low protein consumption was found to be associated with an over ten-fold increase in the risk of diabetes mortality for subjects age 66 and over. However, the much higher prevalence of subjects with a history of diabetes in the high protein group and the small number of subjects dying of diabetes in the low protein group may account for this, thus emphasizing the need for additional studies to determine the role of protein intake on diabetes incidence and mortality (HR: 10.64; 95% CI: 1.85-61.31).

Supplemental Materials and Methods

IGF-I in Human Data

Half of the subjects in NHANES III were randomly selected to take part in the morning examination, following a recommended nine hour fast. Of this sub-sample, 2,253 subjects included in our study complied and have measured fasting serum data for IGF-I. IGF-I was measured by Diagnostic Systems Laboratories Inc., using standard a laboratory protocol and reported in ng/ml.

Potential Confounders in Human Data

Age, race/ethnicity, education, sex, disease status, smoking, dietary changes, and total calorie consumption were included in analyses as potential confounders. Age was reported in years and top-coded at 90 in the data set by NHANES to protect confidentiality of respondents. Dummy variables were created to classify subjects into three race/ethnicity categories: non-Hispanic whites, non-Hispanic blacks, and Hispanics, Education was indicated by years of schooling. Dummy variables were created for self-reported smoking status—never, former, and current. Subjects were also asked to report on their history of diseases, in questions phrased as, "Has a Doctor ever told you had . . . " and used to create three dummy variables for presence of cancer, myocardial infarction, and diabetes history. Recent changes in dietary intake were assessed using responses to three questions-1) "During the past 12 months, have you tried to lose weight?"; 2) "During the past 12 months, have you changed what you eat because of any medical reason or health condition?"; and 3) (Following the 24-hour dietary recall) "Compare food consumed yesterday to usual". Waist circumference, which is preferred to BMI as an indicator of adiposity, was measured to the nearest 0.1 cm starting on the right side of the body at the iliac crest.

Cancer Models in Mice

All animal experiments were performed according to procedures approved by USC's Institutional Animal Care and Use Committee. To establish a subcutaneous cancer mouse model, we injected 18-week-old, male C57BL/6 mice as well as 10-month-old GHRKO mice, age-matched littermate control mice, and wild type littermates with B16 melanoma cells, and 12-week-old, female BALB/c with 4T1 breast cancer cells. Before injection, cells in log phase of growth were harvested and suspended in serum-free, high glucose Dulbecco's modified Eagle's medium (DMEM) at $2 \times 10^5$ cells or $2 \times 10^6$, and 100 ul ($2 \times 10^4$ cells per C57BL/6 or BALB/c mouse; $2 \times 10^5$ cells per GHRKO mouse) was subsequently injected subcutaneously in the lower back. All mice were shaved before subcutaneous tumor injection. Tumor incidence was determined by palpation of the injected area and tumor size was measured using a digital Vernier caliper starting 10-15 days post implantation. The experiments for C57BL/6 and BALB/c ended at different time points based on USC IACUC approved humane endpoint criteria for tumor size and ulceration. GHRKO (C57BL/6 background) mice were kindly provided by J. J. Kopchick (Ohio University, Athens).

Protein Restriction in Mice

AIN-93G standard chow was used as the casein-based high protein reference diet (18% kcal from protein and low protein diet 1,O was used as the casein-based low protein diet (4% kcal from protein) (Harlan Laboratories, Wis.). Diets were isocaloric and changes in kcal from fat or carbohydrates occurred in proportion to changes in kcal from protein. Daily intake measurements began 1 week before commencing the experiment in order to establish a baseline intake amount. All animals were fed daily for the duration of the experiment, and were provided with chow in excess of 50% of their baseline intake in order to allow ad lib, non-calorically restricted feeding. Before tumor implantation BALB/c mice were assigned to one of the 2 different kcal from protein groups and were pre-fed for 1 week. Feeding of these mice was continued throughout the course of the experiment the same as described above. To determine the effect of low protein on old mice, 24-month-old C57BL/6 mice were placed either in an 18% or 4% kcal from protein group and fed a continuous diet as described above. Body weights and intake were determined daily. Animals had access to water at all times.

Serum mIGF-I and mIGFBP-1 Measurements in Mice

Mice were anesthetized with 3% inhalant isoflurane, warmed gently to dilate the veins, and blood was collected from the tail vein to obtain serum weekly. Serum mIGF-I and mIGFBP-1 assays were performed as previously described (Hwang et al., 2008) using an in-house ELISA assay using recombinant mouse IGF-I or IGFBP-1 protein and polyclonal antibodies from R&D systems (Minneapolis, Minn.).

Statistical Analysis for Mouse Data

IGF-I comparisons between groups were performed using Student's t test, IGFBP-1 group comparisons were performed by Student's t test and ANOVA, and tumor volume progression group comparisons were performed with two-way ANOVA using GraphPad Prism v.6. All statistical analyses were two-sided and P values<0.05 were considered significant.

Yeast Survival and Mutation Frequency Measurement

Cells of the widely used DBY746 yeast strain (MATα leu2-3,112 his3-Δ1 trp1-289, ura3-52 GAL+) were made prototrophic by transformation with the corresponding plasmid, inoculated onto 1 ml of complete synthetic medium (SDC) and grown overnight at 30 degrees Celsius on an orbital shaker at 200 RPM.

This starter culture was then split (1:100) onto fresh synthetic SDC media containing 0.5×, 1× or 2× of the standard amino-acid concentration (Hu et al., 2013) at a 5:1 flask volume to medium volume ratio and put back in the incubator at the very same conditions. Aliquots of each culture were harvested every other day and proper dilutions plated onto rich YPD plates. Colony forming units (C.F.U.) were counted after two days of growth. Percentage of survival was assessed considering the CFU at day 3 as 100% of survival. All experiments were made in triplicate and standard deviation is shown. For mutation frequency calculation, $10^7$ cells were collected, at each survival time point, washed with water and plated onto synthetic complete (SDC) medium lacking arginine and supplemented with 60 □liq-1 of canavanine (Can). Can resistant colonies were measured after two to three days of growth at 30 degrees Celsius and expressed as the number of Can resistant clones out of $10^6$ viable CFU.

Ras2 Experiment Growth Conditions

Yeast chronological life span was monitored in expired SDC medium by measuring colony-forming units (CFUs) every 48 h. The number of CFUs at day 1 was considered to be the initial survival (100%) and was used to determine the age-dependent mortality.

Ras2 Experiment Can1 Mutation Frequency Measurements

Spontaneous mutation frequency was evaluated by measuring the frequency of mutations of the CANT (YEL063) gene. In brief, overnight inoculations were diluted in liquid SDC medium and incubated at 30° C. The cells' viability was measured every 2 d starting at day 1 by plating appropriate dilutions onto yeast extract peptone dextrose (YPD) medium plates and counting the CFUs. To identify the canavanine-resistant mutants ($Can^r$) in the liquid culture, an appropriate number of cells (starting amount of $2\times10^7$ cells) was harvested by centrifugation, washed once with sterile water, and plated on selective medium (SDC-Arg supplemented with 60 µg/ml 1-canavanine sulfate). Mutant colonies were counted after 3-4 d. The mutation frequency was expressed as the ratio of $Can^r$ to total viable cells.

Human Low Protein Intake Study

Human subjects participated in 3 cycles of a low protein low calorie and high nourishment 5-day fasting mimicking diet (FMD, indicated in green, see text) followed by approximately 3 weeks of normal diet (indicated in brown) (a). Blood were drawn before and at the end of the 5-day diet (time points A and B), and also 5-8 days after finishing the $3^{rd}$ 5-day FMD (time point C). The 5-day dieting significantly reduced blood glucose (b), IGF-1 (c) and IGFBP-1 (d) levels. Glucose *, p<0.05, N=18; IGF-1, **, p<0.01, *p<0.05, N=16; IGFBP-1, **, p<0.01, N=17; all statistical tests were performed as paired t test, two tailed on the original values. The results of this study are found in FIG. 20.

Material and Methods for Chemotoxicity Experiments 2.1. Mice

All animal protocols were approved by the Institutional Animal Care and Use Committee (IACUC) of the University of Southern California. 12-15 week old female CD-1, BalB/C or C57BL/6N mice (Charles River) were maintained in a pathogen-free environment throughout the experiments.

2.2. Macronutrient Defined Diets

Figure 21:
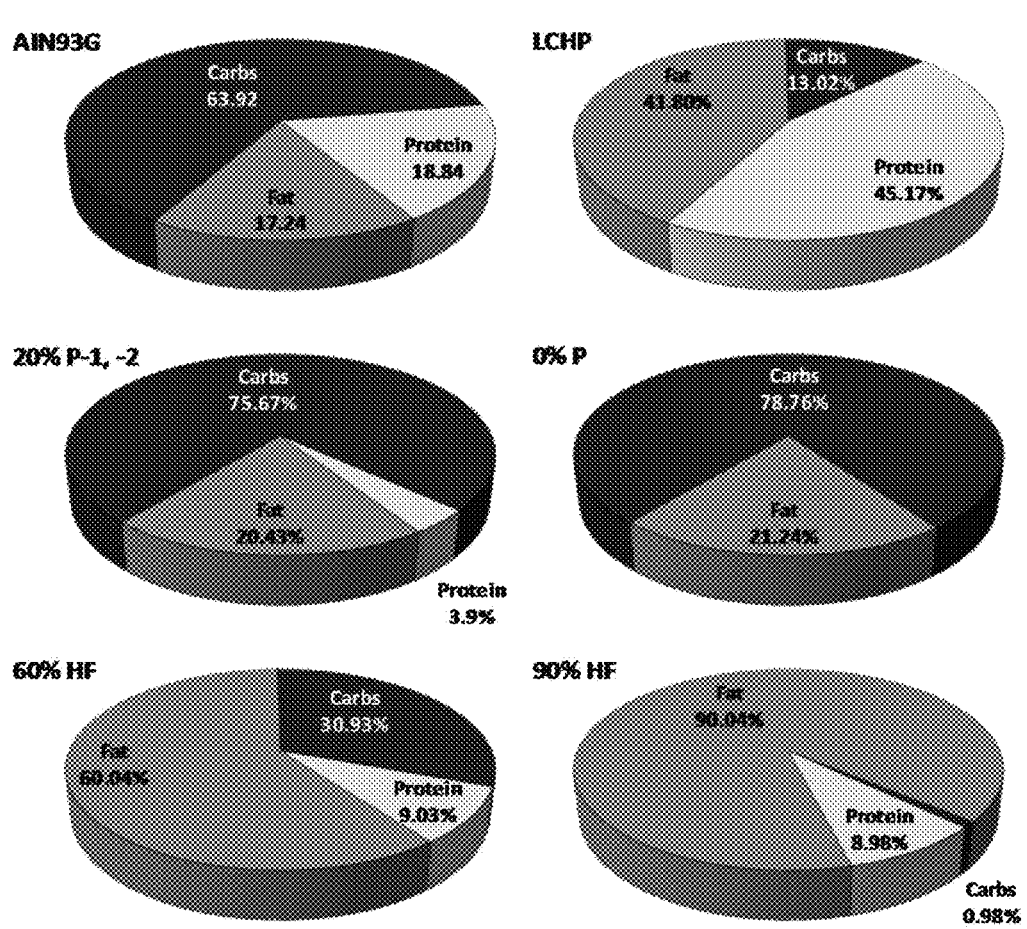
FIG. 21. Calories supplied by Macronutrients of the Experimental Diets in %. AIN93G standard chow was the reference diet and supplied to all mice. The experimental diets modified in the macronutrient composition (fat, protein and carbohydrates) were all based on this diet. The low-carbohydrate LCHP diet had calories from carbohydrates reduced to 20% compared to the AIN93G formulation (13% vs. 63.9%) but contained more protein (45.2%) and fat (41.8%). Diets 20% P-1 (soybean oil as fat source) and 20% P-2 (coconut oil as fat source) had calories from protein sources reduced to 20% compared to the AIN93G formulation; the 0% P diet contained no protein; all these diets were isocaloric to the AIN93G standard chow. The ketogenic high fat diet 60% HF was designed to supply 60% of the consumed calories from fat sources, the calories coming from protein and carbohydrates were reduced proportionally. The 90% HF diet was a ketogenic diet which contains 90% of fat while supplying only minimal carbohydrates (less than 1%) and half of the protein content (9%). Detailed diet composition and calorie content are summarized in Table 14.

AIN93G standard chow (Harlan) was used as the reference diet and supplied to all mice if not indicated otherwise. Diets modified in the macronutrient composition (fat, protein and carbohydrates) were all based on AIN93G (FIG. 21 and Table 20). Diets 20% P-1 (soybean oil as fat source) and 20% P-2 (coconut oil as fat source) had calories from protein sources reduced to 20% compared to the AIN93G formulation; the 0% P diet contained no protein; all these diets were isocaloric to the AIN93G standard chow. The low-carbohydrate LCHP diet had calories from carbohydrates reduced to 20% compared to the AIN93G formulation (13% vs. 63.9%) but contained more protein (45.2%) and fat (41.8%). The ketogenic high fat diet 60% HF was designed to supply 60% of the consumed calories from fat sources, the calories coming from protein and carbohydrates were reduced proportionally. The 90% HF diet was a ketogenic diet which contains 90% of fat while supplying only minimal carbohydrates (less than 1%) and half of the protein content (9%). Detailed diet composition and calorie content are summarized in Table S2. Mice were fed with the AIN93G control diet before commencing the experiments and based on their initial bodyweight grouped into the experimental groups (N=5/group). Mice were acclimated to the test diets one week prior to the experiments (adjustment schedule is shown in Table 22). All diets were supplied ad lib unless indicated otherwise.

2.3. Calorie Restriction (CR) and Short-Term Starvation (STS)

For calorie restriction using the AIN93G diet, the standard chow was grounded into a powder and mixed in hydrogel (Clear $H_2O$) in the necessary amounts to achieve 60%, 50%, 40%, 20%, 10% calorie density of AIN93G (Table 23). The calorie restricted macronutrient modified diets were prepared similarly (Table 24). To avoid malnutrition, all diets were supplemented with vitamins, minerals, fiber and essential fatty acids matching those in AIN93G. Baseline food intake (3.7 g or 14 kcal/day) was determined with AIN93G feeding prior to the experiment (data not shown). For the short-term starvation (STS) regimen, mice had no access to food for up to 60 hours.

For all CR and STS experiments, mice were single caged in standard shoebox-cages which were refreshed daily to avoid coprophragy or feeding on residual chow. Animals had access to water at all times and were supplied with hydrogel to ensure sufficient hydration. Bodyweight of each individual animal was measured routinely during the CR or STS regimens.

2.4. Blood Collection for Glucose and IGF-1 Measurements

Mice were anesthetized with 2% inhalant isoflurane and blood was collected by left ventricular cardiac puncture. Blood was collected in tubes coated with $K^2$-EDTA for serum preparation (BD). Blood glucose was measured with the Precision Xtra blood glucose monitoring system (Abbott Laboratories). IGF-1 was measured using a mouse specific ELISA kit (R&D Systems).

2.5. Resistance to High-Dose Chemotherapy 12-15 week-old female CD-1 mice weighing 25-32 g were starved for up to 60 h (STS) or fed with the macronutrient modified 50% CR diets for 3 days, followed by an intravenous injection of 24 mg/kg Doxorubicin (DXR, Bedford Laboratories). In all experiments mice were offered AIN93G standard chow after chemo drug injection and monitored daily. Animals showing signs of severe stress and/or deteriorating health status were designated as moribund and euthanized.

2.6. Subcutaneous Tumor Model

Murine 4T1 breast cancer and GL26 glioma cells were maintained in DMEM (Invitrogen) supplemented with 10% fetal bovine serum (FBS) at 37° C. under 5% $CO_2$. Cells in log phase growth were washed and suspended in PBS at $2 \times 10^6$ cells/mL and injected subcutaneously (s.c., $2 \times 10^5$ cells/mouse in 100 μL PBS) in the lower back region of the mouse. Tumor size was measured using a caliper. To mimic multicycle treatments in humans, mice were treated intravenously (i.v., lateral tail vein) with Cisplatin (Teva Parenteral Medicines Inc.) three times on days 15, 33 and 44 after tumor inoculation at 12, 8 and 8 mg/kg body weight, respectively. Mice were monitored daily and animals showing signs of severe stress, deteriorating health status or excess tumor load (2000 mm$^3$) were designated as moribund and euthanized.

2.7. Statistical Analysis

Comparisons between groups in the glucose and IGF-1 measurements were done with ANOVA, followed by Tukey's multiple comparison using GraphPad Prism v.5. All statistical analyses were two-sided and P values<0.05 were considered significant.

3. Results

3.1. Effects of Calorie Restriction on Glucose and IGF-1 Levels

Short-term starvation (STS) reduces serum levels of glucose and IGF-1, increases cellular protection against high-dose chemotherapy, and sensitizes malignant cells to chemotherapeutic drugs. STS effects on glucose and IGF-1 are usually achieved once animals lost approximately 20% bodyweight. Thus, the 20% weight-loss was used as a criterion to compare glucose and IGF-1 levels of calorie restricted diets to those obtained from a 60 h STS regimen.

Figure 22:
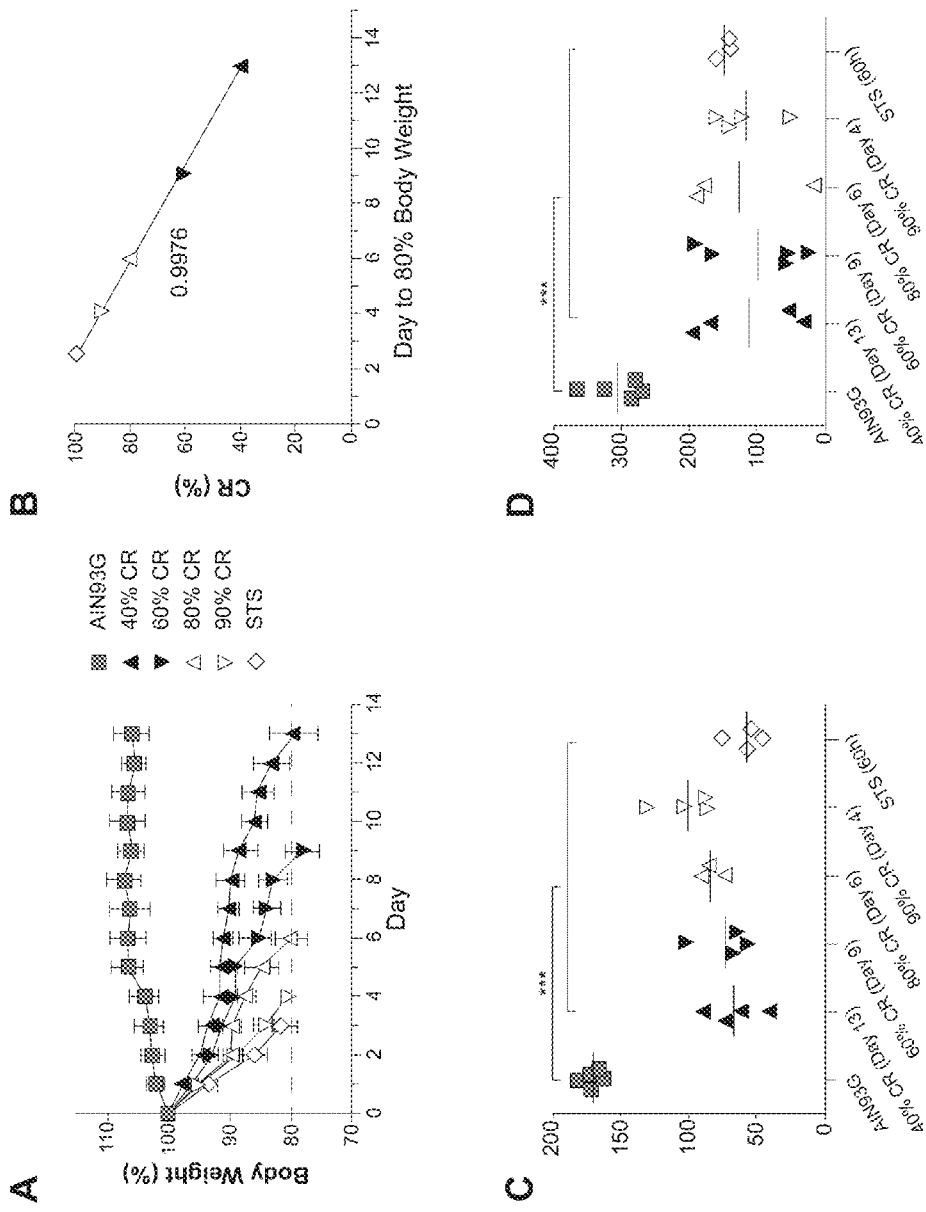
FIG. 22. Calorie Restriction reduces Bodyweight, Glucose and IGF-1. A) Female CD-1 mice, age 12-15 weeks were either fed ad lib (grey square) with AIN93G rodent standard chow, exposed to 40%, 60%, 80% and 90% calorie restricted AIN93G diets (triangles) or fasted (STS, green rectangle) until mice lost 20% of their initial bodyweight (dotted line). N=5 per experimental group. All data presented as mean±SEM. B) Linear fit for the severity of the CR regimen vs. the duration (days) until 80% bodyweight was reached. C) Blood glucose levels for mice once 80% bodyweight was reached. Red line represents mean; * $p<0.05$, * $p<0.001$, ANOVA, Tukey's multiple comparison. D) Serum IGF-1 levels for mice once 80% bodyweight was reached. Red line represents mean; * $p<0.001$, ANOVA, Tukey's multiple comparison.
Figure 26B:
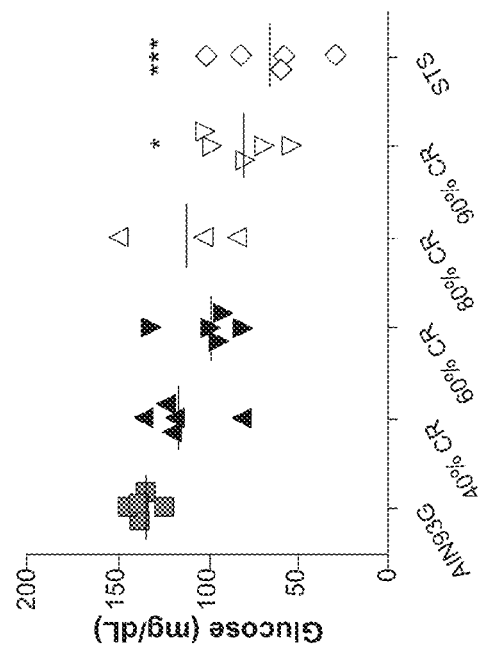
FIG. 26. A) Food intake in kcal/day for animals fed ad lib (grey square) with AIN93G rodent standard chow, fed with 40%, 60%, 80% and 90% calorie restricted AIN93G diets (triangles) or fasted (STS, green rectangle) until mice lost 20% of their initial bodyweight. B) Blood glucose levels for mice after 48 h exposure to all experimental diets. Line represents mean;  $p<0.01$, * $p<0.001$, ANOVA, Tukey's multiple comparison.
Figure 26A:
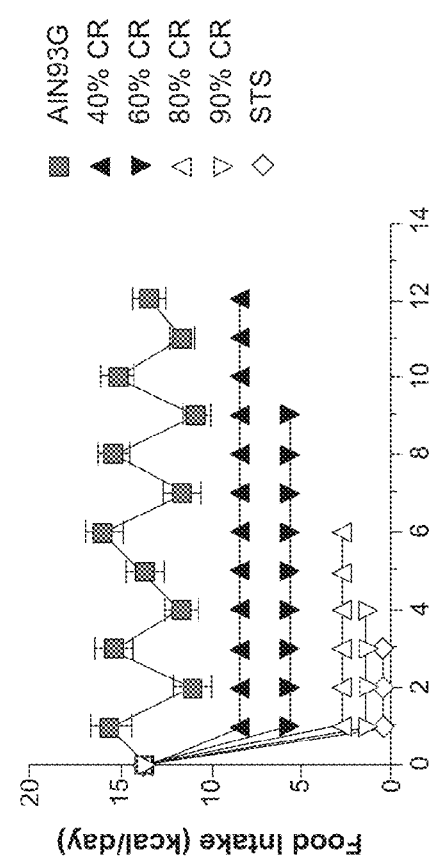

The 20% weight-loss threshold was reached at 4 days for 90% CR, 6 days for 80% CR, 9 days for 60% CR, or 13 days for 40% CR (FIG. 22A and FIG. 26A). The time to achieve 20% weight-loss strongly depends on the severity of the calorie restriction (linear fit with $r^2=0.9976$; FIG. 22B). At 48 hours, the reduction in blood glucose levels correlates with the severity of the calorie restriction (linear fit with $r^2=0.7931$; Supplementary FIG. 26B). The 60 h fasting regimen (STS) reduces blood glucose levels by 70% compared to that in ad lib fed mice (FIG. 22C, P<0.001). The 4 day 90% CR regime reduced blood glucose by approximately 40%, significantly less than STS (P<0.05). In addition, a trend was observed for the effect of CR in lowering blood glucose depending on the length of the CR-feeding: the glucose levels in the 13-day 40% CR feeding was significantly (P<0.05) lower than in the 4-day long 90% CR group. However, no calorie restricted group resulted in blood glucose levels that were lower than in the 60 h fasting group; and 9 or more days of CR were required to obtain glucose lowering effects in the range of those in the fasted group (FIG. 22C). Mice of all experimental CR groups, independently of the severity of the restriction, reached similar serum IGF-1 levels once the 20% weight-loss margin was reached and had significantly (P<0.001) lower IGF-1 levels than mice in the ad lib control group (FIG. 22D).

3.2. Effect of Macronutrient Defined Diets on Glucose and IGF-1 Levels

A set of macronutrient-defined diets (FIG. 21 and Table 20) were designed based on the AIN93G rodent chow to determine whether the restriction of specific dietary constituents could mimic the effects of STS or short-term CR, on blood glucose and/or serum IGF-1. The low protein diets 20% P-1 (soybean oil as fat source) and 20% P-2 (coconut oil as fat source) have calories from protein sources reduced to 20% compared to the original AIN93G formulation while carbohydrates and fat are increased to maintain the diets isocaloric to AIN93G. The 0% P diet contains no protein; carbohydrates as well as fat are increased proportionally to keep the diet isocaloric to the standard chow. The LCHP diet has the calories from carbohydrate sources reduced to 20% compared to the original AIN93G formulation (13% vs. 63.9%) but supplies more protein and fat. The high fat ketogenic diet 60% HF was designed to supply 60% of the consumed calories from fat sources, the calories coming from protein and carbohydrates were reduced proportionally. The 90% HF diet is a ketogenic diet that contains 90% of the calories from fat while supplying only minimal (less than 1%) carbohydrates and has 9% of the calories from protein. Due to the higher fat proportions, the LCHP, 60% HF and 90% HF diets have a high caloric-density compared to the AIN93G standard chow. Detailed diet composition and calorie content are summarized in Table 21.

Figure 23:
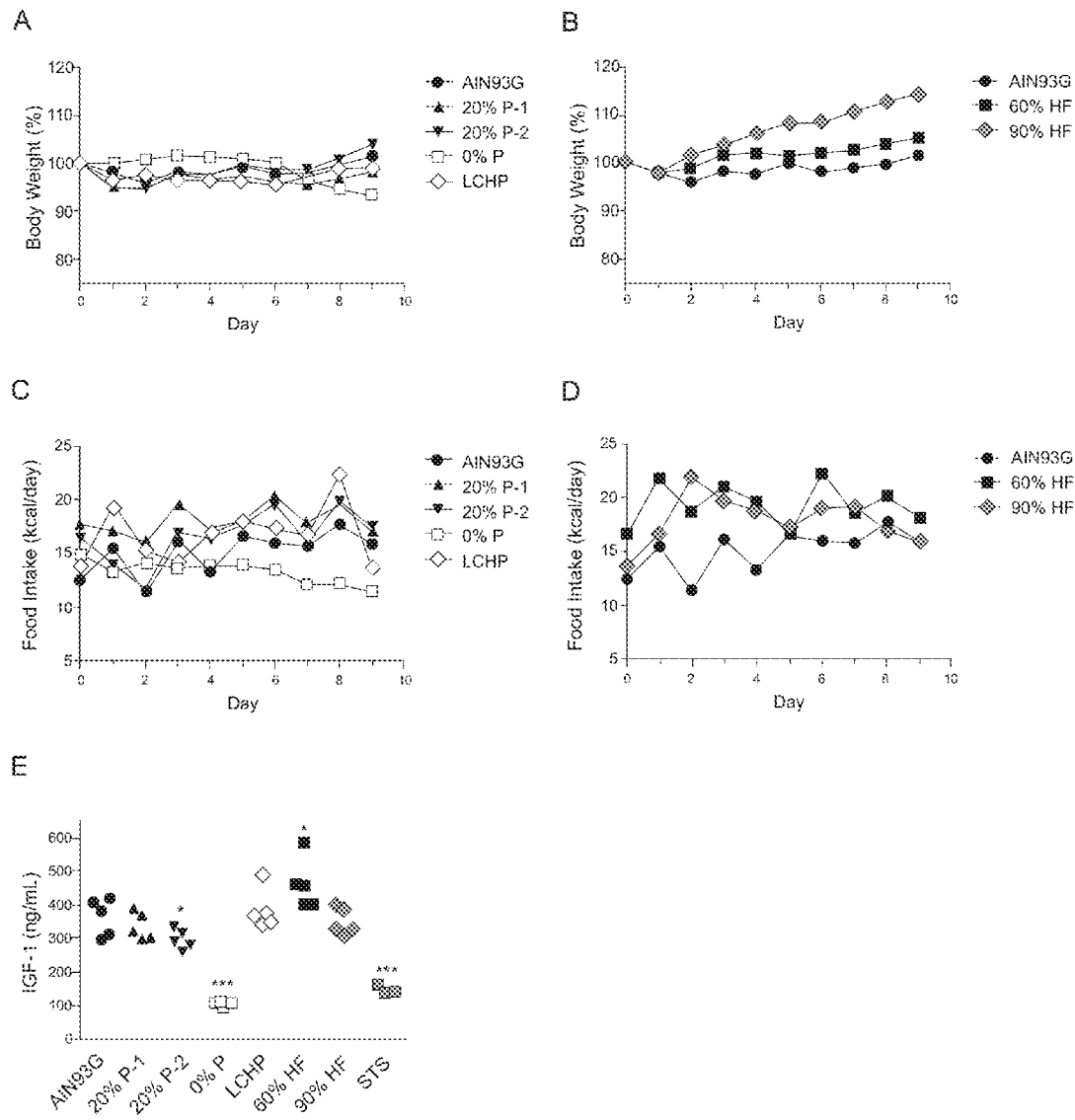
FIG. 23. Effects of Macronutrient defined Diets on Bodyweight, Food Intake, Glucose and serum IGF-1. Five female CD-1 mice, age 12-15 weeks were either fed ad lib with AIN93G rodent standard chow (black circle) or with A) two different low protein diets (20% P-1 and 20% P-2), a diet low in carbohydrates but high in protein (LCHP), a protein deficient diet (0% P) or B) a high fat diet (60% HF) and ketogenic diet (90% HF). A detailed overview over the macronutrients is given in Table. 1. C) Daily ad lib calorie intake for diets AIN93G, 20% P-1, 20% P-2, LCHP and 0% P. D) Daily ad lib calorie intake for diets 60% HF and 90% HF; AIN93G shown as reference. All data presented as mean±SEM. E) Serum IGF-1 levels after 9 days of ad lib feeding. Lines represent mean; *$p<0.05$,*** $p<0.001$, ANOVA, Tukey's multiple comparison compared to AIN93G control.

Female CD-1 mice were fed ad lib with the experimental diets for nine consecutive days to establish bodyweight profiles (FIG. 23A, B) and to monitor the caloric intake (FIG. 23C, D). A significant food aversion was not observed but noticed that mice fed with the diet lacking proteins completely (0% P) reduced food consumption after 6 days (FIG. 23C). The reduced calorie intake caused weight-loss for animals in this experimental group (FIG. 23A). Mice in the ketogenic high-fat groups (60% HF and 90% HF) consumed more calories during the 9 days of feeding than mice fed with the AIN93G standard chow (FIG. 23D) and mice fed ad lib with the ketogenic 90% HF diet rapidly gained weight after 4-5 days (FIG. 23B). CD-1 mice in the experimental groups fed with diets 20% P and LCHP showed no difference in calorie intake or bodyweight compared to the mice fed with the AIN93G control diet (FIG. 23A, C).

Figure 27:
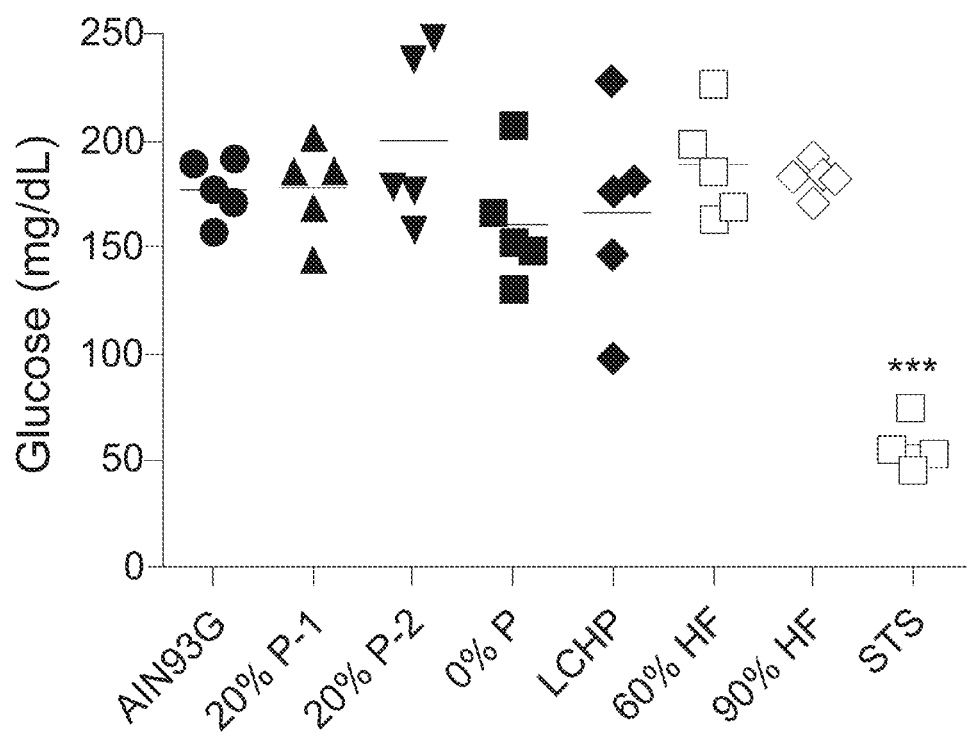
FIG. 27. Blood glucose levels after 9 days of ad lib feeding the indicated experimental diets. Lines represent mean.

Blood glucose levels at day 2, day 5 and at day 9 from mice on the macronutrient modified diets were not different from those on the standard chow diet (FIG. 27 and data not shown). By contrast, serum IGF-1 levels were significantly elevated ($P<0.05$) in mice on the ketogenic 60% HF diet for 9 days but not for mice fed with the ketogenic 90% HF diet (FIG. 23E). Interestingly, not only the macronutrient composition (e.g. the protein content) but also the fatty acid source differentially modulate circulating IGF-1 levels: the low protein diet 20% P-1 (containing soybean oil as the only fat source) did not reduce IGF-1 levels but the low protein diet 20% P-2 (coconut oil as the only fat source) significantly ($P<0.05$) reduced IGF-1 levels and there are no differences in these diets other than the fat source. The most noticeable effect on serum IGF-1 was in mice fed the protein deficient diet 0% P for 9 days. Circulating IGF-1 was reduced to approximately 30% of that in mice on the standard chow (FIG. 23E). The protein deficient diet 0% P was the only diet that reduced serum IGF-1 levels comparable to the 60 h short-term starvation.

3.3. Short-Term Calorie Restriction and Fasting Improve Stress Resistance

In mice, reduced serum IGF-1 and blood glucose levels promote the capability to cope with toxicity induced by high-dosed chemotherapeutic agents. Since short-term calorie restriction, but not the macronutrient defined diets (except for complete protein removal), reduced IGF-1 and glucose levels, a combinatorial approach was used to test whether diets with defined macronutrient deficiency fed at 50% of the regular daily calorie intake could result in enhanced chemo toxicity protection. 20% P diets were not included in the stress resistance experiments due to the fact that diet 0% P showed much more pronounced effects on serum IGF-1.

Figure 24:
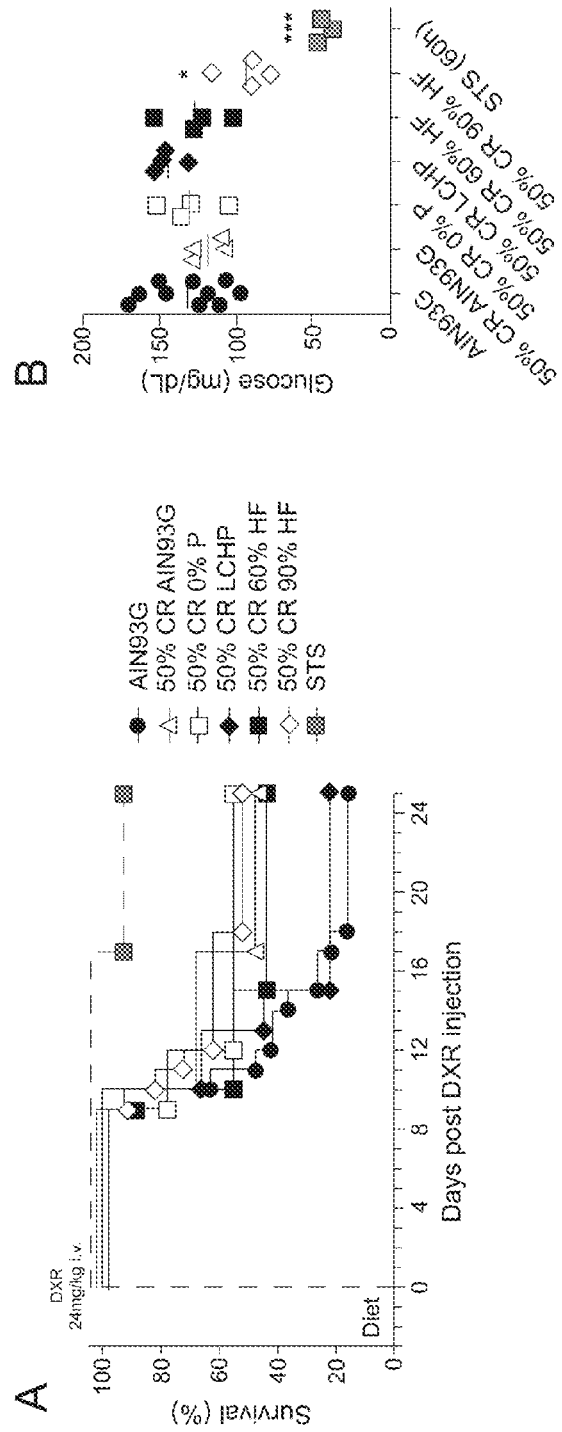
FIG. 24. A) Stress Resistance Test for Calorie Restricted Macronutrient defined Diets. Mice were fed ad lib (AIN93G), were fasted for 60 h (STS) or fed with 50% calorie restricted diets with defined macronutrient compositions (AIN93G, LCHP, 0% P, 60% HF, 90% HF) for 3 days (green box) prior to an intravenous injection of doxorubicin (24 mg/kg, red dashed line). Survival was followed for 25 days post injection, after which the remaining animals were considered survivors. B) Blood glucose levels after 3 days of feeding ad lib and CR diets, as well as after 60 h STS. Lines represent mean. * $p<0.05$, *** $p<0.001$, ANOVA, Tukey's multiple comparison. Survival data plotted from pair-matched pooled experiments with the statistical software Prism (GraphPad Software)
Figures 28A, 28B:
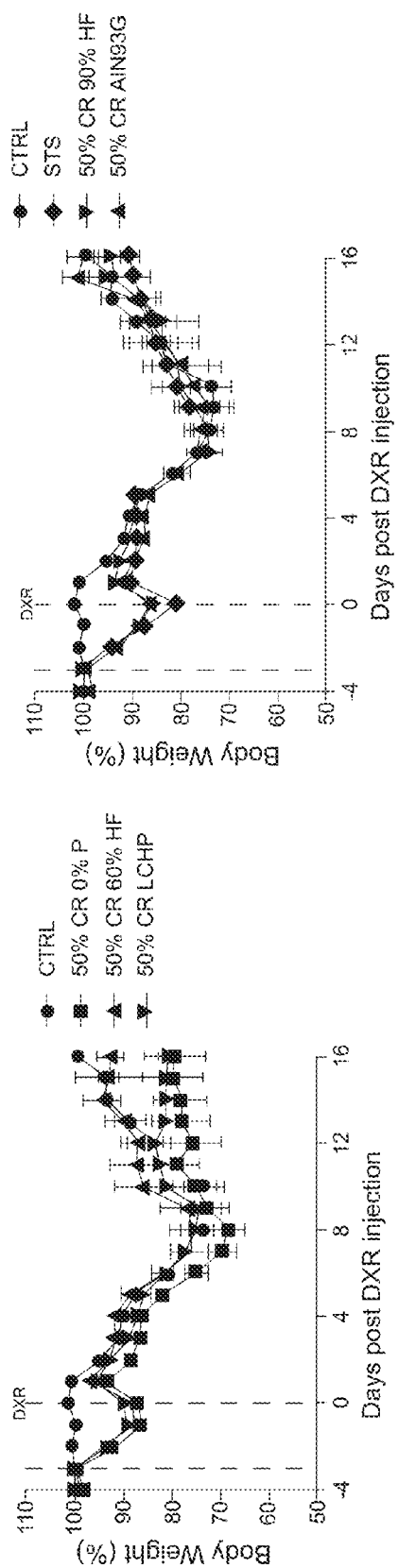
FIG. 28. A) Bodyweight profile for mice that were fed ad lib (AIN93G) or fed with 50% calorie restricted diets with defined macronutrient compositions (60% HF, LCHP, 0% P) for 3 days (green box) prior to an intravenous injection of doxorubicin (24 mg/kg, red dashed line). B) Bodyweight profile for mice that were fed ad lib (AIN93G), fed with 50% calorie restricted diets with defined macronutrient compositions (AIN93G, 90% HF) for 3 days or were fasted for 60 h (green box) prior to an intravenous injection of doxorubicin (24 mg/kg, red dashed line)

Stress resistance was tested in CD-1 mice fed either ad lib with AIN93G standard chow or with macronutrient defined diets reduced to 50% of the normal calorie intake for three days prior to doxorubicin (DXR, 24 mg/kg, i.v.) treatment (FIG. 24A). In the 50% calorie restricted groups mice lost 12-15% of their initial bodyweight after 3 days, whereas in the STS group mice lost 20% of their weight after 60 h. Following DXR treatment, AIN93G chow was provided ad lib for all animals and the mice regained weight until chemotoxicity-induced weight-loss set in (FIG. 28A, B). The weight-loss continued in all experimental groups until day 8 post injection, after which many animals slowly recovered. Mice fed the calorie restricted 0% P and LCHP diets never fully recovered their initial weight (FIG. 28A). Animals started to succumb to chemotoxicity 9-18 days post injection (FIG. 24A), in agreement with the reported onset and nadir days of myelo-suppression after DXR treatment (http://dailymed.nlm.nih.gov). Mice were considered survivors if they were alive 25 days post DXR injection. Mice fed ad lib with the AIN93G diet 3 days prior to DXR injection showed the worst outcome with only 16% surviving by day 25 (FIG. 24A). In contrast to the ad lib fed mice, the great majority (89%) of fasted (60 hours) mice survived the high-dose chemotherapy. Control mice treated with DXR showed signs of toxicity including reduced mobility, ruffled hair and hunched back posture whereas mice in the STS group showed no visible signs of stress or pain after the treatment (data not shown). Three days feeding of the combination of 50% CR with macronutrient modification prior to DXR injection improved the stress resistance in mice and resulted in 45-55% survival (FIG. 24A). There was no indication that fat or carbohydrate content affected the results because all diets achieved a similar rate of protection. The data indicates that short-term CR, not the fat or carbohydrate composition of the diet, confers partial chemo-protection which are not as potent as to those caused by fasting. Mice fed the 50% CR LCHP diet performed worse than all other CR fed groups, presumably because of the effect of the high protein content of this diet on IGF-1.

Blood glucose measurements revealed that three-days feeding of the calorie restricted modified diets was not sufficient to significantly reduce glucose levels, with the exception of the 50% CR ketogenic 90% HF diet (FIG. 24B). The reduction in glucose levels in the ketogenic group did not appear to enhance stress resistance. Mice in the STS group had significantly lower blood glucose levels than all other experimental groups (FIG. 24B).

3.4. A Low Protein Diet does not Appear Delay GL26 Glioma Progression

Figure 25B:
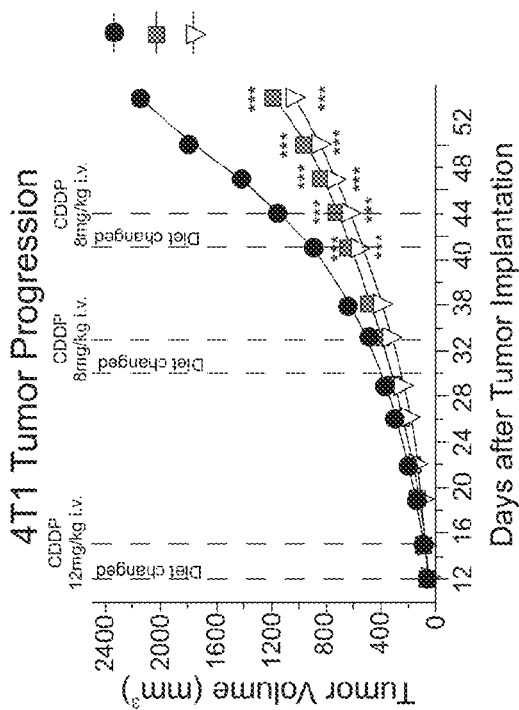
FIG. 25. Tumor Progression of GL26 Glioma and 4T1 Breast Cancer in vivo. A) Subcutaneous tumor progression of murine GL26 glioma is shown by total tumor volume in $mm^3$. Tumor measurements were started once the tumors became palpable under the skin at day 10. Animals were fed ad lib with either AIN93G (N=5) as a control or with the low protein diet 20% P-1 (N=6). All data presented as mean±SEM. B) Subcutaneous tumor progression of murine 4T1 breast cancer is shown by total tumor volume in $mm^3$. Tumor measurements were started once the tumors became palpable under skin at day 12. Control animals (N=10) received no treatment and tumor progressed rapidly, reaching the endpoint volume of 2000 $mm^3$ by day 54 post tumor implantation. Cispaltin (CDDP) animals (N=9) were injected at days 15, 33 and 44. The first CDDP dose was delivered at 12 mg/kg by intravenous injection, the two subsequent injection were delivered at 8 mg/kg to avoid chemotoxicity. Mice in the 50% ICR+ CDDP group (N=9) were fed in intermittent regimens with the AIN93G diet reduced to 50% of the daily calorie intake of the control group for three days (ICR, green box) prior to cisplatin injection. Injection schedule identical as for the CDDP group. All data presented as mean±SEM; *** $p<0.001$, ANOVA, Tukey's multiple comparison, compared to control.
Figure 25A:
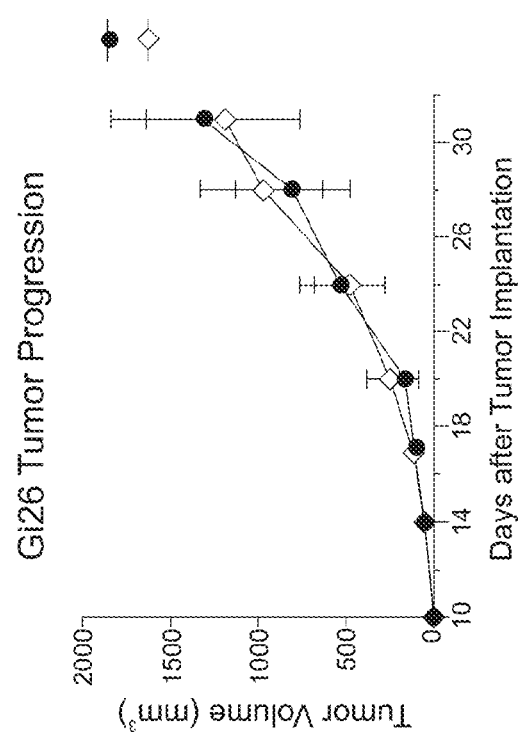

Diets low in protein have been shown to lower cancer risks while high-calorie and high-protein diets are linked to obesity and promote hormonal, metabolic, and inflammatory alterations that modulate carcinogenesis. To test the effects of a low protein diet in a glioma model, mice were switched from the standard chow (18.8% of calories are from protein, Table 1) to a diet low in protein (20% P-1, 3.9% of calories are from protein) 10 days after the implantation of GL26 cells when the tumor was palpable (FIG. 25A). Low protein diet fed mice displayed tumor progression that was not distinguishable from that in mice fed ad lib with the AIN93G diet (FIG. 25A). These results indicate that the tumor progression could not be retarded by protein-restriction once the tumor was established.

3.5. Short-Term Intermittent Calorie Restriction does not Enhance Efficacy of Chemotherapy Against Breast Cancer The efficacy of STS in augmenting the treatment of various cancers is twofold: it protects against chemotherapy-induced toxicity to normal cells/tissues and sensitizes malignant cells to chemotherapeutic agents. Nonetheless, even short interval fasting (e.g. 4 days) can be a challenge for the majority of people and thus the "milder" calorie restricted approach could be a more feasible solution. To test whether a short-term intermittent 50% CR (ICR) diet could result in similar beneficial effects as the established fasting protocols, murine 4T1 breast cancer cells were implanted subcutaneously into female BalB/C mice and monitored the tumor progression. Twelve days after tumor implantation, the tumor volume was measured and mice were assigned to either the untreated control group (AIN93G), a group treated with cisplatin (CDDP) or a group intermittingly fed with 50% CR (ICR) for three days prior to cisplatin treatment. The tumor in the untreated control group progressed rapidly and reached the experimental endpoint volume of 2000 mm$^3$ 54 days after tumor implantation (FIG. 25B, black circles). Three cycles of cisplatin treatment delayed the tumor progression; the tumor volume of these mice was approximately half the size of that in untreated mice (FIG. 25B, blue squares). In contrast to STS, an intermittent 50% calorie restricted AIN93G feeding regimen fed to mice for three days prior to the cisplatin injections did not result in the sensitization of the tumor and did not augment the chemotherapy (FIG. 25B, orange triangle). Tumor volumes in this experimental group did not significantly differ from tumor volumes in mice that were treated with cisplatin alone.

4. Discussion

It has previously been shown that a major reduction in blood glucose and IGF-1 levels is partly responsible for the beneficial effects of 2-3 days of fasting in animal cancer models. In mice, a 60 h short-term fasting reduces body-weight by 20% or more, serum IGF-1 by up to 75%, and glucose by up to 70%. Under these conditions, animals become highly stress resistant, in agreement with results in yeast, and a variety of tumors are sensitized to chemo- and radio-therapy. When a 20% weight-loss was employed as an endpoint, as expected, various degrees of CR regimens resulted in progressively quicker weight loss but also reduction in IGF-1 and glucose. However, it was also observed that the much shorter STS regimen had more pronounced effects on glucose than most of the CR diets, even when the CR diets were maintained for 9-13 days and caused an equivalent 20% weight loss. The less pronounced effects of calorie restricted diets, when compared to short-term starvation, might be explained by a distinct physiological response that is unique to conditions under which nutrients are completely absent (Lee and Longo, 2011). For example, the decrease in blood glucose caused by short-term fasting in this study was 70% and occurred within 60 h vs. the 40% glucose reduction caused by a 90% CR diet after 96 h.

When deprived of food, mammals generally undergo three metabolic stages: 1) a post-absorptive phase, lasting for 10 or more hours following food ingestion, which involves the use of glycogen as the main stored energy source, 2) an amino acid-dependent glucose generation by gluconeogenesis once the liver glycogen storage has been depleted, and 3) a phase in which the remaining glucose is mostly consumed by the brain while glycerol and fatty acids are released from adipose tissue and become the major energy source. The fat-derived ketone-bodies become the main carbon sources in a matter of days of fasting. Within the body, these changes trigger a cellular response including the down-regulation of pathways involved in proliferation, cell growth and the reduced production of reactive oxygen species while simultaneously increasing genomic stability and cellular stress resistance. Glucose is the major energy source for proliferating cells such as malignant cells and elevated blood glucose has been associated with increased cancer risk. Many cancer cells have elevated glucose uptake rates and rely on glycolysis followed by lactic acid fermentation even in the presence of oxygen, instead of glycolysis followed by oxidation of pyruvate, a phenomenon known as the Warburg effect (Oudard et al., 1997; Warburg, 1956). In normal cells, the reduction of blood glucose as well as IGF-1 likely contribute to a differential regulation of the activation of stress resistance transcription factors that are negatively regulated by nutrient sensing pathways and cell cycle progression. In cancer cells, the low glucose instead presents a specific and major challenge; particularly when chemotherapy drugs are also present.

In agreement with the partial effects on blood glucose and IGF-1, the results of this disclosure indicate that 72 hour of 50% CR, but also of diets restricted in carbohydrates or proteins, have only partial effects on stress resistance. The combination of a short-term intermittent 50% CR regimen and cisplatin treatment did not appear in the augmentation of chemotherapy efficacy in contrast to the combination of STS and chemotherapy. The present disclosure suggests that three days of a 50% ICR did not significantly reduce blood glucose levels and thus might not cause a sufficient reduction in the carbon sources metabolized by murine breast cancer cells within this interval. None of the 50% dietary restricted and macronutrient defined diets fed for 3 days, except for the ketogenic 90% HF diet, lowered blood glucose levels, which has been shown to promote host-protection and tumor sensitization. Interestingly, a 50% reduction in the calories consumed on a ketogenic diet leads to a 30% reduction in blood glucose levels after three days of feeding, an effect presumably due to the very low carbohydrate content (less than 1%) of this diet. However, stress resistance experiments in this disclosure indicate that this reduction did not improve survival. In addition, no mice from any of the CR diets achieved protection equivalent to that caused by 60 h fasting (STS) in the experiments presented here. Additional studies with extended feeding regimes and larger experimental group size will be necessary to understand whether specific diets may be sufficient to achieve DSR and DSS effects that are close to those caused by fasting cycles. Future studies could also evaluate the effects of various macronutrient-defined and CR diets on ROS production, tumor progression and stress resistance.

Dietary protein and resulting amino acid-content seems to affect longevity and healthy aging. Restricting protein intake shares some of the physiological effects of CR, including a decreased metabolic rate, reduced oxidative damage, enhanced hepatic resistance to toxins and oncogenic insults, decreased preneoplastic lesions and tumors. Furthermore, both CR and protein restriction reduce serum IGF-1 levels, which might be one of the contributors to longevity extension as the IGF-1-like signaling pathways regulate lifespan in various model organisms such as *C. elegans, D. melanogaster* and mice. The IGF-1 pathway has been shown to affect both animal life span and sensitivity to oxidative stress, consistently with the greater resistance to oxidative stress in IGF-1 receptor deficient mice. The forkhead box protein O1 (FOXO1), a down-stream target of IGF-1/AKT signaling, can enter the nucleus in the absence/reduction of IGF-1/AKT signaling where it can modulate a wide array of genes involved in oxidative stress resistance, longevity, and metabolism, and thus it is a key mechanism involved in protection against age associated stress and disease development. It has previously been suggested that a reduction in IGF-1 results in improved stress resistance to high dose chemotherapy as well as tumor sensitization. IGF-I exerts a potent tumorigenic effect on a variety of cancer cells by increasing their proliferative rate and inhibiting apoptosis. Studies in mice with deficiencies in the downstream effectors of IGF-R signaling, including mTOR inhibition by rapamycin and S6K1, demonstrate the central role of intracellular mitogenic pathways downstream of IGF-I in regulating lifespan and stress resistance while simultaneously reducing tumor growth. In addition, humans with growth hormone receptor deficiency have significantly lower circulating IGF-1 levels, and also exhibit drastically reduced incidence of cancer and diabetes, which are more common among age matched relatives with intact growth hormone receptor.

Mice in the group fed with a calorie restricted low carbohydrate diet (LCHP) had the worst survival of all CR groups, comparable to that of mice in the control group. The fact that mice in this group consumed similar, or higher amounts of fat-derived calories (20.9% in 50% CR LCHP vs. 17.2% ad lib AIN93G) and more importantly protein-derived calories (22.6% in 50% CR LCHP vs. 18.8% ad lib AIN93G) during three days of feeding, might explain this lack of protection. Of note is that the results presented on the induction of stress resistance are based on relatively short (72 h) feeding periods, thus if cannot be excluded that longer CR regimen with either altered calorie and/or macronutrient restrictions could result in an improved stress resistance.

Figure 29:
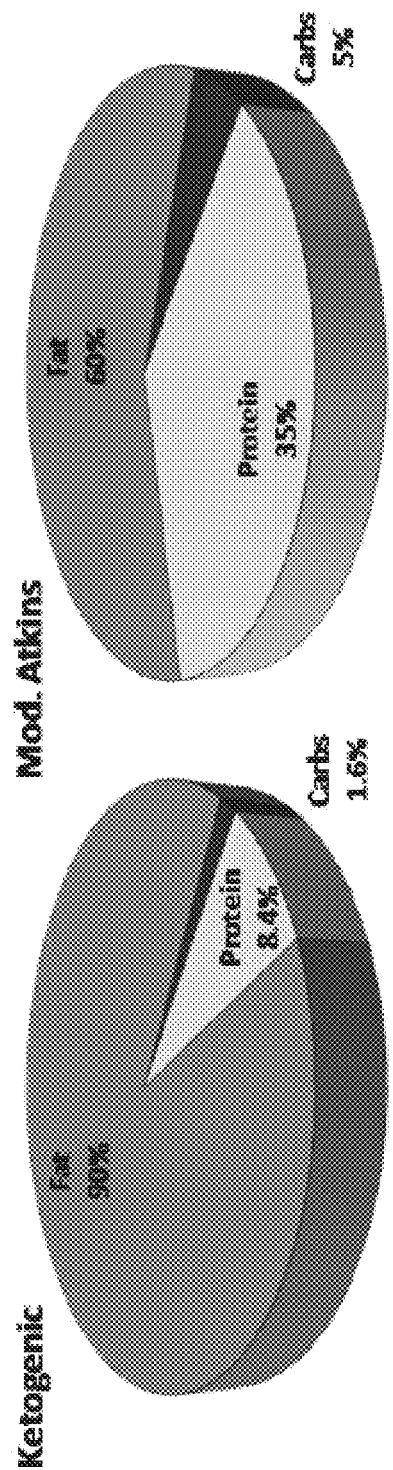
FIG. 29. Calories supplied by macronutrients of the classic ketogenic diet and modified Atkins diet in %.

Ketogenic diets are used extensively in the treatment of refractory epilepsy in children, but have also been studied in cancer treatment. To determine how this approach would compare with our stress resistance and potentially tumor sensitization experiments, two ketogenic diets were designed: our 90% HF diet (% calorie ratio of fat:carbohydrates:protein of 90%:1%:9%; FIG. 21) is nearly identical (±0.5% variation) to the classic ketogenic diet with a ratio of fat:carbohydrates:protein of 90%:1.4%:8.6% respectively (FIG. 29). The high-fat diet 60% HF (% calorie ratio of fat:carbohydrates:protein of 60%:31%:9%) contains fat ratios similar to the fat ratio used in the modified Atkins diet (% calorie ratio of fat:carbohydrates:protein of 60%:5%:35%; FIG. 29), but the protein content was reduced because previous work has established that protein, and not carbohydrates, regulate IGF-1 levels in human. The results described here demonstrate that neither glucose nor IGF-1 levels were significantly reduced after feeding both ketogenic diets for 9 consecutive days.

To evaluate the effects of saturated vs. unsaturated fatty acids, as well as medium-vs. long-chain fatty acids in cancer treatment, two diets were designed that were isocaloric to the control diet with soybean oil or coconut oil as a fat source but had low protein content. Long-chain unsaturated fatty acids are found in most commonly used dietary fats and vegetable oils such as soybean oil, while short- and medium-chain saturated fatty acids (e.g. lauric acid and myristic acid) are found in relatively high abundance in palm kernel oil and coconut oil. The medium-chain triglycerides (MCT) can easily by hydrolyzed in the gastro-intestinal tract and can be transported through the portal venous system towards the hepatocytes, while most of the long-chain fatty acids are transported as chylomicrons in the lymphatic system and packaged into triglycerides in the liver. MCTs can easily be fed into the mitochondrial β-oxidation, while LCTs rely on transporters, such as carnitine, to enter the mitochondrial matrix in hepatocytes. Data from human studies has indicated that consumption of MCTs or diets with higher unsaturated to saturated fatty acid ratio are associated with decreasing blood glucose, improving lipid profile, and reducing obesity. In a study of biochemical and anthropometric profiles in women with abdominal obesity, dietary supplementation with coconut oil promoted a reduction in abdominal obesity.

The beneficial effects of prolonged CR are known for over a century now. The problems associated with translating CR into any clinical application is that long-term CR delays but does not stop the progression of many malignant diseases and is associated with a chronic reduced weight state that might be detrimental for cachectic cancer patients, or patients at risk to become cachectic, but also might chronically reduce fat and other reserves that may increase frailty particularly in elderly patients. In fact, prolonged CR can delay wound healing and immune function, which might present an additional hurdle for the great majority of patients receiving chemotherapy or undergoing surgery. Furthermore, the 75% reduction in serum IGF-1 caused by a 2-5-day fast in mice and humans cannot be achieved by a more moderate CR which does not reduce IGF-1 levels in humans unless the protein intake is also restricted. Even when combined with protein restriction, chronic CR only causes a 30% reduction of IGF-1 in humans. Because of the consistent effects on glucose and IGF-1, and consequent effects on protection of normal and sensitization of cancer cells without the chronic under-weight, periodic fasting cycles appear to have the highest potential to protect patients treated with a variety of chemotherapy drugs while augmenting their efficacy in the treatment of many tumors.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method for lowering glucose and/or IGF-1 levels in a subject, the method comprising:
   providing the subject with a low protein diet having less than about 10 percent calories from protein sources, the low protein diet providing at most 50% of the normal caloric intake of the subject with at least 50% of kilocalories being derived from fat; and
   monitoring glucose and/or IGF-1 levels of the subject to determine whether protein diet intake should be increased or decreased.

2. The method of claim 1, wherein the low protein diet has from 0 to 10 percent calories from protein sources.

3. The method of claim 1, wherein the low protein diet has from 0 to 5 percent calories from protein sources.

4. The method of claim 1, wherein the low protein diet has about 0 percent calories from protein sources.

5. The method of claim 2 wherein the low protein diet includes fat sources such that at least 50 percent of calories from fat are from long-chain unsaturated fatty acids.

6. The method of claim 5 wherein the fat source includes vegetable oil.

7. The method of claim 6 wherein the vegetable oil is soybean oil.

8. The method of claim 1 wherein the low protein diet includes fat sources such that at least 50 percent of calories from fat are from long-chain unsaturated fatty acids having from 13 to 28 carbon atoms.

9. The method of claim 1, wherein the low protein diet includes fat sources such that at least 25 percent of calories from fat are short-chain fatty acids having from 2 to 7 carbon atoms and/or from medium-chain saturated fatty acids having from 8 to 12 carbon atoms.

10. The method of claim 9, wherein the fatty acids are lauric and/or myristic acid.

11. The method of claim 9, wherein the fatty acids are from olive oil, kernel oil and/or coconut oil.

12. The method of claim 1, wherein the low protein diet includes calories from fat in an amount from about 0 to 22 percent of total calories contained in the diet.

13. The method of claim 1 wherein the low protein diet is administered to the subject for a first time period from 5 days to 14 days.

14. The method of claim 13 wherein the low protein diet provides from 4.5 to 7 kilocalories per pound of subject for a first day (day 1) and then 3 to 5 kilocalories per pound of subject per day for a second to fifth day (days 2-5).

15. The method of claim 14 further comprising administering a second diet to the subject for a second time period following the low protein diet wherein the second diet provides an overall calorie consumption that is within 20 percent of a subject's normal calorie consumption for 25 to 26 days.

16. The method of claim 1 wherein the low protein diet includes an amino acid specific supplement.

17. The method of claim 16 wherein the an amino acid specific supplement provides excess levels of non-essential amino acids to be consumed for a period of 5 to 7 days together with very low protein amounts or no protein diet.

18. The method of claim 16 wherein the amino acid specific supplement substantially excludes isoleucine, leucine, lysine, methionine, phenyalanine, threonine, tryptophan, valine, and arginine.

19. The method of claim 16 wherein the total weight of isoleucine, leucine, lysine, methionine, phenylalanine, threonine, tryptophan, valine, and arginine in the low protein diet is less than 5 weight percent.

20. The method of claim 16 wherein the total weight of isoleucine, leucine, lysine, methionine, phenylalanine, threonine, tryptophan, valine, and arginine in the low protein diet is less than 1 weight percent.

21. The method of claim 16 wherein the total weight of isoleucine, leucine, lysine, methionine, phenylalanine, threonine, tryptophan, valine, and arginine in the low protein diet is less than 0.5 weight percent.

22. The method of claim 16 wherein amino acid specific diet provides an amino acid selected from the group consisting of alanine, aspartic acid, cysteine, glutamic acid, glycine, histidine, proline, serine, and tyrosine as a source of nitrogen.

* * * * *